US012565495B2

(12) United States Patent
Tian et al.

(10) Patent No.: US 12,565,495 B2
(45) Date of Patent: Mar. 3, 2026

(54) VMAT2 INHIBITOR AND PREPARATION METHOD THEREFOR AND APPLICATION THEREOF

(71) Applicant: Luye Innomind Pharma Shijiazhuang Co., Ltd., Shijiazhuang City (CN)

(72) Inventors: Jingwei Tian, Yantai (CN); Rui Zhang, Yantai (CN); Liang Ye, Yantai (CN); Dawei Yu, Yantai (CN); Guangying Du, Yantai (CN); Zongliang Liu, Yantai (CN); Fangxia Zou, Yantai (CN); Bo Cui, Beijing (CN)

(73) Assignee: Luye Innomind Pharma Shijiazhuang Co., Ltd., Shijiazhuang City (CN)

( * ) Notice: Subject to any disclaimer, the term of this patent is extended or adjusted under 35 U.S.C. 154(b) by 978 days.

(21) Appl. No.: 17/634,977

(22) PCT Filed: Aug. 11, 2020

(86) PCT No.: PCT/CN2020/108314
§ 371 (c)(1),
(2) Date: Feb. 13, 2022

(87) PCT Pub. No.: WO2021/027792
PCT Pub. Date: Feb. 18, 2021

(65) Prior Publication Data

US 2022/0340562 A1 Oct. 27, 2022

(30) Foreign Application Priority Data

Aug. 12, 2019 (CN) ......................... 201910739845.5
Nov. 11, 2019 (CN) ......................... 201911094084.9

(51) Int. Cl.
*C07D 471/04* (2006.01)

(52) U.S. Cl.
CPC ........ *C07D 471/04* (2013.01); *C07B 2200/13* (2013.01)

(58) Field of Classification Search
CPC ................ C07D 471/04; C07D 455/06; C07B 2200/13; A61P 25/14; A61P 25/00; A61K 31/4738
See application file for complete search history.

(56) References Cited

U.S. PATENT DOCUMENTS 6,087,376 A * 7/2000 Crooks et al.
8,562,949 B2 10/2013 Kung et al.
(Continued)

FOREIGN PATENT DOCUMENTS

CN 102120742 A 7/2011
CN 102285984 A * 12/2011
(Continued)

OTHER PUBLICATIONS

Zheng et al., "Vesicular Monoamine Transporter 2: Role as a Novel Target for Drug Development," *The AAPS Journal* 8(4): Article 78, Nov. 10, 2006. (11 pages).
(Continued)

*Primary Examiner* — Kortney L. Klinkel
*Assistant Examiner* — Jackson J Hernandez
(74) *Attorney, Agent, or Firm* — Seed Intellectual Property Law Group LLP

(57) ABSTRACT

The present invention relates to a class of compounds that serve as VMAT2 inhibitors, and relates in particular to a compound represented by formula (I), or a stereoisomer or pharmaceutically acceptable salt thereof, and a preparation method therefor, as well as the use thereof in the preparation of a medicament for treating diseases related to VMAT2.
(Continued)

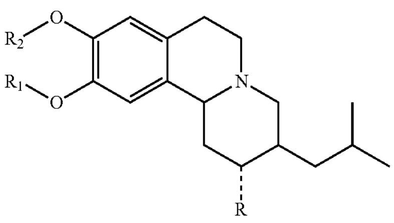

(I)

19 Claims, 9 Drawing Sheets

(56) References Cited

U.S. PATENT DOCUMENTS

| | | | |
|---|---|---|---|
| 11,306,082 | B2 | 4/2022 | Li et al. |
| 2008/0306269 | A1 | 12/2008 | Rishel et al. |

FOREIGN PATENT DOCUMENTS

| | | | | |
|---|---|---|---|---|
| EP | 3733666 | A1 | | 11/2020 |
| JP | 2009-535403 | A | | 10/2009 |
| TW | 201922745 | A | | 6/2019 |
| WO | 2007/130365 | A2 | | 11/2007 |
| WO | 2010/026436 | A2 | | 3/2010 |
| WO | WO2018222549 | A1 | * | 12/2018 |
| WO | 2019/129100 | A1 | | 7/2019 |

OTHER PUBLICATIONS

Office Action, dated Nov. 24, 2023, for Canadian Application No. 3,148,302. (5 pages).

Partial Supplementary European Search Report, dated Jun. 28, 2023, for European Application No. 20852655.8. (14 pages).

Purser et al., "Fluorine in medicinal chemistry," *Chemical Society Reviews* 37:320-330, Feb. 2008. (12 pages).

Supplementary European Search Report, dated Oct. 4, 2023, for European Application No. 20852655.8. (18 pages).

CAS Registry No. 1980055-18-2, STN International, file Registry [online], entered STN: Aug. 25, 2016. (1 page).

CAS Registry No. 927182-65-8, STN-Registry, May 18, 2007. (1 page).

CAS Registry No. 956903-28-9, STN-Registry, Dec. 6, 2007. (1 page).

Hao et al., "Pancreas-Specific Delivery of ß-Cell Proliferating Small Molecules," *ChemMedChem Communications* 11:1129-1132, Apr. 2016.

International Search Report and Written Opinion, mailed Oct. 15, 2020, for International Application No. PCT/CN2020/108314, 20 pages (w/ English translation).

Kung et al., "In vivo imaging of vesicular monoamine transporter 2 in pancreas using an $^{18}$F epoxide derivative of tetrabenazine," *Nuclear Medicine and Biology* 35(8):825-837, Nov. 30, 2008.

Pál et al., "Compounds of Table 1: Synthesis of new benzo[a]quinolizine derivatives. I," *Magyar Kémiai Folyóirat* 75(1):1969. (2 pages).

* cited by examiner

VMAT2 INHIBITOR AND PREPARATION METHOD THEREFOR AND APPLICATION THEREOF

TECHNICAL FIELD

The present invention relates to a class of compounds that serve as VMAT2 inhibitors or a stereoisomer or pharmaceutically acceptable salt thereof, and the use thereof in the field of diseases related to VMAT2.

BACKGROUND ART

Tardive dyskinesia (TD), also known as tardive hyperactivity disorder, is a disease first proposed by Faurbye in 1964. The disease is more common in patients who have taken antipsychotic drugs in large doses on a long-term basis. Clinically, the disease is mainly characterized by involuntary, rhythmic repetitive and stereotyped movement, which often involves the lower jaw, lips, and tongue. Other medicaments can also cause tardive dyskinesia, such as medicaments for treating Parkinson's Disease (levodopa).

Vesicular monoamine transporter 2 (VMAT2) is a transporter located on the vesicle membrane inside the presynaptic membrane and its function lies in reuptake and delivery of monoamine transmitters such as dopamine (DA) or 5-hydroxytryptamine into vesicles so as to prevent the monoamine transmitters from being metabolized in the cytoplasm. VMAT2 inhibitors can antagonize the reuptake function of VMAT2 so that dopamine cannot be reuptaken and delivered into vesicles by VMAT2 and is metabolized by the enzymes in the cytoplasm. Hence, the release of dopamine in the synaptic cleft is reduced, thereby further achieving the purpose of treating tardive dyskinesia.

Tetrabenazine (TBZ) is the first marketed selective VMAT2 inhibitor and its metabolite in vivo, trans (2,3)-dihydrotetrabenazine (DHTBZ), also has a selective VMAT2 inhibitory activity. In April 2017, the FDA approved valbenazine (VBZ) for the treatment of adult tardive dyskinesia. Valbenazine is prepared by esterification of the metabolite, DHTBZ, of tetrabenazine, has a longer half-life than tetrabenazine, does not require frequent dosing, has definite efficacies and reliable safety and is well tolerated.

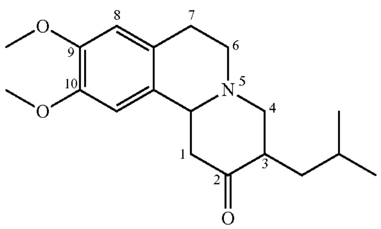

TBZ

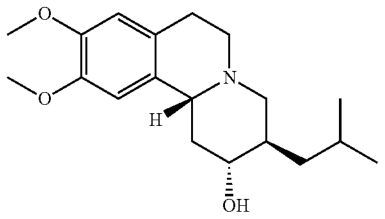

DHTBZ

-continued

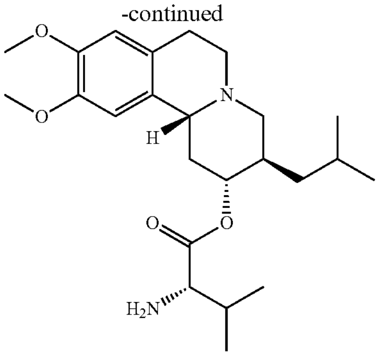

VBZ

Tetrabenazine has issues such as a short half-life and multiple dosing. A large number of tetrabenazine metabolites exist, leading to serious adverse reactions and black box warning for adverse reactions of depression and suicidality. There is a large population with tardive dyskinesia, but only a small number of marketed medicaments exist. Therefore, there is still a need for VMAT2 inhibitors with better activity in this field to meet a wide range of clinical needs.

SUMMARY OF THE INVENTION

To overcome the issues present in the prior art, the present invention provides a compound represented by formula (I), or a stereoisomer or pharmaceutically acceptable salt thereof, Formula (I)

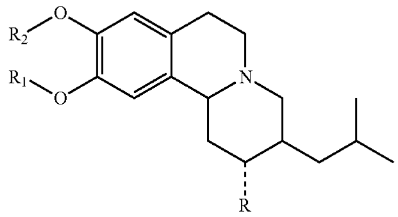

wherein

"- - - " represents: a single bond or a double bond;

when "- - - " is a single bond, R is selected from OH, H or

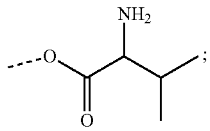

;

when "- - - " is a double bond, R is O;

$R_1$ is selected from hydrogen, methyl or ethyl;

$R_2$ is selected from $C_{2-10}$alkyl, $C_{3-6}$cycloalkyl, $C_{3-6}$cycloalkyl-$C_{1-6}$alkyl, 3- to 6-membered heterocycloalkyl-$C_{1-3}$alkyl, $C_{2-6}$alkenyl or $C_{1-6}$heteroalkyl unsubstituted or substituted with 1, 2 or 3 $R_3$; and $R_3$ is selected from F, Cl, Br, OH, SH or $NH_2$.

In some embodiments of the present invention, $R_2$ of the compound of formula (I) is selected from unsubstituted $C_{2-10}$alkyl, $C_{3-6}$cycloalkyl-$C_{1-6}$alkyl, or $C_{2-10}$alkyl substituted with 1, 2 or 3 $R_3$, and is preferably $C_{2-5}$alkyl unsubstituted or substituted with 2-3 $R_3$; $R_3$ is F, and other variables are as defined in the present invention.

In some embodiments of the present invention, $R_2$ of the compound of formula (I) is selected from ethyl, propyl, isobutyl, monofluorobutyl, monofluoropentyl, trifluoroethyl, trifluoropropyl, trifluorobutyl, trifluoropentyl, bisfluoroethyl or cyclopropanemethylene, and is preferably, trifluoroethyl or cyclopropanemethylene, and other variables are as defined in the present invention.

In some embodiments of the present invention, $R_1$ of the compound of formula (I) is methyl; "- - - " is a single bond, R is selected from OH or

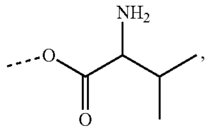

or "- - - " is a double bond, R is O; and other variables are as defined in the present invention.

In some embodiments of the present invention, the heteroatom in the 3- to 6-membered heterocycloalkyl or $C_{1-6}$heteroalkyl described for the compound of formula (I) is O, S or N; the number of heteroatom is 1-6, and preferably, one of the heteroatoms is O; and the number of C atom in the $C_{1-6}$heteroalkyl is 2-6 or 3-6 or 2-5 or 3-5 or 4-6 or 4-5.

The present invention also provides a compound having a structure represented by formula (II), or a stereoisomer or pharmaceutically acceptable salt thereof, wherein (II)

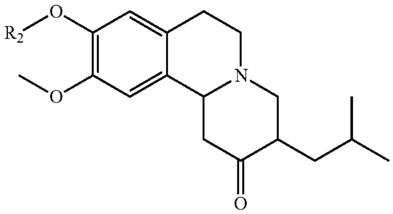

$R_2$ is selected from $C_{2-10}$alkyl, $C_{3-6}$cycloalkyl, $C_{3-6}$cycloalkyl-$C_{1-3}$alkyl, $C_{2-6}$alkenyl, $C_{1-6}$heteroalkyl unsubstituted or substituted with 1, 2 or 3 $R_3$, wherein $R_3$ is selected from F, Cl, Br, OH and $NH_2$.

In some embodiments of the present invention, $R_2$ of the compound of formula (II) is selected from unsubstituted $C_{2-10}$alkyl, $C_{3-6}$cycloalkyl-$C_{1-6}$alkyl, or $C_{2-10}$alkyl substituted with 1, 2 or 3 $R_3$, and is preferably $C_{2-5}$alkyl unsubstituted or substituted with 2-3 $R_3$; $R_3$ is F.

In some embodiments of the present invention, $R_2$ of the compound of formula (II) is selected from ethyl, propyl, isobutyl, monofluorobutyl, monofluoropentyl, trifluoroethyl, trifluoropropyl, trifluorobutyl, trifluoropentyl, bisfluoroethyl or cyclopropanemethylene, and is preferably trifluoroethyl or cyclopropane methylene.

In some embodiments of the present invention, the heteroatom in the $C_{1-6}$heteroalkyl described for the compound of formula (II) is O, S or N; the number of heteroatom is 1-6, and preferably, one of the heteroatoms is O.

The present invention also provides a compound having a structure represented by formula (III), or a stereoisomer or pharmaceutically acceptable salt thereof, wherein Formula (III)

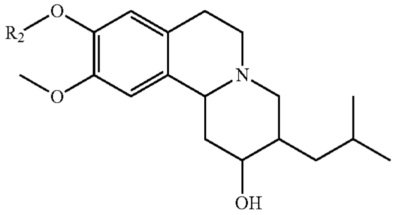

$R_2$ is selected from $C_{2-10}$alkyl, $C_{3-6}$cycloalkyl, $C_{3-6}$cycloalkyl-$C_{1-3}$alkyl, $C_{2-6}$alkenyl, $C_{1-6}$heteroalkyl unsubstituted or substituted with 1, 2 or 3 $R_3$, wherein $R_3$ is selected from F, Cl, Br, OH and $NH_2$.

In some embodiments of the present invention, $R_2$ of the compound of formula (III) is selected from unsubstituted $C_{2-10}$alkyl, $C_{3-6}$cycloalkyl-$C_{1-6}$alkyl, or $C_{2-10}$alkyl substituted with 1, 2 or 3 $R_3$, and is preferably $C_{2-5}$alkyl unsubstituted or substituted with 2-3 $R_3$; $R_3$ is F.

In some embodiments of the present invention, $R_2$ of the compound of formula (III) is selected from ethyl, propyl, isobutyl, monofluorobutyl, monofluoropentyl, trifluoroethyl, trifluoropropyl, trifluorobutyl, trifluoropentyl, bisfluoroethyl or cyclopropanemethylene, and is preferably trifluoroethyl or cyclopropane methylene.

In some embodiments of the present invention, the heteroatom in the $C_{1-6}$heteroalkyl described for the compound of formula (III) is O, S or N; the number of heteroatom is 1-6, and preferably, one of the heteroatoms is O.

The present invention provides a compound having a structure represented by formula (IV), or a stereoisomer or pharmaceutically acceptable salt thereof, wherein Formula (IV)

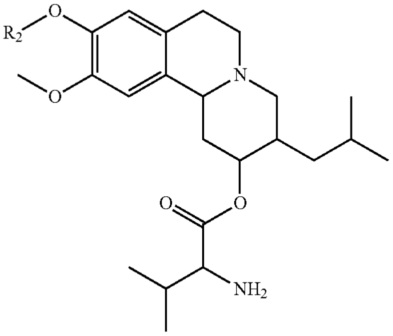

$R_2$ is selected from $C_{2-10}$alkyl, $C_{3-6}$cycloalkyl, $C_{3-6}$cycloalkyl-$C_{1-3}$alkyl, $C_{2-6}$alkenyl, $C_{1-6}$heteroalkyl unsubstituted or substituted with 1, 2 or 3 $R_3$, wherein $R_3$ is selected from F, Cl, Br, OH and $NH_2$.

In some embodiments of the present invention, $R_2$ of the compound of formula (IV) is selected from unsubstituted $C_{2-10}$alkyl, $C_{3-6}$cycloalkyl-$C_{1-6}$alkyl, or $C_{2-10}$alkyl substituted with 1, 2 or 3 $R_3$, and is preferably $C_{2-5}$alkyl unsubstituted or substituted with 2-3 $R_3$; $R_3$ is F.

In some embodiments of the present invention, $R_2$ of the compound of formula (IV) is selected from ethyl, propyl, isobutyl, monofluorobutyl, monofluoropentyl, trifluoroethyl, trifluoropropyl, trifluorobutyl, trifluoropentyl, bisfluoroethyl or cyclopropanemethylene, and is preferably trifluoroethyl or cyclopropane methylene.

In some embodiments of the present invention, the heteroatom in the $C_{1-6}$heteroalkyl described for the compound of formula (IV) is O, S or N; the number of heteroatom is 1-6, and preferably, one of the heteroatoms is O.

In some embodiments of the present invention, also provided are compounds having the following structures or enantiomers, diastereomers, mixtures thereof and a pharmaceutically acceptable salt thereof:

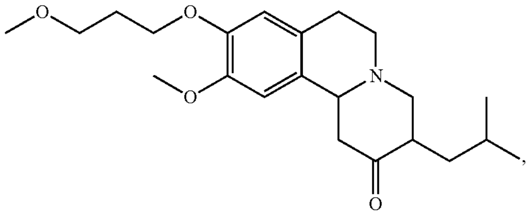,

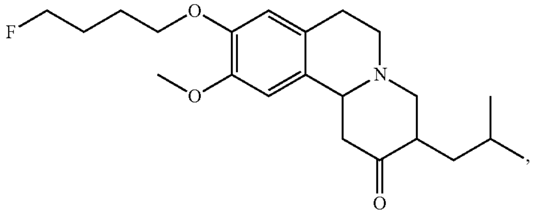,

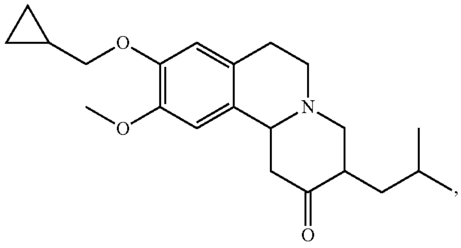,

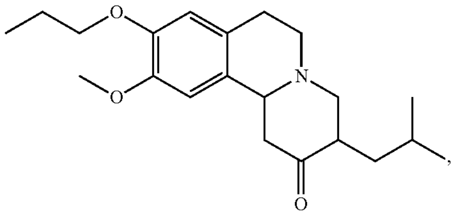,

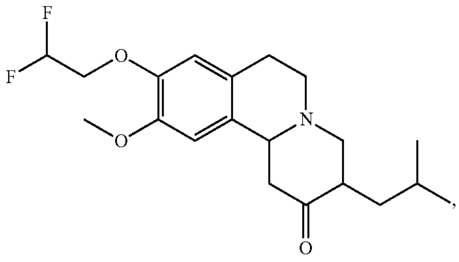,

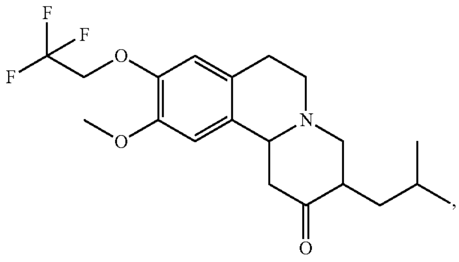,

-continued

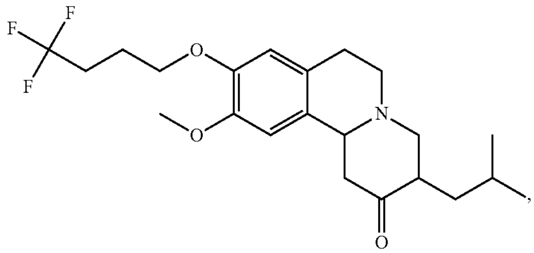,

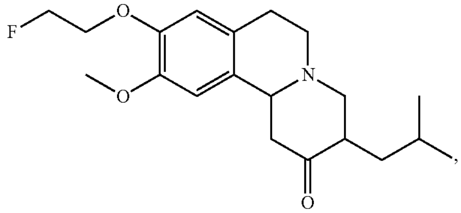,

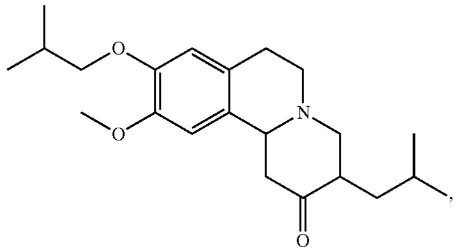,

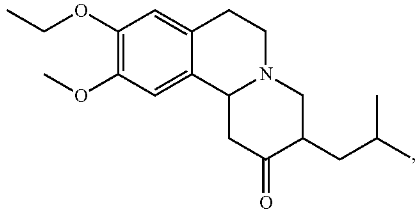,

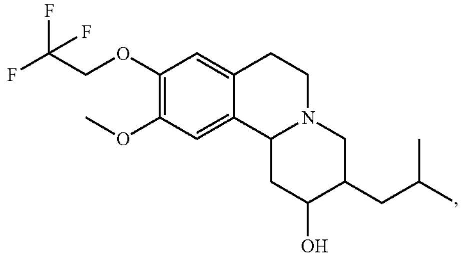,

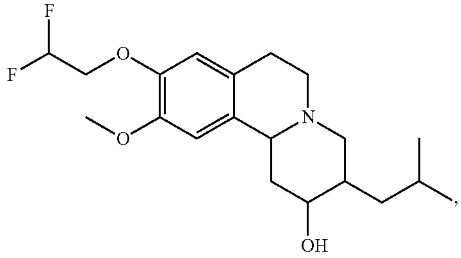,

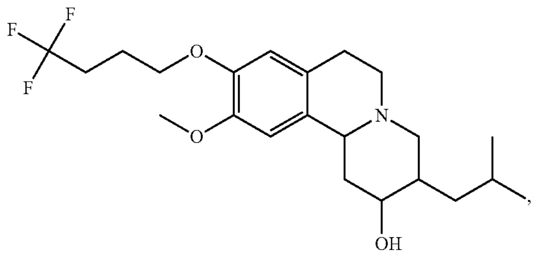,

-continued
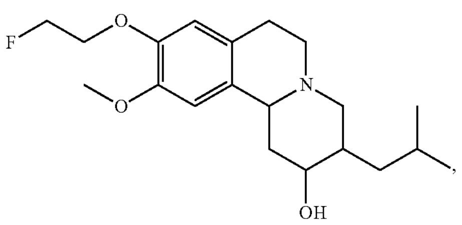
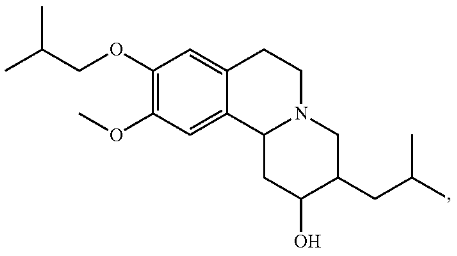
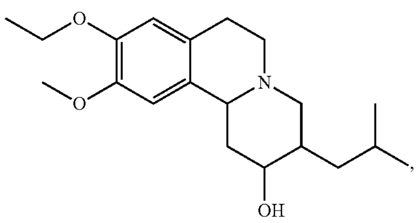
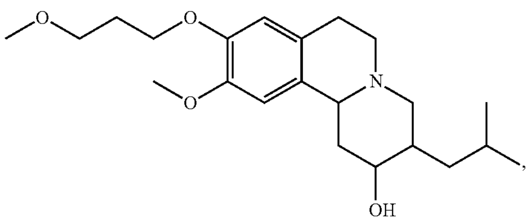
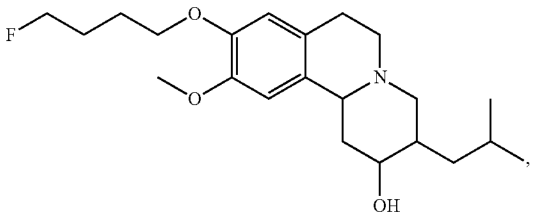
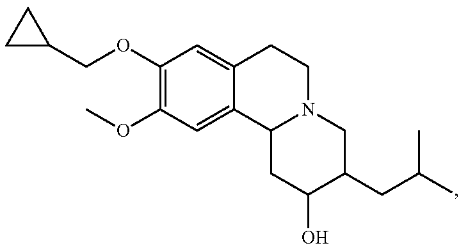
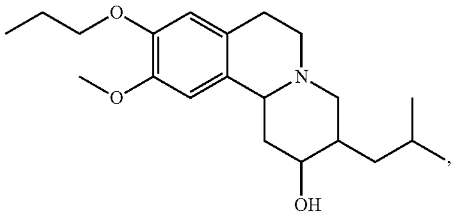
-continued
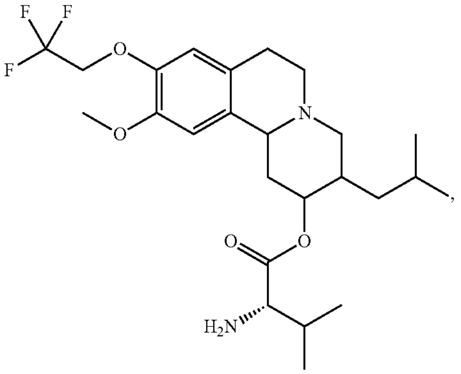
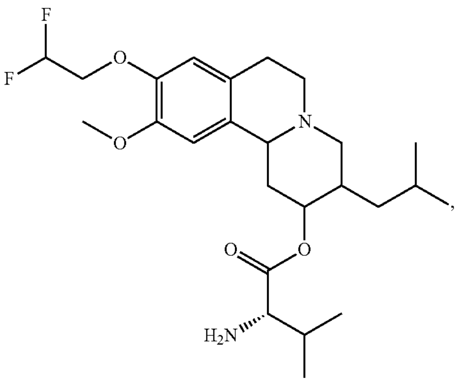
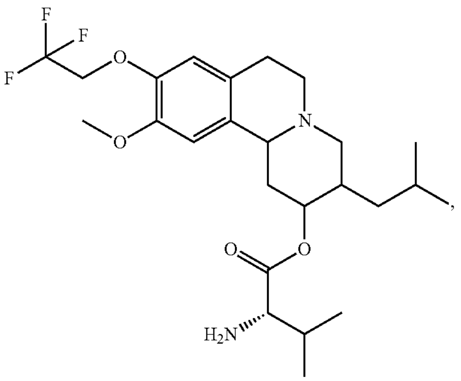
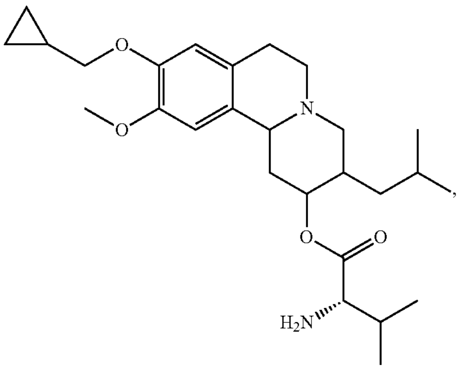

-continued
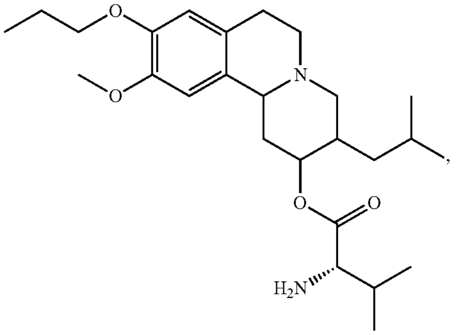
,
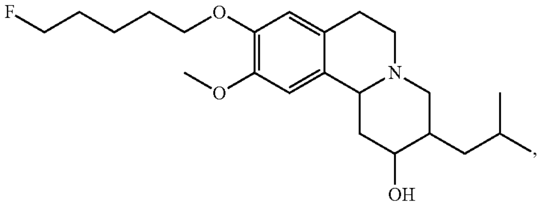
,
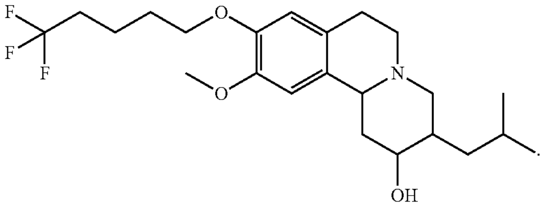
.
In some embodiments of the present invention, also provided are a valine ester and a pharmaceutically acceptable salt of compounds having the following structures:
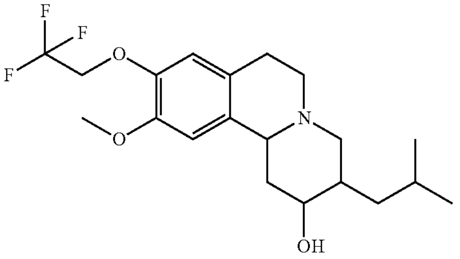
,
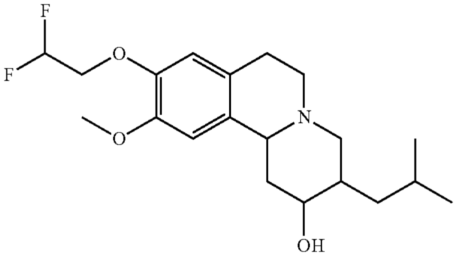 [SMILES: COc1cc2c(cc1OCC(F)F)CCN1CC(CC(C)C)C(O)CC21]
,
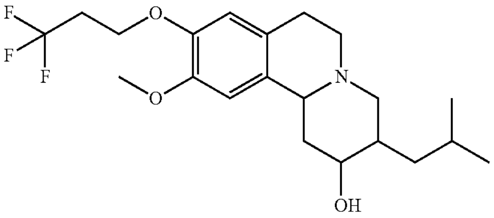
,
-continued
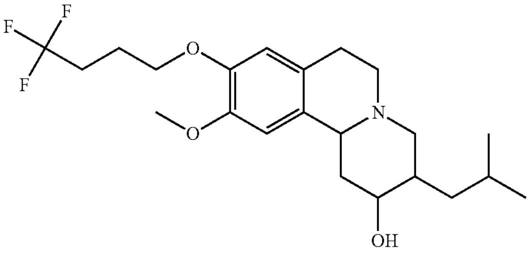 [SMILES: COc1cc2c(cc1OCCCC(F)(F)F)CCN1CC(CC(C)C)C(O)CC21]
,
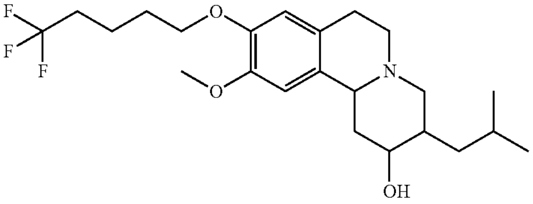
,
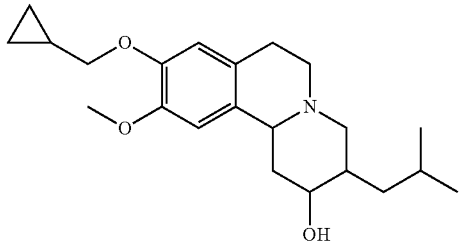
,
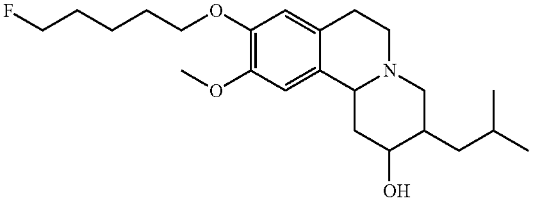
,
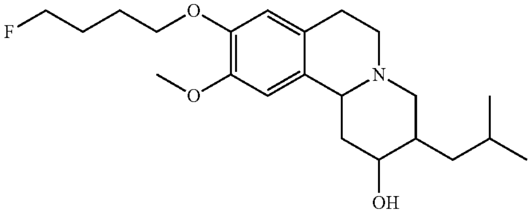
,
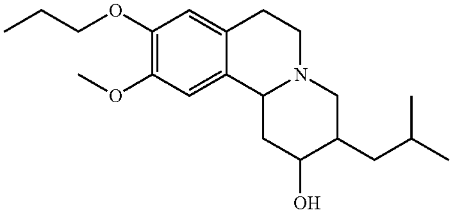
,
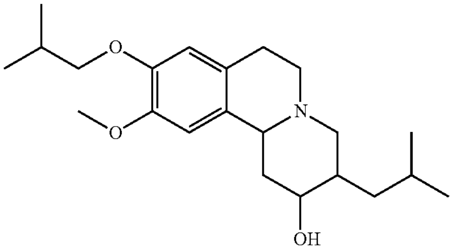
.
In some embodiments of the present invention, also provided are compounds having the following structures or a pharmaceutically acceptable salt thereof.

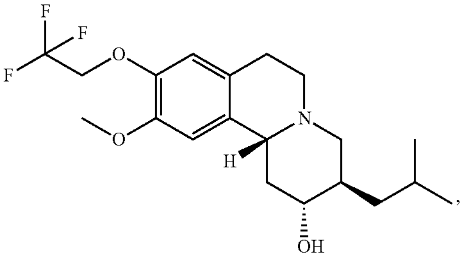
,
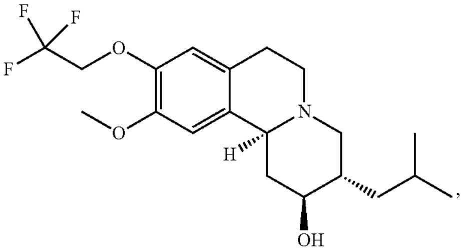
,
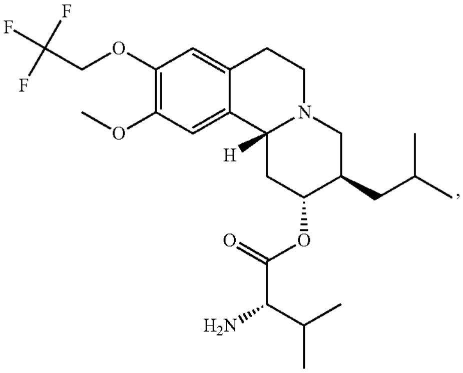
,
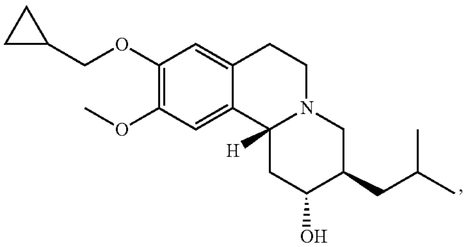
,
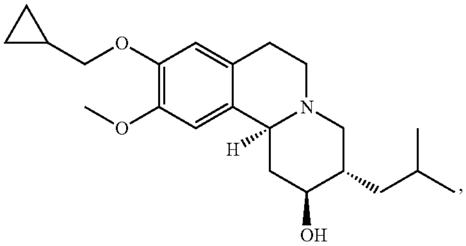
,
-continued
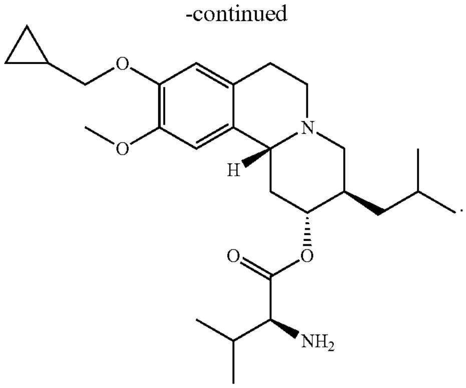
.
The present invention also provides a p-toluenesulfonate of any one of the compounds above, wherein the p-toluenesulfonate is preferably the following compound:
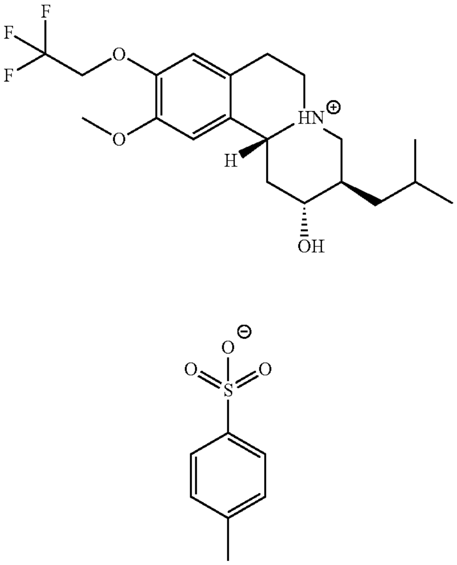
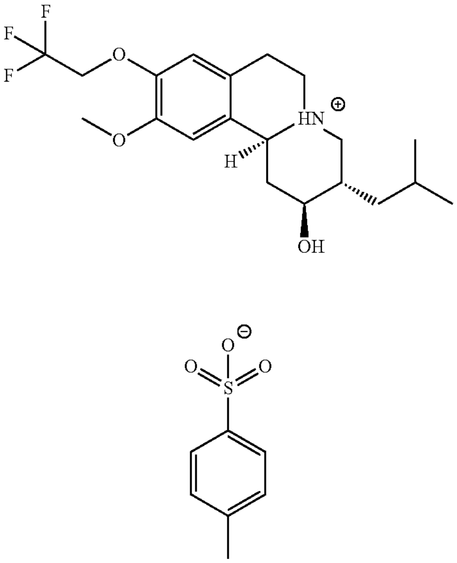

-continued

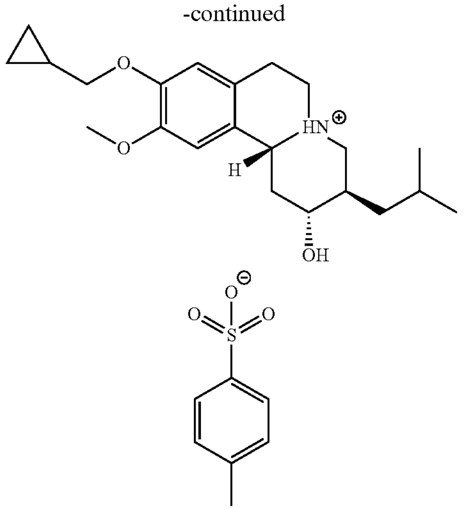

The present invention also provides five crystal forms of compound 11-P4S.

In some embodiments of the present invention, the crystal form A of 11-P4S belongs to the orthorhombic P21212 space group with the unit cell parameters being: a=27.14408(13) Å, b=16.24056(7) Å, c=6.13775(3) Å, α=90°, β=90°, γ=90°, V=2705.74(2) Å3, Z=4.

In some embodiments of the present invention, the crystal form A of 11-P4S comprising characteristic peaks of 2θ diffraction angle at 6.33±0.2°, 10.87±0.2° and 18.89±0.2° as measured by the X-ray powder diffraction using Cu—Kα radiation.

In some embodiments of the present invention, the crystal form A of 11-P4S comprising characteristic peaks of 2θ diffraction angle at 6.33±0.2°, 10.87±0.2°, 16.61±0.2°, 18.89±0.2°, 19.27±0.2° and 22.19±0.2° as measured by the X-ray powder diffraction using Cu—Kα radiation.

In some embodiments of the present invention, the crystal form A of 11-P4S comprising characteristic peaks of 2θ diffraction angle at 6.33±0.2°, 10.87±0.2°, 13.77±0.2°, 16.61±0.2°, 18.20±0.2°, 18.89±0.2°, 19.27±0.2°, 20.05±0.2°, 22.19±0.2°, 24.60±0.2° and 24.77±0.2° as measured by the X-ray powder diffraction using Cu—Kα radiation.

In some embodiments of the present invention, the crystal form A of 11-P4S has an X-ray powder diffraction pattern substantially as shown in FIG. 2-1 by Cu—Ka radiation.

In some embodiments of the present invention, the crystal form B of 11-P4S comprising characteristic peaks of 2θ diffraction angle at 6.32±0.2°, 5.42±0.2° and 10.85±0.2° as measured by the X-ray powder diffraction using Cu—Kα radiation.

In some embodiments of the present invention, the crystal form B of 11-P4S comprising characteristic peaks of 2θ diffraction angle at 6.32±0.2°, 5.42±0.2°, 10.85±0.2°, 16.60±0.2°, 18.88±0.2° and 22.02±0.2° as measured by the X-ray powder diffraction using Cu—Kα radiation.

In some embodiments of the present invention, the crystal form B of 11-P4S has an X-ray powder diffraction pattern substantially as shown in FIG. 3-1 by Cu—Ka radiation.

In some embodiments of the present invention, the crystal form C of 11-P4S comprising characteristic peaks of 2θ diffraction angle at 5.81±0.2°, 6.33±0.2° and 12.86±0.2° as measured by the X-ray powder diffraction using Cu—Kα radiation.

In some embodiments of the present invention, the crystal form C of 11-P4S comprising characteristic peaks of 2θ diffraction angle at 5.81±0.2°, 6.33±0.2°, 7.99±0.2°, 12.86±0.2°, 19.09±0.2° and 23.17±0.2° as measured by the X-ray powder diffraction using Cu—Kα radiation.

In some embodiments of the present invention, the crystal form C of 11-P4S comprising characteristic peaks of 2θ diffraction angle at 5.81±0.2°, 6.33±0.2°, 7.99±0.2°, 10.31=0.2°, 11.63±0.2°, 12.86±0.2°, 18.16±0.2°, 19.09±0.2°, 23.17±0.2°, 24.00±0.2° and 27.32±0.2° as measured by the X-ray powder diffraction using Cu—Kα radiation.

In some embodiments of the present invention, the crystal form C of 11-P4S has an X-ray powder diffraction pattern substantially as shown in FIG. 4-1 by Cu—Ka radiation.

In some embodiments of the present invention, the crystal form D of 11-P4S comprising characteristic peaks of 2θ diffraction angle at 6.02±0.2° and 23.91±0.2° as measured by the X-ray powder diffraction using Cu—Kα radiation.

In some embodiments of the present invention, the crystal form D of 11-P4S comprising characteristic peaks of 2θ diffraction angle at 5.31±0.2°, 6.02±0.2°, 18.88±0.2°, 22.12±0.2° and 23.91±0.2° as measured by the X-ray powder diffraction using Cu—Kα radiation.

In some embodiments of the present invention, the crystal form D of 11-P4S has an X-ray powder diffraction pattern substantially as shown in FIG. 5-1 by Cu—Ka radiation.

In some embodiments of the present invention, the crystal form E of 11-P4S comprising characteristic peaks of 2θ diffraction angle at 6.06±0.2°, 18.32±0.2° and 30.79±0.2° as measured by the X-ray powder diffraction using Cu—Kα radiation.

In some embodiments of the present invention, the crystal form E of 11-P4S has an X-ray powder diffraction pattern substantially as shown in FIG. 6-1 by Cu—Ka radiation.

The present invention also provides the crystal form of p-toluenesulfonate of 19P2 (abbreviated as 19P2S) and the crystal form belongs to the orthorhombic system with a space group of P212121, and unit cell parameters of a=6.28880(10) Å, b=15.7958(3) Å, c=27.9234(6) Å, α=90°, β=90°, γ=90°, V=2773.82(9) Å3, and Z=4.

The present invention also provides a pharmaceutical composition comprising any one of the compounds above or a stereoisomer or pharmaceutically acceptable salt thereof, or the crystalline form of any one of the compounds above, and a pharmaceutically acceptable carrier. The pharmaceutical composition can be prepared into various pharmaceutically acceptable dosage forms, such as tablets, capsules, oral liquid preparations, granules, injections or various sustained and controlled release preparations. The pharmaceutical composition can be administered by oral administration or parenteral administration (such as intravenous, subcutaneous or topically). Dosage of administration can be appropriately adjusted according to the age, gender and disease type of the patients, and the daily dosage is generally about 10-100 mg/day.

The present invention also provides a use of any one of the compounds above or a stereoisomer or pharmaceutically acceptable salt thereof, or the crystalline form of any one of the compounds above, or a pharmaceutical composition in the preparation of a medicament for treating diseases related to VMAT2.

The present invention also provides a use of the compounds above or a stereoisomer or pharmaceutically acceptable salt thereof, or the crystalline form of any one of the compounds above, or a pharmaceutical composition in the preparation of a medicament for treating a hyperkinesis disorder; preferably, the hyperkinesis disorder comprises Huntington's disease, tardive dyskinesia, Tourette syndrome or convulsion.

The present invention also provides a method for preparing the compound of formula (II), the method comprises the following preparation steps:

Route 1

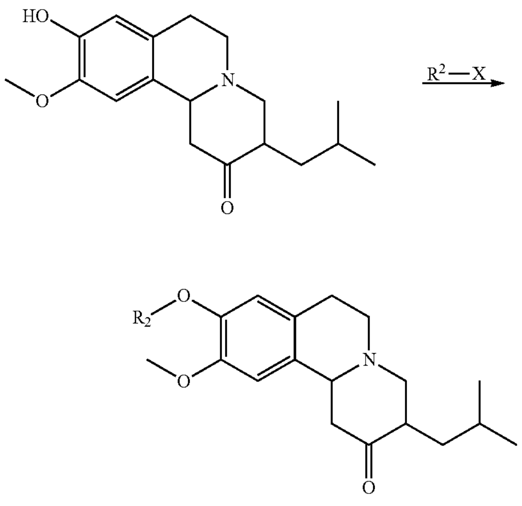

(II)

or

Route 2

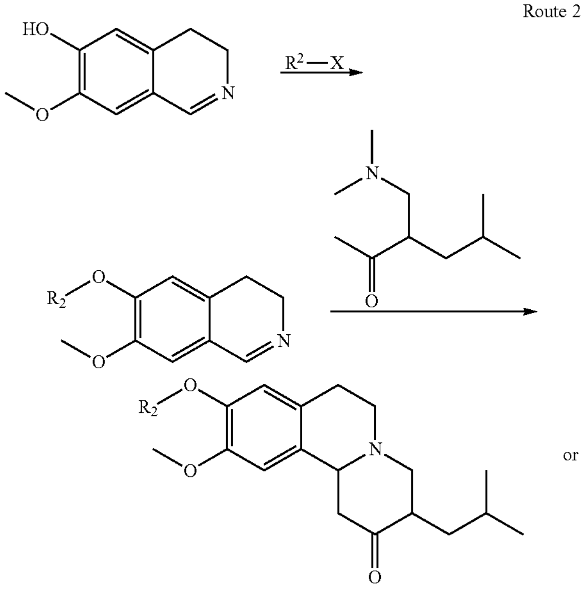

(II)

or

Route 3

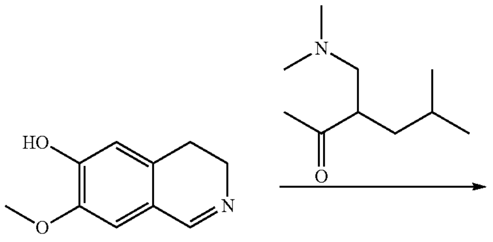

-continued

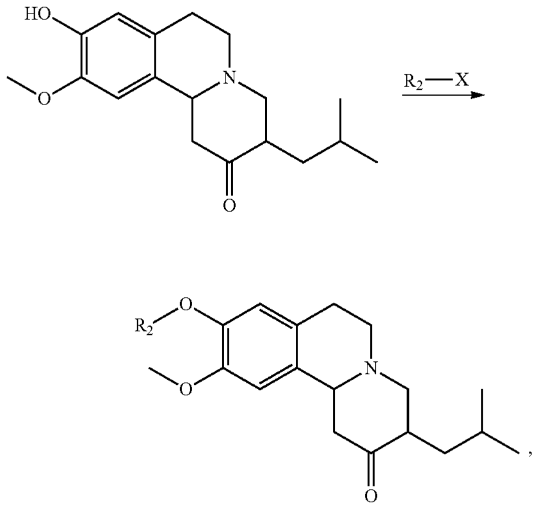

(II)

wherein X is a leaving group, $R_2$ has the same definition as in the compound of formula (II) above, $R_2$ preferably is ethyl, propyl, isobutyl, monofluorobutyl, monofluoropentyl, trifluoroethyl, trifluoropropyl, trifluorobutyl, trifluoropentyl, bisfluoroethyl or cyclopropanemethylene; more preferably is trifluoroethyl or cyclopropanemethylene.

The present invention also provides a method for preparing the compound of formula (III), the method comprises the following steps:

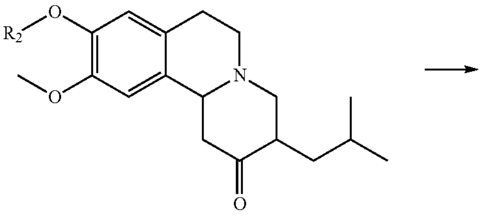

(II)

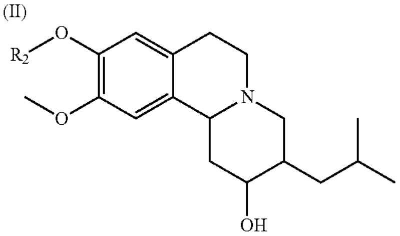

(III)

wherein sodium borohydride is used as the reducing agent, $R_2$ has the same definition as in the compound of formula (III) above, $R_2$ preferably is ethyl, propyl, isobutyl, monofluorobutyl, monofluoropentyl, trifluoroethyl, trifluoropropyl, trifluorobutyl, trifluoropentyl, bisfluoroethyl or cyclopropanemethylene; more preferably is trifluoroethyl or cyclopropanemethylene.

The present invention also provides a method for preparing the compound of formula (IV), the method comprises the following steps:

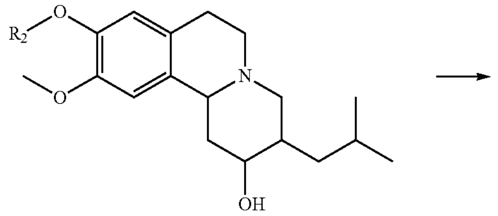

(III)

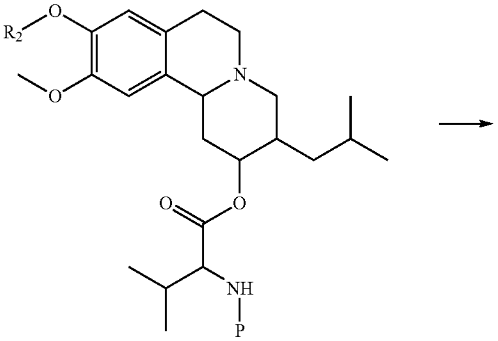

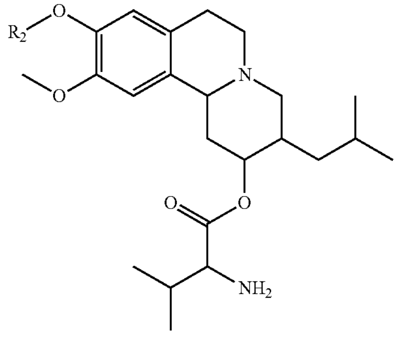

(IV)

wherein $R_2$ has the same definition as in the compound of formula (IV) above, $R_2$ preferably is ethyl, propyl, isobutyl, monofluorobutyl, monofluoropentyl, trifluoroethyl, trifluoropropyl, trifluorobutyl, trifluoropentyl, bisfluoroethyl or cyclopropanemethylene; more preferably is trifluoroethyl or cyclopropanemethylene. The group P is an amino protecting group, preferably is benzyloxycarbonyl (Cbz), tert-butoxycarbonyl (Boc), 9-fluorenylmethyloxycarbonyl (Fmoc), allyloxycarbonyl (Alloc), 2-(trimethylsilyl) ethoxycarbonyl (Teoc), etc. Common methods in the art can be used for the removal of protecting groups, and reference can be made to Protective Groups in Organic Synthesis, Third Edition, Author(s): Theodora W. Greene Ph.D., chapter 7 for details.

The present invention also provides a method for preparing the stereoisomer of the compound of formula (I), which specifically comprises as follows:

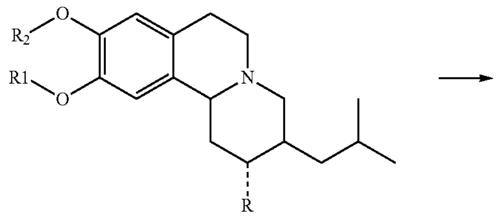

-continued

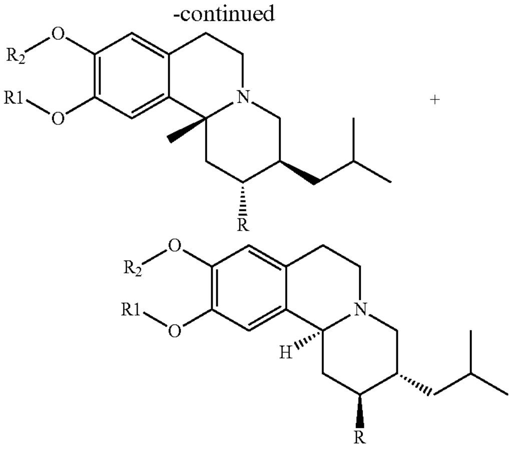

wherein R is —OH or

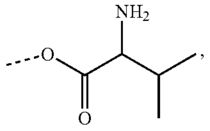

other variables have the same definition as in the compound of formula (I) above. The preparation method comprises resolution of the compound of formula (I) using a chiral chromatographic column, and the chiral chromatographic column is preferably Daicel CHIRALPAK AD-H chromatographic column.

The compounds provided in the present invention have any one or more of the following advantages: a strong affinity for VMAT2, higher exposure in vivo, higher concentration in brain, longer half-life and strong efficacies, etc.

Unless otherwise stated, the following terms and phrases used herein are intended to have the following meanings. A specific term or phrase should not be considered uncertain or unclear unless specifically defined, but should be understood in its ordinary meaning. When a trade name appears herein, it is intended to refer to the corresponding commodity or an active ingredient thereof.

The term "pharmaceutically acceptable" as used herein refers to compounds, materials, compositions and/or dosage forms, which are, within the scope of sound medical judgment, suitable for use in contact with human and animal tissues, without excessive toxicity, irritation, allergic reactions or other problems or complications, which is commensurate with a reasonable benefit/risk ratio.

The term "pharmaceutically acceptable salt" refers to a salt of the compound of the present invention, which is prepared from the compound having specific moiety in the present invention with relatively non-toxic acids or bases. When compounds of the present invention contain relatively acidic functional groups, base addition salts can be obtained by contacting the neutral form of such compounds with a sufficient amount of base, either in pure solution or a suitable inert solvent. Pharmaceutically acceptable base addition salts include sodium, potassium, calcium, ammonium, organic amino or magnesium salts or similar salts. When compounds of the present invention contain relatively basic functional groups, acid addition salts can be obtained by contacting the neutral form of such compounds with a sufficient amount of acid, either in pure solution or a suitable inert solvent. Examples of pharmaceutically acceptable acid addition salts include inorganic acid salts or organic acid salts. Certain specific compounds of the present invention contain basic and acidic functional groups and thus can be converted to any base or acid addition salt.

The pharmaceutically acceptable salts of the present invention can be synthesized from a parent compound containing free acids or free bases by conventional chemical methods. In general, the method for preparing such salts comprises: in water or an organic solvent or a mixture of both, reacting these compounds in free acid or base forms with a stoichiometric amount of a suitable base or acid to prepare the salts.

The compounds of the present invention may exist in specific geometric isomers or stereoisomeric isomers. The present invention contemplates all such isomers, including cis and trans isomers, (−)- and (+)-enantiomers, (R)- and (S)-enantiomers, diastereomers, (D)-isomers, (L)-isomers, and racemic mixtures and other mixtures thereof, such as enantiomerically or diastereomerically enriched mixtures, all of which fall within the scope of the present invention. Additional asymmetric carbon atoms may be present in a substituent such as an alkyl group. All these isomers and mixtures thereof are included in the scope of the present invention.

Unless otherwise stated, the term "enantiomer" refers to stereoisomers that are mirror images of each other.

Unless otherwise stated, the term "diastereomers" refers to stereoisomers in which molecules have two or more chiral centers and are not mirror images of each other.

Unless otherwise stated, "(D)" or "(+)" means dextrorotatory, "(L)" or "(−)" means levorotatory, and "(DL)" or "(±)" means racemic.

Unless otherwise stated, the wedge-shaped solid bond ( ) and the wedge-shaped dotted bond ( ) represent the absolute configuration of a stereoscopic center.

Optically active (R)- and (S)-isomers and D and L isomers can be prepared using chiral synthesis or chiral reagents or other conventional techniques. If a particular enantiomer of a compound of the present invention is desired, it can be prepared by asymmetric synthesis or derivatization with a chiral auxiliary, wherein the resulting diastereomeric mixture is separated and the auxiliary groups are cleaved to provide pure desired enantiomers. Alternatively, where the molecule contains a basic functional group (such as an amino group) or an acidic functional group (such as a carboxyl group), diastereomeric salts can be formed with an appropriate optically active acid or base, followed by resolution of the diastereomers using conventional methods well known in the art, and subsequent recovery of the pure enantiomers. In addition, separation of enantiomers and diastereomers is frequently accomplished by using chromatography, which uses chiral stationary phases, optionally in combination with chemical derivatization methods (e.g., formation of carbamates from amines). The compounds of the present invention may contain unnatural proportions of atomic isotopes at one or more of the atoms constituting the compound. For example, the compounds may be radiolabeled with radioactive isotopes, such as tritium (3H), iodine-125 (125I) or C-14 (14C). For another example, the hydrogen can be substituted by heavy hydrogen to form deuterated drugs. The bond formed by deuterium and carbon is stronger than the bond formed by ordinary hydrogen and carbon. Compared with undeuterated drugs, deuterated drugs have reduced toxic side effects, increased drug stability, enhanced efficacy, prolonged biological half-life of drugs and other advantages. All isotopic variations of the compounds of the present invention, whether radioactive or not, are intended to be encompassed within the scope of the present invention.

BRIEF DESCRIPTION OF THE DRAWINGS

FIGS. 2-1, 2-2 and 2-3: XRPD pattern, TGA/DSC pattern, $^1$H NMR spectra of crystal form A of compound 11-P4S, respectively FIGS. 3-1, 3-2 and 3-3: XRPD pattern, TGA/DSC pattern, $^1$H NMR spectra of crystal form B of compound 11-P4S, respectively FIGS. 4-1, 4-2 and 4-3: XRPD pattern, TGA/DSC pattern, $^1$H NMR spectra of crystal form C of compound 11-P4S, respectively FIGS. 5-1, 5-2 and 5-3: XRPD pattern, TGA/DSC pattern, $^1$H NMR spectra of crystal form D of compound 11-P4S, respectively FIGS. 6-1, 6-2 and 6-3: XRPD pattern, TGA/DSC pattern, $^1$H NMR spectra of crystal form E of compound 11-P4S, respectively

DETAILED DESCRIPTION OF EMBODIMENTS

Example 1

Figure 1:
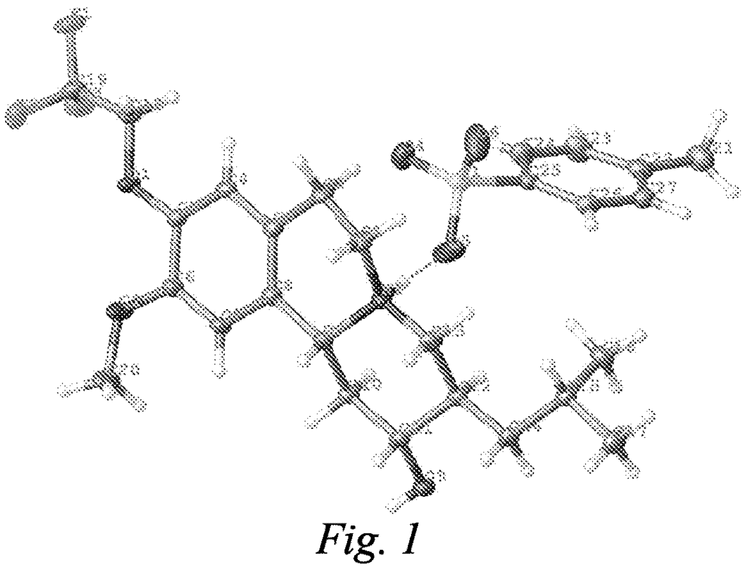
FIG. 1: ellipsoidal graph of molecular structure of compound 11-P4S

Preparation of Fragment 1:

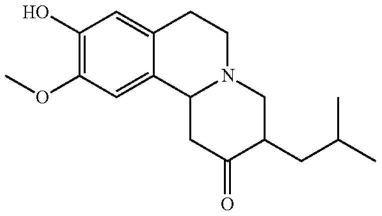

Fragment 1

Synthetic Route:

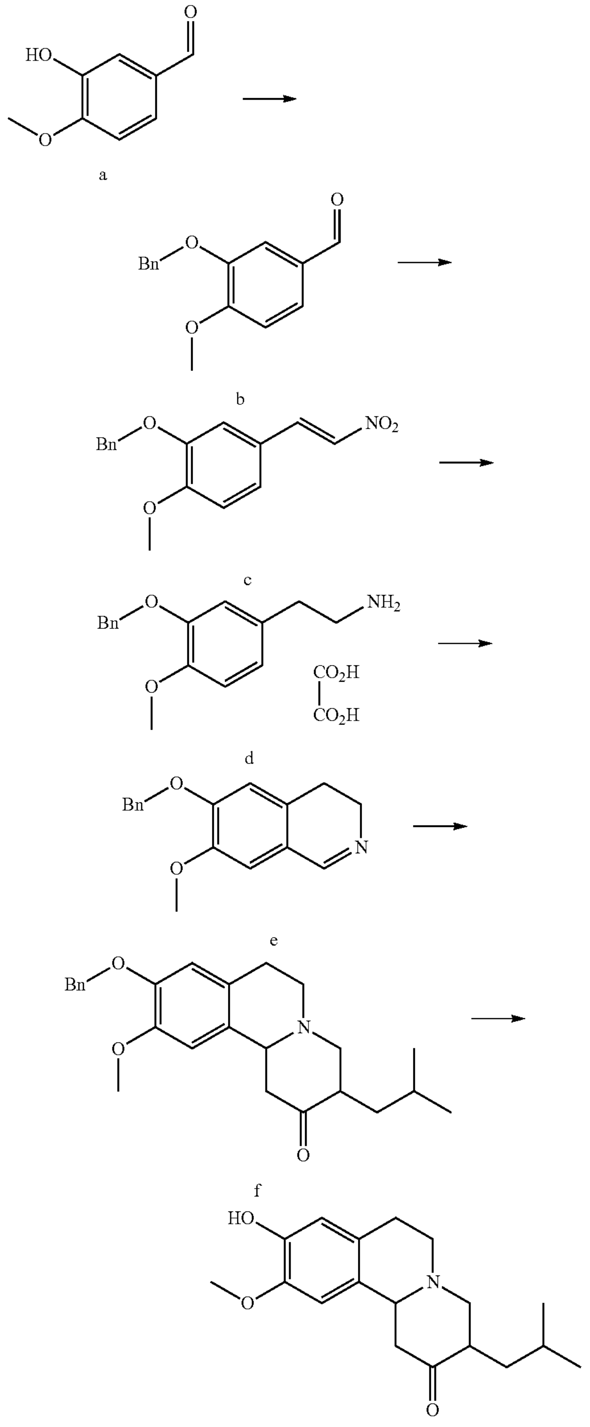

a b c d e f

Fragment 1

1. Compound a (5.0 g, 32.9 mmol) was dissolved in DMF (50 mL). Benzyl bromide (6.2 g, 35.8 mmol) and potassium carbonate (6.8 g, 49.1 mmol) were added. The reaction mixture was reacted at room temperature overnight with stirring. Water (100 mL) was added to the reaction system. A solid was precipitated and suction filtration was performed to afford 7.2 g of a white solid b.

2. Compound b (5.4 g, 22.3 mmol) was dissolved in nitromethane (50 mL). Ammonium acetate (0.86 g, 11.2 mmol) was added and the reaction mixture was heated to 110° C. and reacted for 3 h with stirring. The reaction system was cooled to room temperature. Water (100 mL) was added to the reaction system. A solid was precipitated and suction filtration was performed to afford a yellow solid c (6.0 g).

3. Under the protection of nitrogen, lithium aluminum hydride (2.0 g, 52.6 mmol) was slowly added to anhydrous tetrahydrofuran (50 mL). The reaction mixture was cooled to 0° C. The c (5.0 g, 17.5 mmol) was slowly added dropwise. Then the reaction system was warmed up to 60° C. and reacted for 2 h with stirring. The reaction mixture was cooled to 0° C., and the reaction was quenched with water. The resulting mixture was suction filtered and the filtrate was dried over anhydrous sodium sulfate and concentrated under reduced pressure to afford 3.2 g of a light yellow oily liquid d. The product was directly used in the next step of reaction without purification. MS m/z (ESI): 258.2 [M+1]

4. Crude d (2.7 g, 10.5 mmol) was dissolved in glacial acetic acid (16 mL). Trifluoroacetic acid (4 mL) was added and then urotropine (3.0 g, 21.0 mmol) was added. The reaction mixture was warmed to 80° C. and reacted for 2 h with stirring. The reaction mixture was cooled to room temperature. Crushed ice (50 g) was added and then the pH of the reaction mixture was adjusted to 8 with 20% sodium hydroxide solution. The reaction solution was extracted with dichloromethane (50 mL*3). The organic phases were combined, dried over anhydrous sodium sulfate and filtered. The filtrate was concentrated under reduced pressure to afford 2.4 g of a crude product e. The product was directly used in the next step of reaction without purification. MS m/z (ESI): 268.1 [M+1]

5. Crude e (2.0 g, 5.1 mmol) was dissolved in a system of ethanol (20 mL) and water (20 mL). Benzyltriethyl ammonium chloride (0.43 g, 1.3 mmol) was added and the mixture was heated to reflux and reacted for 5 h with stirring. The solvent was evaporated under reduced pressure. Water (50 mL) was added to the residue and extracted with ethyl acetate (20 mL*3). The organic phases were combined, dried over anhydrous sodium sulfate and filtered. The filtrate was concentrated under reduced pressure to afford a crude product. Then the crude product was recrystallized with ethanol to afford 0.8 g of a white solid compound f. MS m/z (ESI): 394.2 $[M+H]^+$; $^1H$ NMR (600 MHz, $CDCl_3$): δ7.43-7.28 (m, 5H), 6.64 (s, 1H), 6.57 (s, 1H), 5.11 (s, 2H), 3.82 (s, 3H), 3.48 (dd, 1H), 3.26 (dd, 1H), 3.13-3.00 (m, 2H), 2.90 (dd, 1H), 2.77-2.61 (m, 2H), 2.60-2.48 (m, 2H), 2.33 (t, 1H), 1.83-1.75 (m, 1H), 1.70-1.58 (m, 1H), 1.06-0.98 (m, 1H), 0.90 (m, 6H).

6. Compound f (0.5 g, 1.3 mmol) was dissolved in methanol (20 mL). Palladium on carbon (0.05 g) was added and the resulting mixture was stirred at room temperature for 8 h under a hydrogen atmosphere. Palladium on carbon was removed by filtration and the solvent was evaporated from the filtrate under reduced pressure to afford 0.47 g of a light yellow powder, i.e., fragment 1. MS m/z (ESI): 304.2 [M+1].

Preparation of Compound 1:

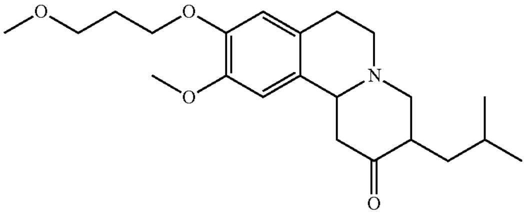

Compound 1

Synthetic Route:

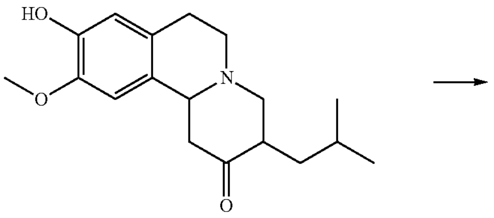

Fragment 1

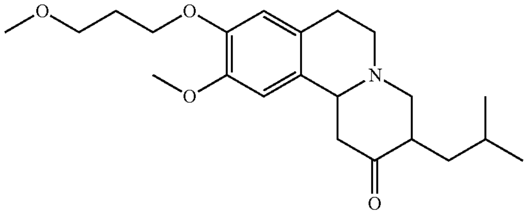

1

Fragment 1 compound (150 mg, 0.50 mmol) was dissolved in DMF (2 mL).

3-Bromopropylmethyl ether (84 mg, 0.55 mmol) and potassium carbonate (103 mg, 0.75 mmol) were added and the mixture was warmed to 60° C. and reacted for 5 h with stirring. After cooling, water (8 mL) was added into the reaction system and then the reaction mixture was extracted with ethyl acetate (10 mL*3). The organic phases were combined, dried over anhydrous sodium sulfate and filtered. The filtrate was concentrated under reduced pressure and separated by column chromatography (petroleum ether:ethyl acetate=3:1) to afford compound 1 (120 mg, light yellow waxy solid). MS m/z (ESI): 376.2 $[M+H]^+$; $^1H$ NMR (600 MHz, $CDCl_3$): δ6.65 (s, 1H), 6.54 (s, 1H), 4.07 (t, 2H), 3.80 (s, 3H), 3.55 (t, 2H), 3.48 (dd, 1H), 3.34 (s, 3H), 3.26 (dd, 1H), 3.15-3.02 (m, 2H), 2.88 (dd, 1H), 2.77-2.61 (m, 2H), 2.60-2.48 (m, 2H), 2.33 (t, 1H), 2.11-2.04 (m, 2H), 1.83-1.75 (m, 1H), 1.70-1.58 (m, 1H), 1.06-0.98 (m, 1H), 0.90 (m, 6H).

Example 2

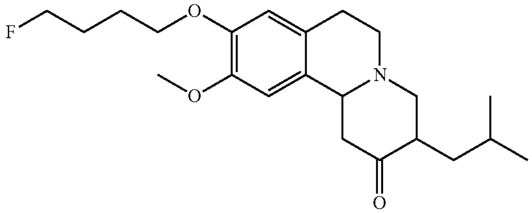

Compound 2

Synthetic Route:

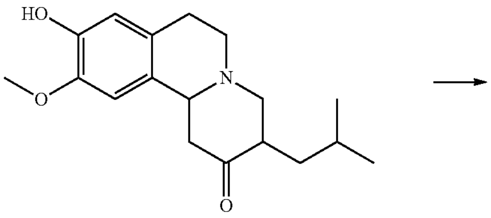

Fragment 1

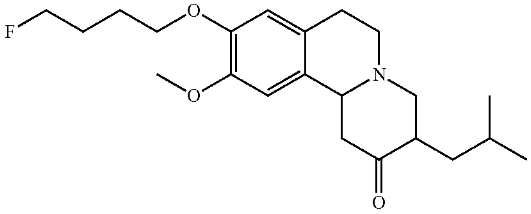

2

Fragment 1 compound (150 mg, 0.50 mmol) was dissolved in DMF (2 mL). 1-Bromo-4-fluorobutane (85 mg, 0.55 mmol) and potassium carbonate (103 mg, 0.75 mmol) were added and the mixture was warmed to 60° C. and reacted for 5 h with stirring. After cooling, water (8 mL) was added into the reaction system and then the reaction mixture was extracted with ethyl acetate (10 mL*3). The organic phases were combined, dried over anhydrous sodium sulfate and filtered. The filtrate was concentrated under reduced pressure and separated by column chromatography (petroleum ether:ethyl acetate=3:1) to afford compound 2 (115 mg, light yellow oily liquid). MS m/z (ESI): 378.2 $[M+H]^+$; $^1H$ NMR (600 MHz, $CDCl_3$): δ6.64 (s, 1H), 6.54 (s, 1H), 4.57 (t, 1H), 4.45 (t, 1H), 4.07 (t, 2H), 3.80 (s, 3H), 3.48 (dd, 1H), 3.26 (dd, 1H), 3.15-3.02 (m, 2H), 2.88 (dd, 1H), 2.77-2.61 (m, 2H), 2.60-2.48 (m, 2H), 2.33 (t, 1H), 1.96-1.90 (m, 3H), 1.88-1.75 (m, 2H), 1.70-1.58 (m, 1H), 1.06-0.98 (m, 1H), 0.89 (m, 6H).

Example 3

Compound 3

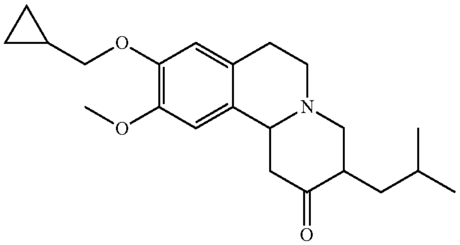

Synthetic Route:

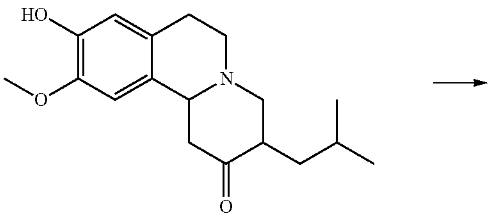

Fragment 1

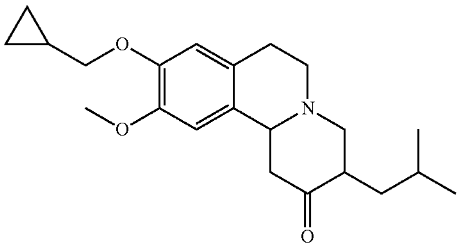

3

Fragment 1 compound (150 mg, 0.50 mmol) was dissolved in DMF (2 mL). Bromomethylcyclopropane (74 mg, 0.55 mmol) and potassium carbonate (103 mg, 0.75 mmol) were added and the mixture was warmed to 60° C. and reacted for 5 h with stirring. After cooling, water (8 mL) was added into the reaction system and then the reaction mixture was extracted with ethyl acetate (10 mL*3). The organic phases were combined, dried over anhydrous sodium sulfate and filtered. The filtrate was concentrated under reduced pressure and separated by column chromatography (petroleum ether:ethyl acetate=3:1) to afford compound 3 (107 mg, light yellow waxy solid). MS m/z (ESI): 358.2 $[M+H]^+$; $^1H$ NMR (600 MHz, $CDCl_3$): δ6.61 (s, 1H), 6.54 (s, 1H), 3.82-3.79 (m, 5H), 3.48 (dd, 1H), 3.28 (dd, 1H), 3.15-3.02 (m, 2H), 2.89 (dd, 1H), 2.77-2.61 (m, 2H), 2.60-2.48 (m, 2H), 2.33 (t, 1H), 1.82-1.75 (m, 1H), 1.70-1.58 (m, 1H), 1.06-0.98 (m, 1H), 0.89 (m, 6H), 0.65-0.59 (m, 2H), 0.35-0.30 (m, 2H).

Example 4

Compound 4

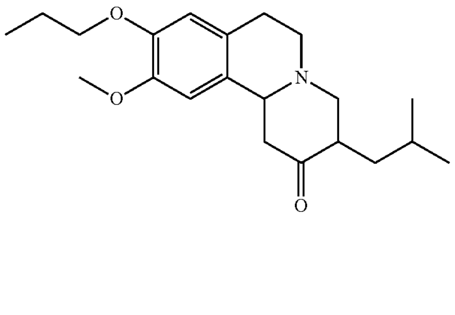

Synthetic Route:

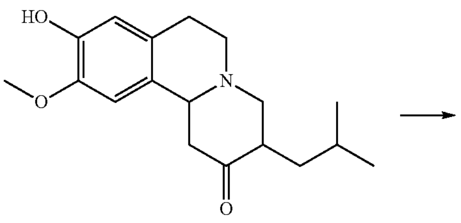

Fragment 1

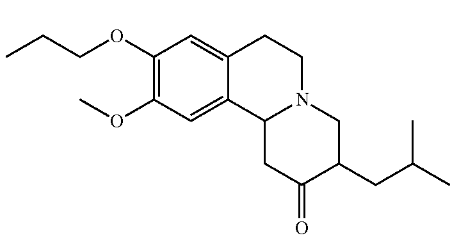

4

Fragment 1 compound was dissolved in DMF (2 mL). Bromopropane (68 mg, 0.55 mmol) and potassium carbonate (103 mg, 0.75 mmol) were added and the mixture was warmed to 60° C. and reacted for 5 h with stirring. After cooling, water (8 mL) was added into the reaction system and then the reaction mixture was extracted with ethyl acetate (10 mL*3). The organic phases were combined, dried over anhydrous sodium sulfate and filtered. The filtrate was concentrated under reduced pressure and separated by column chromatography (petroleum ether:ethyl acetate=3:1) to afford compound 4 (102 mg, light yellow waxy solid). MS m/z (ESI): 346.2 $[M+H]^+$; $^1H$ NMR (600 MHz, $CDCl_3$): δ 6.64 (s, 1H), 6.54 (s, 1H), 33.96-3.90 (t, 2H), 3.81 (s, 3H), 3.49 (dd, 1H), 3.27 (dd, 1H), 3.15-3.02 (m, 2H), 2.88 (dd, 1H), 2.74-2.66 (m, 2H), 2.62-2.48 (m, 2H), 2.33 (t, 1H), 1.96-1.90 (m, 3H), 1.70-1.58 (m, 1H), 1.06-0.98 (m, 4H), 0.89 (m, 6H).

Example 5

Compound 5

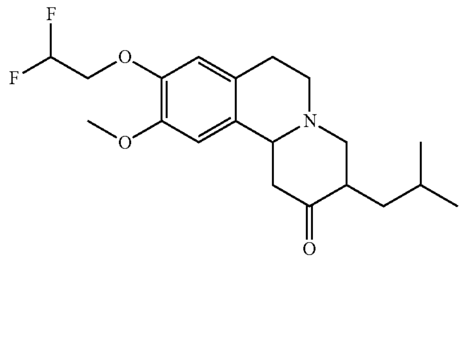

Synthetic Route:

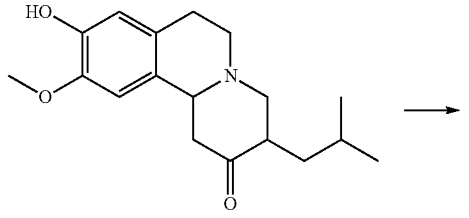

Fragment 1

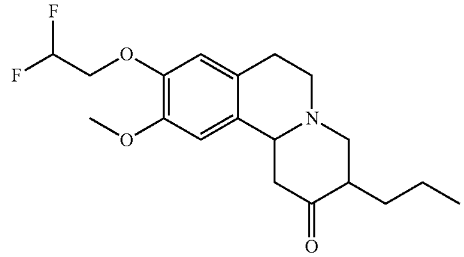

5

In a 20 mL microwave tube, fragment 1 compound (606 mg, 2.0 mmol) was dissolved in DMF (6 mL). 1,1,-Difluoro-2-iodoethane (768 mg, 4.0 mmol) and potassium carbonate (1.10 g, 8.0 mmol) were added. The mixture was warmed to 100° C. and reacted for 3 h. After cooling, the reaction system was poured into water (30 mL) and then extracted with ethyl acetate (10 mL*3). The organic phases were combined, dried over anhydrous sodium sulfate and filtered. The filtrate was concentrated under reduced pressure and separated by column chromatography (petroleum ether:ethyl acetate=4:1) to afford compound 5 (600 mg, off-white solid). MS m/z (ESI): 368.2 $[M+H]^+$; $^1H$ NMR (400 MHz, $CDCl_3$): δ 6.68 (s, 1H), 6.59 (s, 1H), 5.97-6.24 (m, 1H), 4.16-4.23 (m, 2H), 3.82 (s, 3H), 3.42-3.52 (m, 1H), 3.16-3.31 (m, 1H), 2.54-3.12 (m, 7H), 2.32-2.38 (m, 1H), 1.63-1.71 (m, 1H), 1.00-1.07 (m, 1H), 0.88-0.92 (m, 6H).

Example 6

Compound 6

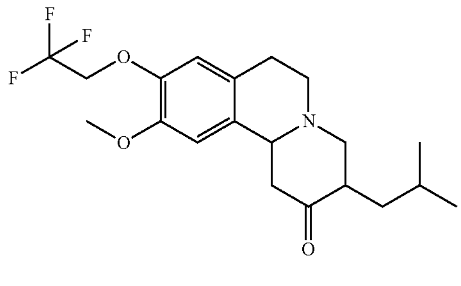

Synthetic Route 1:

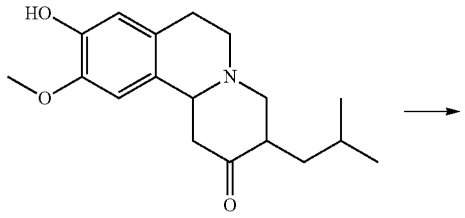

Fragment 1

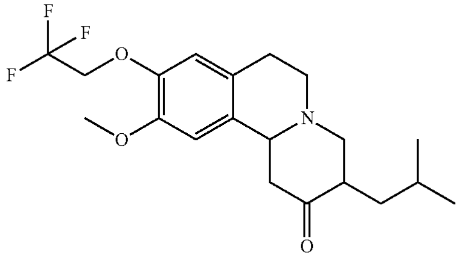

6

In a 20 mL microwave tube, fragment 1 compound (1.82 g, 6.0 mmol) was dissolved in DMF (15 mL). 1,1,1-Trifluoro-2-iodoethane (2.30 g, 12 mmol) and potassium carbonate (3.31 g, 24 mmol) were added. The mixture was warmed to 140° C. and reacted for 3 h. After cooling, the reaction system was poured into 75 mL water and then extracted with ethyl acetate (15 mL*3). The organic phases were combined, dried over anhydrous sodium sulfate and filtered. The filtrate was concentrated under reduced pressure and separated by column chromatography (petroleum ether:ethyl acetate=4:1) to afford compound 6 (610 mg, off-white solid). MS m/z (ESI): 386.2 $[M+H]^+$; $^1H$ NMR (400 MHz, $CDCl_3$) δ 6.75 (s, 1H), 6.60 (s, 1H), 4.35-4.39 (m, 2H), 3.82 (s, 3H), 3.49-3.53 (m, 1H), 3.26-3.31 (m, 1H), 2.38-3.15 (m, 7H), 2.32-2.35 (m, 1H), 1.37-1.84 (m, 2H), 1.00-1.08 (m, 1H), 0.90-0.92 (m, 6H).

Synthetic Route 2:

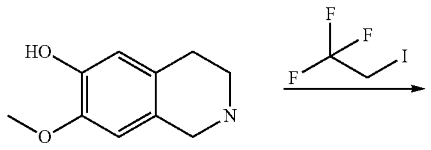

Reactant I

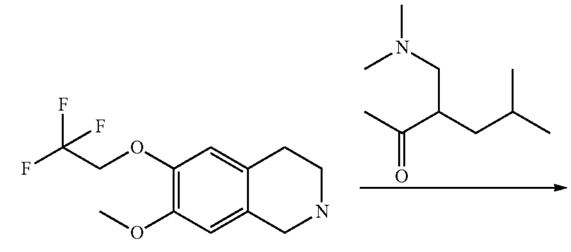

Intermediate 1

-continued

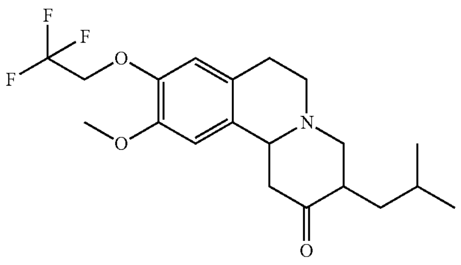

6

Step 1: Reactant I (50 mg, 0.28 mmol) was dissolved in DMF (1 mL). $K_2CO_3$ (77 mg, 0.56 mmol) was added and the mixture was reacted at room temperature for 0.5 h with stirring. Trifluoroiodoethane (76 mg, 0.36 mmol) was added and the mixture was reacted at 80° C. overnight with stirring until TLC detection showed that the reaction was complete. Water was added to quench the reaction. A solid was precipitated while stirring was carried out for 1 h, which was followed by suction filtration. The filter cake was washed with water twice. The filter cake was collected and dried to afford 0.07 g of intermediate 1 as a yellowish solid.

Step 2: Intermediate 1 (0.07 g, 0.270 mmol) was dissolved in a mixed solution of ethanol (1 mL) and water (1 mL). 3-Dimethylamino-5-methyl-2-hexanone (0.06 g, 0.324 mmol) and benzyltriethyl ammonium chloride (0.02 g, 0.081 mmol) were added. The mixture was heated to 95° C. and reacted for 18 h. The reaction mixture was cooled to room temperature and concentrated. The residue was extracted with ethyl acetate (20 mL*3). The organic phases were combined, dried over anhydrous sodium sulfate, filtered, concentrated under reduced pressure, and separated by column chromatography (petroleum ether: ethyl acetate=5:1) to afford compound 6 (10 mg, off-white solid), with a yield of 10%.

Synthetic Route 3:

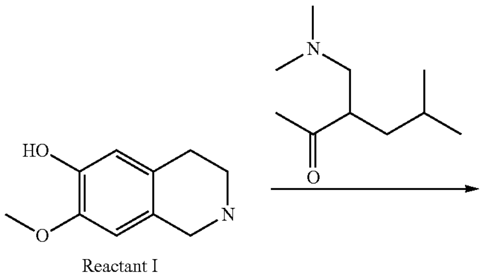

Reactant I

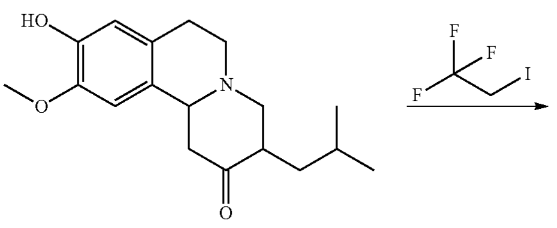

Fragment 1

-continued

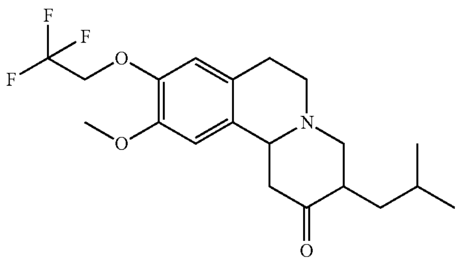

6

Step 1: Reactant I (50 mg, 0.282 mmol) was dissolved in a mixed solution of ethanol (1 mL) and water (1 mL). 3-Dimethylamino-5-methyl-2-hexanone (0.06 g, 0.338 mmol) and benzyltriethyl ammonium chloride (0.02 g, 0.085 mmol) were added. The mixture was heated to 95° C. and reacted for 18 h. The reaction mixture was cooled to room temperature and concentrated. The residue was extracted with ethyl acetate (20 mL*3). The organic phases were combined, dried over anhydrous sodium sulfate, filtered, concentrated under reduced pressure and separated by column chromatography (petroleum ether:ethyl acetate=5:1) to afford fragment 1 (70 mg, off-white solid), with a yield of 82%.

Step 2: Same as synthetic route 1.

Example 7

Compound 7

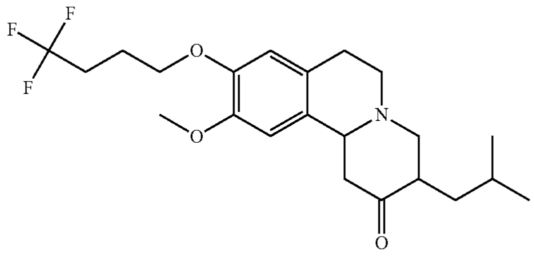

Synthetic Route:

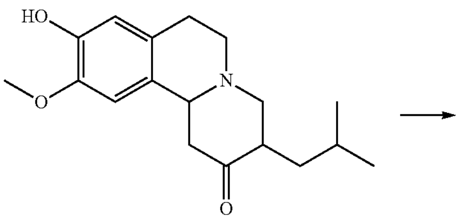

Fragment 1

-continued

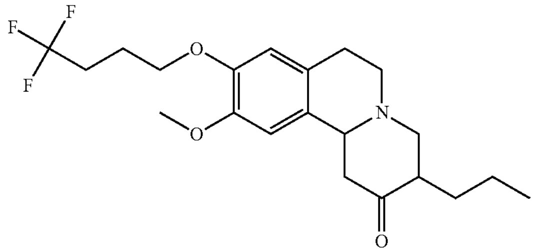

7

Fragment 1 compound (606 mg, 2.0 mmol) was dissolved in DMF (6 mL). 1-Bromo-4,4,4-trifluorobutane (573 mg, 3.0 mmol) and potassium carbonate (828 mg, 6.0 mmol) were added. The mixture was warmed to 80° C. and reacted for 5 h. After cooling, the reaction system was poured into water (30 mL) and then extracted with ethyl acetate (10 mL*3). The organic phases were combined, dried over anhydrous sodium sulfate and filtered. The filtrate was concentrated under reduced pressure and separated by column chromatography (petroleum ether:ethyl acetate=4:1) to afford compound 7 (480 mg, off-white solid). MS m/z (ESI): 414.2 $[M+H]^+$; $^1H$ NMR (400 MHz, $CDCl_3$) δ 6.62 (s, 1H), 6.56 (s, 1H), 4.03-4.05 (m, 2H), 3.81 (s, 3H), 3.49-3.51 (m, 1H), 3.21-3.42 (m, 1H), 2.54-3.14 (m, 7H), 2.29-2.37 (m, 3H), 2.05-2.09 (m, 2H), 1.68-1.83 (m, 1H), 1.64-1.68 (m, 1H), 1.01-1.06 (m, 1H), 0.90-0.92 (m, 6H).

Example 8

Compound 8

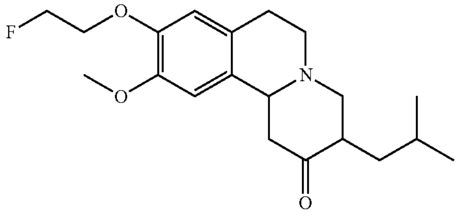

Synthetic Route:

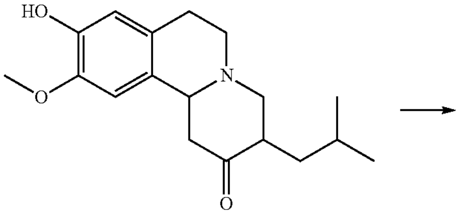

Fragment 1

-continued

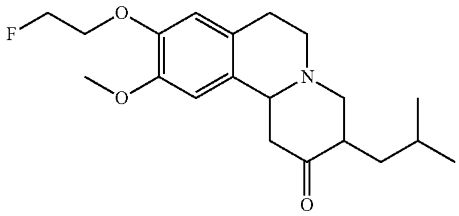

8

Fragment 1 compound (100 mg, 0.33 mmol) was dissolved in 1 mL DMF. 1-Bromo-2-fluoroethane (62.7 mg, 0.5 mmol) and potassium carbonate (138 mg, 1 mmol) were added. The mixture was warmed to 80° C. and reacted for 5 h. After cooling, the reaction system was poured into water (5 mL) and then extracted with ethyl acetate (2 mL*3). The organic phases were combined, dried over anhydrous sodium sulfate and filtered. The filtrate was concentrated under reduced pressure and separated by column chromatography (dichloromethane:methanol=80:1) to afford compound 8 (75 mg, off-white solid). MS m/z (ESI): 350.2 $[M+H]^+$; $^1H$ NMR (400 MHz, $CDCl_3$) δ 6.68 (s, 1H), 6.57 (s, 1H), 4.72-4.81 (m, 2H), 4.22-4.28 (m, 2H), 3.82 (s, 3H), 2.29-3.58 (m, 10H), 1.64-1.83 (m, 2H), 1.02-1.06 (m, 1H), 0.90-0.93 (m, 6H).

Example 9

Compound 9

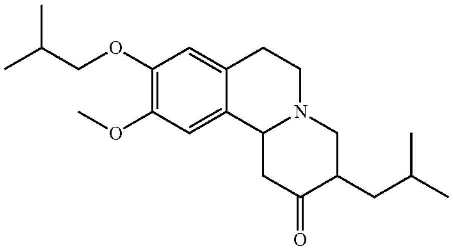

Synthetic Route:

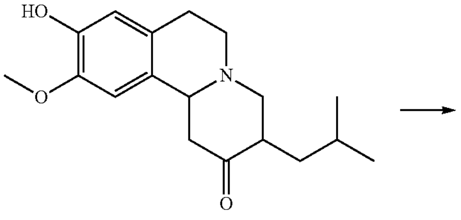

Fragment 1

-continued

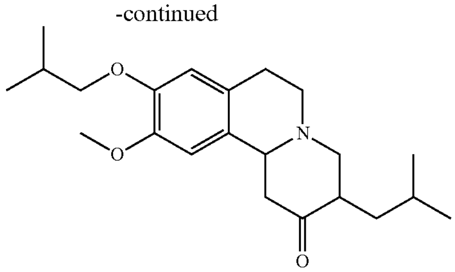

9

Fragment 1 compound (606 mg, 2.0 mmol) was dissolved in DMF (6 mL). Bromo-isobutane (411 mg, 3.0 mmol) and potassium carbonate (828 mg, 6.0 mmol) were added. The mixture was warmed to 80° C. and reacted for 5 h. After cooling, the reaction system was poured into water (30 mL) and then extracted with ethyl acetate (10 mL*3). The organic phases were combined, dried over anhydrous sodium sulfate and filtered. The filtrate was concentrated under reduced pressure and separated by column chromatography (petroleum ether:ethyl acetate=4:1) to afford compound 9 (410 mg, off-white solid). MS m/z (ESI): 360.2 $[M+H]^+$; $^1H$ NMR (400 MHz, $CDCl_3$) δ 6.62 (s, 1H), 6.55 (s, 1H), 3.83 (s, 3H), 3.70-3.80 (m, 2H), 2.35-3.50 (m, 10H), 2.11-2.18 (m, 1H), 1.78-1.83 (m, 1H), 1.64-1.69 (m, 1H), 1.02-1.06 (m, 7H), 0.90-0.92 (m, 6H).

Example 10

Compound 10

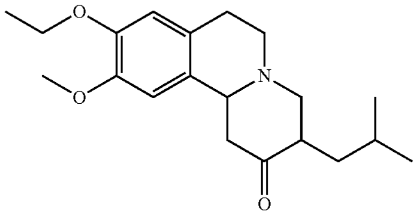

Synthetic Route:

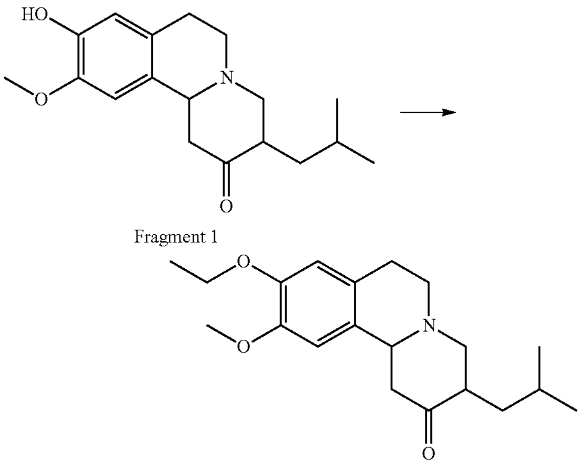

Fragment 1

10

Fragment 1 compound (606 mg, 2.00 mmol) was dissolved in DMF (6 mL). Bromoethane (327 mg, 3.00 mmol) and potassium carbonate (414 mg, 3.0 mmol) were added. The mixture was warmed to 80° C. and reacted for 5 h. After cooling, the reaction system was poured into water (30 mL) and then extracted with ethyl acetate (20 mL*3). The organic phases were combined, dried over anhydrous sodium sulfate and filtered. The filtrate was concentrated under reduced pressure and separated by column chromatography (petroleum ether:ethyl acetate=4:1) to afford compound 10 (397 mg, off-white solid). MS m/z (ESI): 332.2 $[M+H]^+$;

Example 11

Compound 11

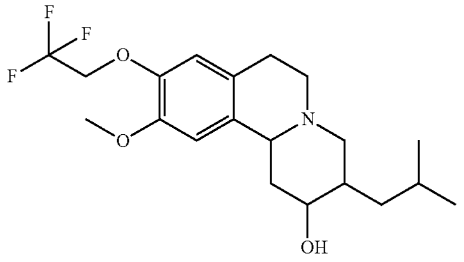

Synthetic Route:

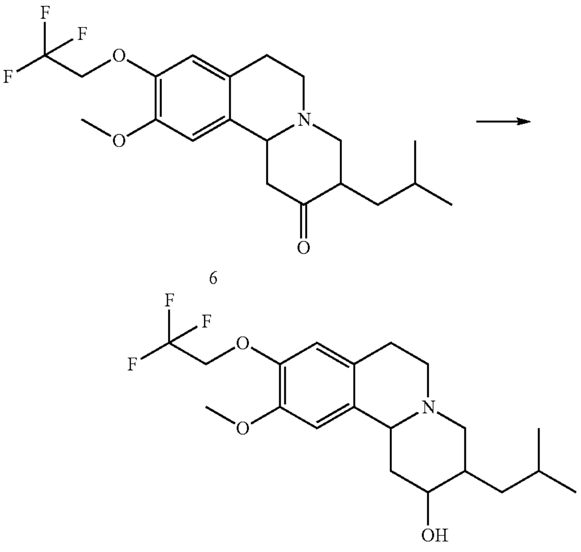

6

11

Under the protection of nitrogen, compound 6 (610 mg, 1.58 mmol) was dissolved in THF (10 mL) under ice-bath. Sodium borohydride (120 mg, 3.17 mmol) and MeOH (10 mL) were added and the mixture was reacted under ice-bath for 2 h. The reaction was quenched by adding 1N hydrochloric acid. Aqueous $NaHCO_3$ solution was added to adjust the pH value to alkaline. The organic phase was concentrated and then extracted with ethyl acetate (10 mL*3). The organic phases were combined, dried over anhydrous sodium sulfate and filtered. The organic phase was concentrated under reduced pressure and separated by column chromatography (dichloromethane:methanol=40:1) to afford compound 11 (346 mg, off-white solid), with a yield of 56.5%. MS m/z (ESI): 388.2 $[M+H]^+$; $^1H$ NMR (400 MHz, $CD_3OD$) δ 6.87 (s, 1H), 6.79 (s, 1H), 4.43-4.49 (m, 2H), 3.85 (s, 3H), 2.93-3.24 (m, 4H), 2.44-2.71 (m, 3H), 1.02-2.10 (m, 7H), 0.94-1.02 (m, 6H).

Examples 12-20

Examples 12-20 were synthesized by using a method analogous to that of Example 11.

TABLE 1

Structure and characterization data of compounds of Examples 12-20

| Examples | Structural formula | Spectra |
|---|---|---|
| 12 | 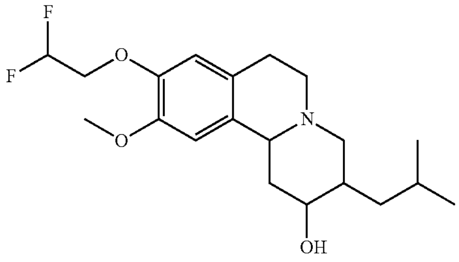 | MS m/z (ESI): 370.2 $[M + H]^+$<br>$^1H$ NMR (400 MHz, $CD_3OD$): δ 6.84 (s, 1H), 6.76 (s, 1H), 6.01-6.31 (m, 1H), 4.15-4.23 (m, 2H), 3.83 (s, 3H), 3.24-3.26 (m, 1H), 2.93-3.12 (m, 3H), 2.49-2.75 (m, 3H), 1.93-2.18 (m, 1H), 1.26-1.78 (m, 6H), 1.02-1.17 (m, 1H), 0.94-0.98 (m, 6H). |
| 13 | 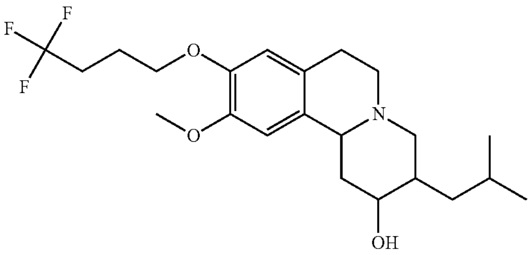 | MS m/z (ESI): 416.2 $[M + H]^+$<br>$^1H$ NMR (400 MHz, $CD_3OD$): δ 6.84 (s, 1H), 6.75 (s, 1H), 4.04-4.08 (m, 2H), 3.39-3.55 (m, 1H), 3.09-3.21 (m, 2H), 1.88-2.79 (m, 7H), 1.02-2.10 (m, 7H), 0.94-1.02 (m, 6H), 1.04-1.67 (m, 5H), 0.95-0.99 (m, 6H). |
| 14 | 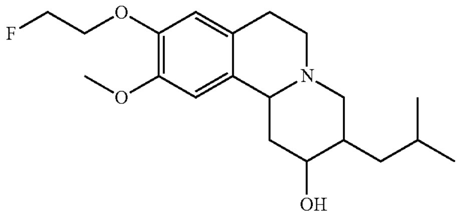 [SMILES: COc1cc2c(cc1OCCF)CCN1CC(CC(C)C)C(O)CC21] | MS m/z (ESI): 352.2 $[M + H]^+$<br>$^1H$ NMR (600 MHz, $CDCl_3$): δ 6.70 (s, 1H), 6.63 (s, 1H), 4.67-4.87 (m, 2H), 4.17-4.34 (m, 2H), 3.83 (s, 3H), 3.33-3.46 (m, 1H), 2.93-3.21 (m, 4H), 2.51-2.74 (m, 2H), 2.38-2.51 (m, 1H), 1.93-2.03 (m, 1H), 1.66-1.76 (m, 2H), 1.54-1.65 (m, 2H), 1.44-1.53 (m, 1H), 1.02-1.09 (m, 1H), 0.89-0.97 (m, 6H). |
| 15 | 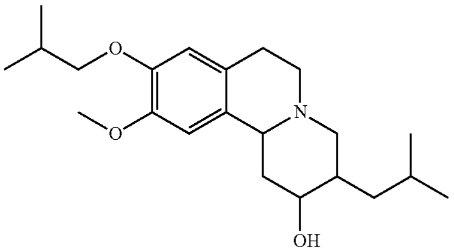 [SMILES: COc1cc2c(cc1OCC(C)C)CCN1CC(CC(C)C)C(O)CC21] | MS m/z (ESI): 362.2 $[M + H]^+$<br>$^1H$ NMR (400 MHz, $CD_3OD$): δ 6.80 (s, 1H), 6.70 (s, 1H), 3.82 (s, 3H), 3.73-3.74 (m, 2H), 3.32-3.40 (m, 1H), 2.56-3.18 (m, 5H), 1.20-1.26 (m, 7H), 1.03-1.09 (m, 6H), 0.94-0.98 (m, 6H). |
| 16 | 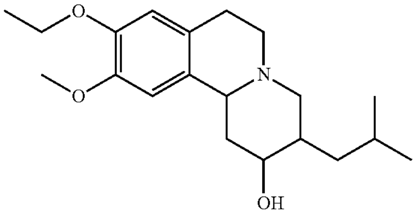 [SMILES: CCOc1cc2c(cc1OC)C1CC(O)C(CC(C)C)CN1CC2] | MS m/z (ESI): 334.2 $[M + H]^+$<br>$^1H$ NMR (600 MHz, $CD_3OD$): δ 0.90-0.97 (m, 6H), 1.02-1.11 (m, 1H), 1.42-1.55 (m, 5H), 1.55-1.62 (m, 1H), 1.64-1.80 (m, 2H), 1.91-2.03 (m, 1H), 2.37-2.50 (m, 1H), 2.54-2.70 (m, 2H), 2.94-3.17 (m, 4H), 3.34-3.46 (m, 1H), 3.88 (s, 3H), 4.01-4.15 (m, 2H), 6.63 (s, 1H), 6.76 (s, 1H). |

TABLE 1-continued

Structure and characterization data of compounds of Examples 12-20

| Examples | Structural formula | Spectra |
|---|---|---|
| 17 | 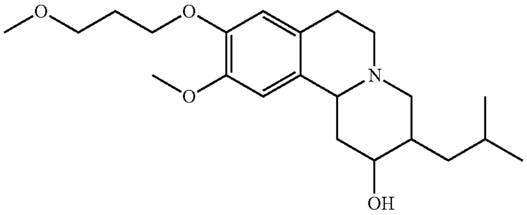 [SMILES: COCCCOc1cc2c(cc1OC)C1CC(O)C(CC(C)C)CN1CC2] | MS m/z (ESI): 378.2 $[M + H]^+$; $^1H$ NMR (600 MHz, $CDCl_3$): δ 6.68 (s, 1H), 6.56 (s, 1H), 4.09 (t, 2H), 3.82 (s, 3H), 3.57 (t, 2H), 3.48 (dd, 1H), 3.42-3.35 (m, 1H), 3.34 (s, 3H), 3.26-3.20 (m, 2H), 3.15-3.02 (m, 2H), 2.88 (dd, 1H), 2.77-2.61 (m, 2H), 2.60-2.48 (m, 2H), 2.33 (t, 1H), 2.11-2.04 (m, 2H), 1.83-1.75 (m, 1H), 1.70-1.58 (m, 1H), 1.06-0.99 (m, 1H), 0.94-0.89 (m, 6H). |
| 18 | 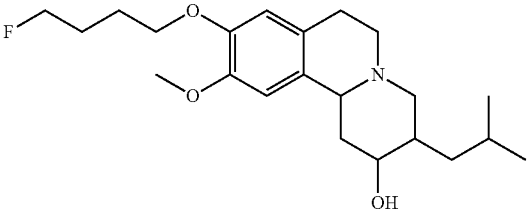 [SMILES: COc1cc2c(cc1OCCCCF)CCN1CC(CC(C)C)C(O)CC21] | MS m/z (ESI): 380.2 $[M + H]^+$; $^1H$ NMR (600 MHz, $CDCl_3$) δ 6.68 (s, 1H), 6.59 (s, 1H), 4.43-4.64 (m, 2H), 3.98-4.13 (m, 2H), 3.82 (s, 3H), 3.33-3.44 (m, 1H), 2.95-3.19 (m, 4H), 2.52-2.68 (m, 2H), 2.39-2.51 (m, 1H), 1.83-2.03 (m, 5H), 1.64-1.80 (m, 3H), 1.44-1.65 (m, 3H), 1.01-1.14 (m, 1H), 0.86-1.00 (m, 6H). |
| 19 | 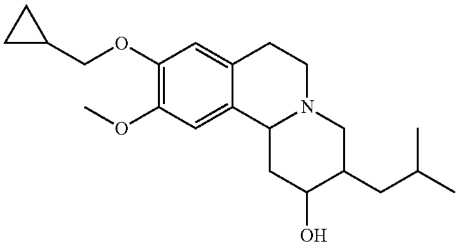 [SMILES: COc1cc2c(cc1OCC1CC1)CCN1CC(CC(C)C)C(O)CC21] | MS m/z (ESI): 359.3 $[M + H]^+$; 1H NMR (600 MHz, $CD_3OD$) δ 6.78 (s, 1H), 6.66 (s, 1H), 3.82-3.79 (m, 5H), 3.48 (dd, 1H), 3.2 (dd, 1H), 3.08-3.00 (m, 3H), 2.89 (dd, 1H), 2.77-2.61 (m, 5H), 2.60-2.48 (m, 2H), 2.33 (t, 1H), 1.75-1.65 (m, 3H), 1.47-1.40 (m, 1H), 1.27-1.22 (m, 1H), 1.06-0.99 (m, 1H), 0.97-0.92 (m, 6H), 0.61-0.57 (m, 2H), 0.34-0.30 (m, 2H). |
| 20 | 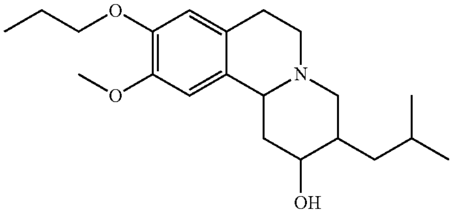 [SMILES: CCCOc1cc2c(cc1OC)C1CC(O)C(CC(C)C)CN1CC2] | MS m/z (ESI): 348.2 $[M + H]^+$ $^1H$ NMR (600 MHz, $CDCl_3$): δ 6.64 (s, 1H), 6.54 (s, 1H), 3.96-3.90 (t, 2H), 3.81 (s, 3H), 3.49 (dd, 1H), 3.42-3.35 (m, 1H), 3.27-3.21 (m, 2H), 3.15-3.02 (m, 2H), 2.88 (dd, 1H), 2.74-2.66 (m, 2H), 2.62-2.48 (m, 2H), 2.33 (t, 1H), 1.96-1.90 (m, 3H), 1.70-1.58 (m, 1H), 1.06-0.98 (m, 4H), 0.93-0.87 (m, 6H). |

Example 21

Compound 21

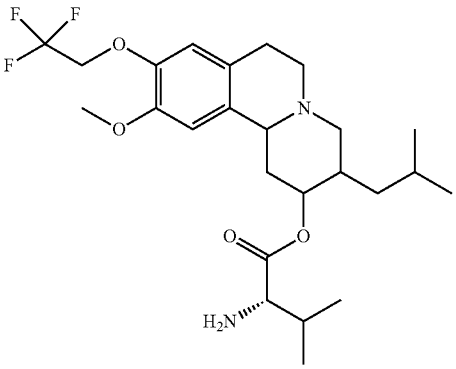

Synthetic Route:

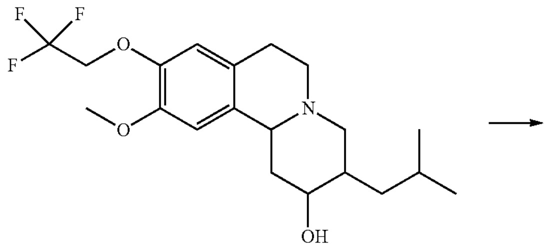

11

-continued

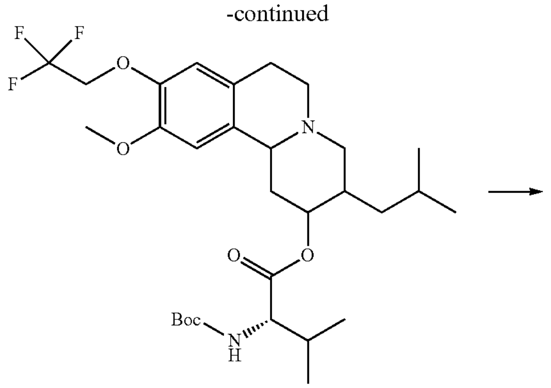

21a

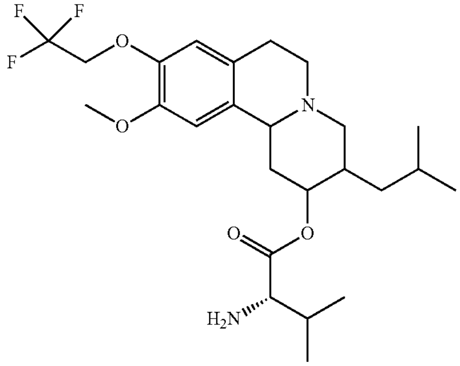

21

1. Under the protection of nitrogen, Boc-L-valine (857.6 mg, 3.95 mmol) was dissolved in dichloromethane (20 mL) under ice-bath. 4-Dimethylaminopyridine (386.9 mg, 3.16 mmol) and compound 11 (1.02 g, 2.64 mmol) were added and the mixture was reacted for 5 minutes with stirring under ice-bath. Dicyclohexylcarbodiimide (813.7 mg, 3.95 mmol) was added in one portion. The mixture was allowed to naturally warm up and reacted for 18 hours. The resulting mixture was filtered and the filtrate was concentrated under reduced pressure. The resulting residue was separated and purified by column chromatography (dichloromethane: methanol=30:1) to afford compound 21a (1.13 g, off-white solid). MS m/z (ESI): 587.3 $[M+H]^+$ 2. Compound 21a (1.13 g, 1.92 mmol) was dissolved in 1,4-dioxane solution (15 ml, at the concentration of 4M). The mixture was reacted at room temperature for 2 hours. The reaction solution was concentrated. The solid was washed with diethyl ether (10 ml*1) to afford a crude. The crude was dissolved in water (30 mL). The mixture was adjusted with saturated sodium bicarbonate aqueous solution to pH=7-8 and extracted with dichloromethane (10 ml*3). The organic phases were combined. The dichloromethane phase was washed with water (10 ml*1) and saturated sodium chloride (10 ml*1), respectively. The dichloromethane phase was dried over anhydrous sodium sulfate. The mixture was filtered to remove the solid. The dichloromethane phase was concentrated to afford compound 21 (720 mg). MS m/z (ESI): 487.3 $[M+H]^+$; $^1H$ NMR (400 MHz, $CD_3OD$) δ 6.76 (s, 1H), 6.74 (s, 1H), 4.65-4.74 (m, 1H), 4.38-4.45 (m, 2H), 3.77 (s, 3H), 3.25-3.27 (m, 1H), 2.97-3.12 (m, 3H), 2.61-2.74 (m, 2H), 2.47-2.51 (m, 1H), 1.94-2.16 (m, 3H), 1.63-1.75 (m, 1H), 1.43-1.51 (m, 1H), 1.27-1.37 (m, 1H), 1.01-1.08 (m, 2H), 0.88-1.00 (m, 12H).

Examples 22-25

Examples 22-25 were synthesized by using a method analogous to that of Example 21.

TABLE 2-1

| Structure and characterization data of compounds of Examples 22-25 | | |
|---|---|---|
| Examples | Structural formula | Spectra |
| 22 | 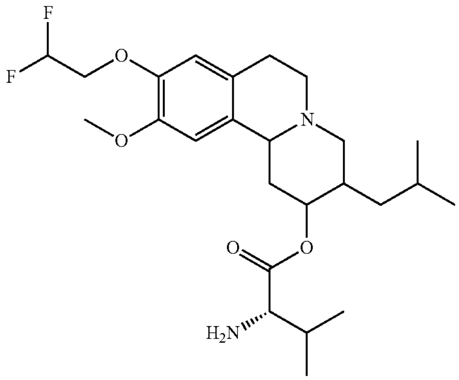 [SMILES: COc1cc2c(cc1OCC(F)F)CCN1CC(CC(C)C)C(OC(=O)[C@@H](N)C(C)C)CC21] | MS m/z (ESI): 469.3 $[M+H]^+$; $^1H$ NMR (400 MHz, $CD_3OD$): δ 6.78 (s, 1H), 6.77 (s, 1H), 6.01-6.31 (m, 1H), 4.71-4.78 (m, 1H), 4.15-4.23 (m, 2H), 3.82 (s, 3H), 3.29-3.33 (m, 1H), 3.05-3.17 (m, 3H), 2.67-2.78 (m, 2H), 2.49-2.57 (m, 2H), 1.99-2.24 (m, 3H), 1.55-1.66 (m, 1H), 1.47-1.54 (m, 1H), 1.29-1.42 (m, 1H), 1.06-1.13 (m, 2H), 0.93-1.05 (m, 12H). |

TABLE 2-1-continued
| Structure and characterization data of compounds of Examples 22-25 | | |
|---|---|---|
| Examples | Structural formula | Spectra |
| 23 | 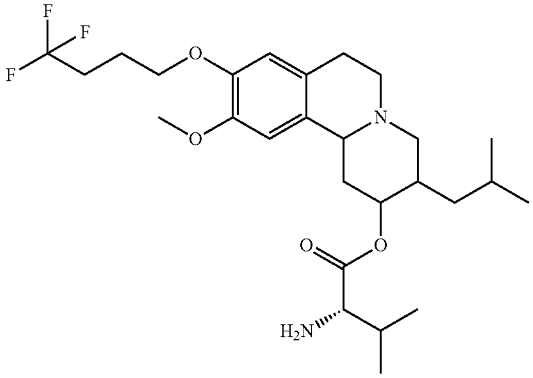 [SMILES: COc1cc2c(cc1OCCCC(F)(F)F)CCN1CC(CC(C)C)C(OC(=O)[C@@H](N)C(C)C)CC21] | MS m/z (ESI): 515.3 [M + H]$^+$ $^1$H NMR (400 MHz, $CD_3OD$) δ 6.70 (s, 1H), 6.67 (s, 1H), 4.65-4.73 (m, 1H), 3.97-4.00 (m, 2H), 3.75 (s, 3H), 3.23-3.26 (m, 1H), 2.99-3.10 (m, 3H), 2.63-2.70 (m, 2H), 2.45-2.52 (m, 1H), 2.30-2.40 (m, 2H), 1.93-2.14 (m, 5H), 1.60-1.71 (m, 1H), 1.41-1.47 (m, 1H), 1.26-1.36 (m, 1H), 1.00-1.08 (m, 2H), 0.88-1.00 (m, 12H). |
| 24 | 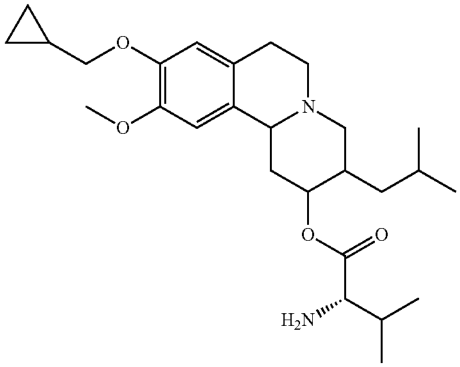 [SMILES: COc1cc2c(cc1OCC1CC1)CCN1CC(CC(C)C)C(OC(=O)[C@@H](N)C(C)C)CC21] | MS m/z (ESI): 459.3 [M + H]$^+$ $^1$HNMR (600 MHz, $CD_3OD$): δ 6.60-6.79 (m, 2H), 5.50-5.15 (m, 1H), 4.60-4.74 (m, 1H), 4.07-4.09 (m, 1H), 3.78-3.88 (m, 5H), 3.72-3.74 (m, 2H), 3.25-3.45 (m, 1H), 2.63-3.25 (m, 3H), 2.37-2.47 (m, 2H), 1.75-2.09 (m, 1H), 1.51-1.74 (m, 1H), 1.25-1.49 (m, 3H), 1.14-1.24 (m, 6H), 0.95-1.03 (m, 6H), 0.80-0.88 (m, 1H), 0.62-0.65 (m, 2H), 0.32-0.39 (m, 2H). |
| 25 | 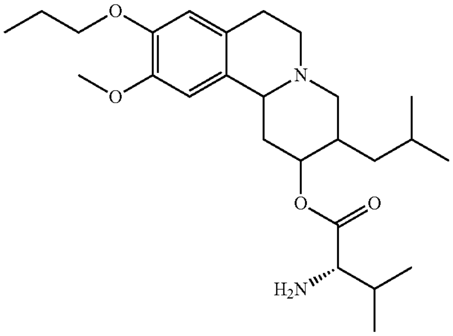 [SMILES: CCCOc1cc2c(cc1OC)C1CC(OC(=O)[C@@H](N)C(C)C)C(CC(C)C)CN1CC2] | MS m/z (ESI): 447.3 [M + H]$^+$ $^1$H NMR (600 MHz, $CD_3OD$) δ 6.60-6.79 (m, 2H), 5.04-5.61 (m, 1H), 4.60-4.73 (m, 1H), 3.95-4.10 (m, 3H), 3.71-3.87 (m, 5H), 3.42-3.52 (m, 3H), 3.02-3.20 (m, 2H), 2.33-2.48 (m, 2H), 1.79-1.96 (m, 4H), 1.27-1.49 (m, 2H), 0.87-1.18 (m, 16H). |

Examples 26-28

Compounds 26-28 were synthesized by using a method analogous to that of Example 11.

TABLE 2-2

Structure and characterization data of compounds of Examples 26-28

| Examples | Structural formula | Spectra |
|---|---|---|
| 26 | 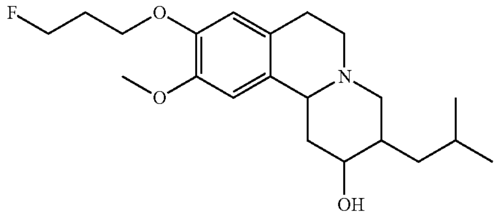 Compound 26 | MS m/z (ESI): 366.2 $[M + H]^+$; $^1$H NMR (400 MHz, $CD_3OD$): δ 6.81 (s, 1H), 6.72 (s, 1H), 4.56-4.71 (m, 2H), 3.81 (s, 3H), 2.91-3.22 (m, 4H), 2.38-2.71 (m, 3H), 1.99-2.27 (m, 2H), 1.31-1.81 (m, 6H), 1.02-1.11 (m, 1H), 0.94-0.98 (m, 6H). |
| 27 | 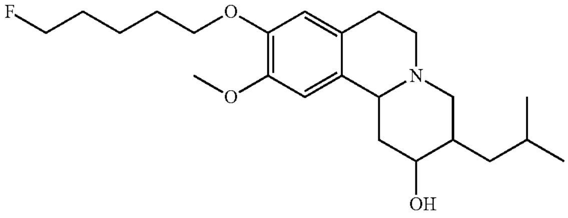 Compound 27 | MS m/z (ESI): 394.3 $[M + H]^+$; $^1$H NMR (600 MHz, $CDCl_3$) δ 6.68 (s, 1H), 6.58 (s, 1H), 4.36-4.60 (m, 2H), 3.94-4.07 (m, 2H), 3.81 (s, 3H), 3.30-3.53 (m, 1H), 2.89-3.20 (m, 4H), 2.50-2.70 (m, 2H), 2.36-2.53 (m, 1H), 1.94-2.02 (m, 1H), 1.84-1.91 (m, 2H), 1.65-1.83 (m, 5H), 1.45-1.64 (m, 5H), 1.02-1.10 (m, 1H), 0.89-0.97 (m, 6H). |
| 28 | 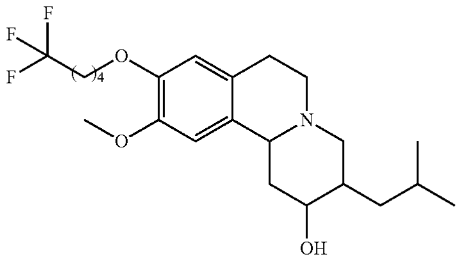 Compound 28 | MS m/z (ESI): 430.2 $[M + H]^+$; $^1$H NMR (600 MHz, $CDCl_3$) δ 6.66 (s, 1H), 6.58 (s, 1H) 3.96-4.09 (m, 2H), 3.82 (s, 3H), 3.32-3.44 (m, 1H), 2.92-3.17 (m, 4H), 2.51-2.68 (m, 2H), 2.38-2.55 (m, 1H), 2.11-2.25 (m, 2H), 1.93-2.08 (m, 1H), 1.84-1.94 (m, 2H), 1.66-1.82 (m, 4H), 1.55-1.67 (m, 3H), 1.42-1.56 (m, 2H), 1.01-1.11 (m, 1H), 0.88-0.98 (m, 6H). |

Example 29

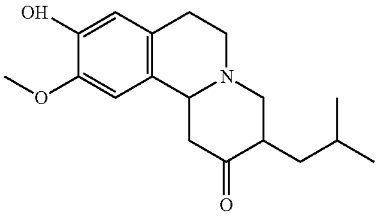

Fragment 1

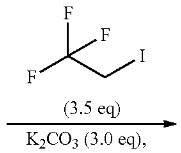

-continued

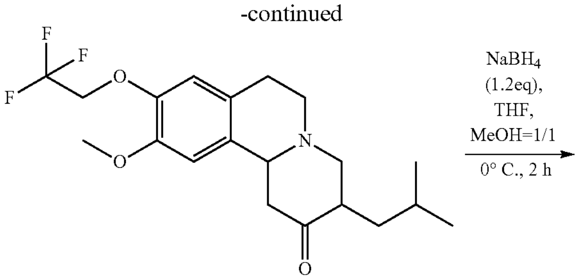

Intermediate 1

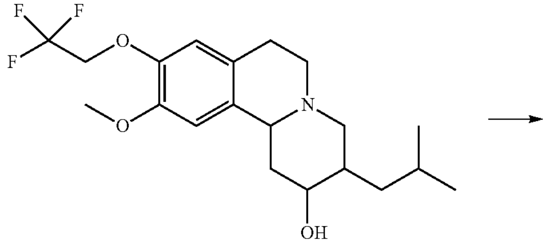

11

-continued

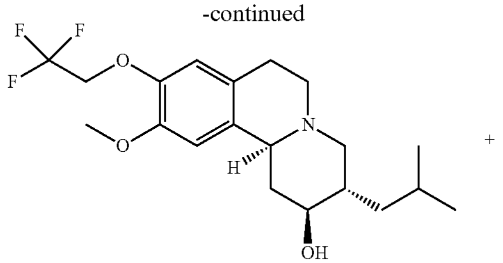

11-P3

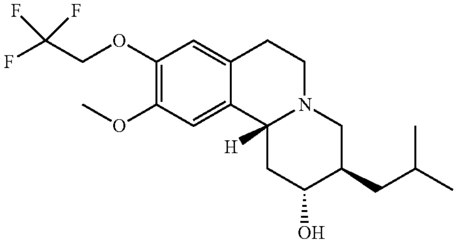

11-P4

Step 1: Synthesis of Intermediate I:

To a 2 L single-necked flask, reactant fragment I (106 g, 350 mmol, 1 eg) and anhydrous potassium carbonate (145 g, 1050 mmol, 3 cg) were added, anhydrous N,N-dimethylformamide (700 mL) was added, and then 1,1,1-trifluoro-2-iodoethane (184 g, 875 mmol, 2.5 eq) was added. The mixture was reacted at 140° C. for 11 h. As it showed by TLC (PE:EA=3:1) monitoring, some reactant remained. 1,1,1-Trifluoro-2-iodoethane (73.5 g, 350 mmol, 1 eq) was added additionally. The mixture was reacted at 140° C. for another 8 h. After the completion of the reaction, the reaction mixture was cooled to room temperature. The reaction system was poured into a mixed solution of water (3.5 L) and saturated brine (700 mL) and extracted with ethyl acetate (700 ml) four times. The ethyl acetate phases were combined. The combined ethyl acetate phase was washed with water (700 mL) once and saturated sodium chloride solution (700 mL) once, respectively. The ethyl acetate phase was dried over anhydrous sodium sulfate and filtered to remove anhydrous sodium sulfate. The ethyl acetate phase was concentrated under reduced pressure. The residue was slurried with a mixed solution of ethyl acetate (175 mL) and petroleum ether (175 mL) and filtered. The solid was collected. The solid was washed with a mixed solution of ethyl acetate (175 mL) and petroleum ether (175 mL) three times in total. After drying, 50 g of a light yellow solid was afforded. Light yellow solid (50 g) was dissolved in 95% ethanol (700 mL) at reflux and the mixture was allowed to naturally cool down for 4 h. Crystals were precipitated. The mixture was filtered and crystals were collected. The crystals were washed with 95% ethanol (175 mL) at room temperature three times in total. After drying, intermediate I (38.4 g, light yellow crystal) was afforded, with a yield of 28.5%.

MS m/z (ESI): 386.2 $[M+H]^+$, $^1H$ NMR (600 MHz, $CDCl_3$): δ 6.75 (s, 1H), 6.59 (s, 1H), 4.38-4.34 (m, 2H), 3.82 (s, 3H), 3.53-3.51 (m, 1H), 3.32-3.28 (m, 1H), 3.15-3.09 (m, 2H), 2.91-2.88 (m, 1H), 2.75-2.72 (m, 2H), 2.61-2.53 (m, 2H), 2.38-2.34 (m, 1H), 1.82-1.78 (m, 1H), 1.69-1.62 (m, 1H), 1.06-1.01 (m, 1H), 0.92-0.90 (m, 6H).

Step 2: Synthesis of Compound 11:

In a 1 L single-necked flask, intermediate I (38.46 g, 100 mmol, 1 eq) and tetrahydrofuran (150 mL) were added. Under ice-bath, sodium borohydride (4.56 g, 120 mmol, 1.2 eq) was added and then anhydrous methanol (150 ml) was added, and the mixture was stirred under ice-bath for 2 h. After the completion of the reaction, the reaction was quenched with 1N HCl (300 mL, 300 mmol, 3 eq) in a nitrogen atmosphere under ice-bath. Under ice-bath, saturated sodium carbonate solution (300 mL) was added dropwise to produce a light yellow solid. The mixture was filtered and the solid was collected. The solid was washed with water (300 mL) three times in total. After drying, 39 g of a light yellow solid was afforded. The solid was dissolved with ethyl acetate (300 mL) at the temperature of 80° C. Then petroleum ether (100 mL) was added. The mixture was allowed to naturally cool down for 4 h. A white solid was precipitated. The solid was collected and washed with a mixed solution of ethyl acetate (50 mL) and petroleum ether (50 mL) three times in total. After drying, compound 11 (23.07 g, white solid) was afforded, with a yield of 59.6%. MS m/z (ESI): 388.2 $[M+H]^+$; $^1H$ NMR (600 MHz, $CDCl_3$): δ 6.71 (s, 1H), 6.70 (s, 1H), 4.38-4.31 (m, 2H), 3.82 (s, 3H), 3.41-3.35 (m, 1H), 3.13-2.96 (m, 4H), 2.64-2.54 (m, 2H), 2.47-2.40 (m, 1H), 2.04-1.94 (m, 1H), 1.75-1.66 (m, 3H), 1.61-1.45 (m, 2H), 1.08-1.02 (m, 1H), 0.92-0.90 (m, 6H).

Step 3: Resolution of Compound 11

12.33 g of compound 11 was weighed. Chiral isomers were separated by the HPLC method, using Daicel Preparative chromatography and Daicel chiral column. The corresponding components thereof were collected and subjected to rotary evaporation to remove the solvent and hence a pure optical isomer was obtained. The separation method and detection results could be seen in Tables 3-4.

TABLE 3

| Chiral separation method of compound 11 | | |
|---|---|---|
| Chromatographic column | CHIRALPAK AD-H(ADHOCD-UE022) | |
| Size of chromatographic column | 0.46 cm I.D. × 15 cm L | |
| Injection volume | 1 ul | |
| Mobile phase | Hexane/EtOH = 90/10 (V/V) | |
| Flow rate | 1.0 ml/min | |
| Detection wavelength | UV214 nm | |
| Column temperature | 35° C. | |
| HPLC apparatus | Shimadzu LC-20AT | CP-HPLC-09 |

TABLE 4

| Chiral analysis results of compound 11 | | | |
|---|---|---|---|
| Peak Number | Retention time | Peak area | Relative peak area % |
| 1 | 4.994 | 5152535 | 48.604 |
| 2 | 5.601 | 114788 | 1.083 |
| 3 | 6.109 | 5177576 | 48.840 |
| 4 | 6.707 | 156247 | 1.474 |

Components of 11-P4 (retention time: 4.994 min) and 11-P3 (retention time: 6.109 min) were respectively collected. The solvent was removed by rotary evaporation to afford samples 11-P4 (6.1448 g) and 11-P3 (5.7844 g), respectively. The analysis method and results could be seen in Tables 5-8.

TABLE 5

| Analysis method of compound 11-P4 | |
|---|---|
| Chromatographic column | CHIRALPAK AD-H(ADH0CD-UE022) |
| Size of chromatographic column | 0.46 cm I.D. × 15 cm L |
| Injection volume | 0.5 ul |
| Mobile phase | Hexane/EtOH = 60/40 (V/V) |
| Flow rate | 1.0 ml/min |
| Detection wavelength | UV2 14 nm |
| Column temperature | 35° C. |
| HPLC apparatus | Shimadzu LC-20AT CP-HPLC-09 |
| Sample name | 11-P4 |

TABLE 6

Analysis results of compound 11-P4

| Peak Number | Retention time | Peak area | Relative peak area % |
|---|---|---|---|
| 1 | 1.920 | 502928 | 3.811 |
| 2 | 4.939 | 12433977 | 94.208 |
| 3 | 6.139 | 29066 | 0.220 |
| 4 | 6.440 | 232459 | 1.761 |

TABLE 7

| Analysis method of compound 11-P3 | |
|---|---|
| Chromatographic column | CHIRALPAK AD-H(ADH0CD-UE022) |
| Size of chromatographic column | 0.46 cm I.D. × 15 cm L |
| Injection volume | 1 ul |
| Mobile phase | Hexane/EtOH = 60/40 (V/V) |
| Flow rate | 1.0 ml/min |
| Detection wavelength | UV 214 nm |
| Column temperature | 35° C. |
| HPLC apparatus | Shimadzu LC-20AT CP-HPLC-09 |
| Sample name | 11-P3 |

TABLE 8

Analysis results of compound 11-P3

| Peak Number | Retention time | Peak area | Relative peak area % |
|---|---|---|---|
| 1 | 1.919 | 512872 | 5.985 |
| 2 | 4.999 | 150632 | 1.758 |
| 3 | 6.056 | 7906161 | 92.258 |

MS, $^{1}$HNMR and $^{13}$CNMR of compounds 11-P4 and 11-P3 are the same: MS m/z (ESI): 388.2 $[M+H]^+$;

$^{1}$HNMR (600 MHz, $CDCl_3$): δ 6.72 (s, 1H), 6.71 (s, 1H), 4.33-4.37 (q, J=8.0 Hz, 2H), 3.82 (s, 3H), 3.37-3.40 (m, 1H), 3.12-3.14 (d, J=12.0 Hz, 1H), 3.06-3.08 (m, 1H), 3.02-3.05 (m, 1H), 2.98-3.00 (m, 1H), 2.60-2.63 (m, 1H), 2.55-2.58 (m, 1H), 2.45-2.46 (m, 1H), 1.95-1.99 (t, J=12.0 Hz, 1H), 1.72-1.74 (m, 1H), 1.68-1.71 (m, 1H), 1.55-1.60 (m, 1H), 1.47-1.53 (m, 1H), 1.03-1.07 (m, 1H), 0.91-0.92 (d, J=6.0 Hz, 3H), 0.93-0.94 (d, J=6.0 Hz, 3H).

$^{13}$CNMR (150 Hz, $CDCl_3$): δ 148.5, 145.53, 132.85, 126.84, 120.80-126.34, 117.66, 109.29, 74.46, 67.66-68.36, 60.94, 59.99, 56.09, 51.74, 41.51, 40.44, 39.64, 28.83, 25.33, 24.15, 21.74.

Example 30

I. Crystal Form A of Compound 11-P4S

Step 1: Formation of mono-p-toluenesulfonate from Compound 11-P4:

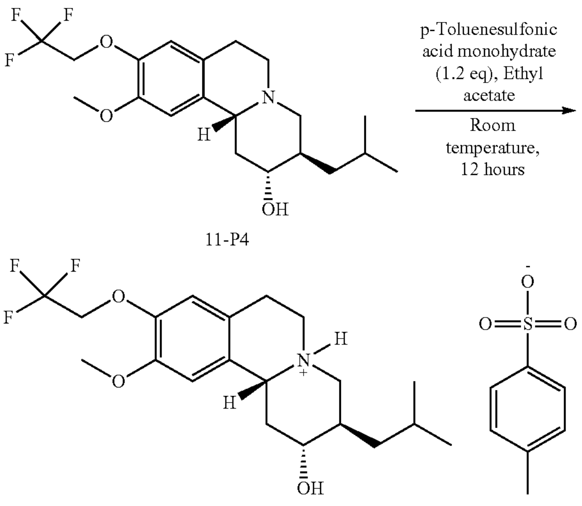

11-P4

11-P4S

11-P4 (0.20 g, 0.52 mmol) was dissolved in ethyl acetate (5 ml). A solution of p-toluenesulfonic acid monohydrate (0.12 g, 0.62 mmol) in ethyl acetate was added dropwise to precipitate a white solid. The mixture was stirred at room temperature for 12 h and suction filtered. The filter cake was washed with ethyl acetate (5 mL*3) and dried to afford compound 11-P4S as a white solid (0.22 g), with a yield of 78%.

Step 2: Method for Growing Single Crystal of Compound 11-P4S Crystal Form A 1) 9 mg of 11-P4S was weighed and placed in a 1.5 mL HPLC vial.

2) Ethanol (450 μL) was added into the solid. The temperature was increased to 40° C. and then held constant at 40° C. until the solid was completely dissolved to afford a clear solution.

3) The solution was cooled to 25° C. at 0.3° C./min while standing.

4) Crystals were precipitated and the reaction vial was observed under a microscope. The crystals were qualified and the XRSD experiment was carried out.

Step 3: XRSD Experiment of Compound 11-P4S Crystal Form A:

3.1 Instrument Parameters and Data Collection:

3.1.1 Instrument Parameters:

Single crystal diffractometer: Rigaku Oxford Diffraction XtaLAB Synergy four-circle diffractometer Detector: HyPix-6000HE plane detector;

Low-temperature system: Oxford Cryostream 800;

Light source: Cu target microfocal light source; λ=1.54184 Å, 50 W;

Distance between crystal and CCD detector: d=35 mm;

Tube voltage: 50 kV;

Tube current: 1 mA 3.1.2 Data Collection:

48459 diffraction points were collected in the diffraction experiment, wherein 4803 independent diffraction points were included (Rint=0.0672); diffraction collection range: 2θ=6.342 to 133.2°, and diffraction index range: −32≤h≤32, −19≤k≤19, −7≤l≤6. Structure analysis was carried out using SHELXT (Sheldrick, G. M. 2015. Acta Cryst. A71, 3-8) and structure refinement was carried out using SHELXL (against $F^2$) (Sheldrick, G M. 2015. Acta Cryst. C71, 3-8). Among the 4803 independent diffraction points, the parameters participating in the structural refinement were 348. After refinement, S=1.046, $R_1$=0.0318, and $wR_2$=0.0828. The residual electron density values were 0.26 and −0.32 $eÅ^{-3}$.

3.2 Data List could be Seen in Tables 9 and 10

TABLE 9

| Single crystal diffraction data list of compound 11-P4S crystal form A | |
|---|---|
| Crystal size | 0.20 × 0.10 × 0.10 $mm^3$ |
| Diffraction light source: | Cu Kα (λ = 1.54184 Å) |
| Crystal system | Orthorhombic |
| Space group | $P2_12_12$ |
| Unit cell parameters | a = 27.14408(13) Å<br>b = 16.24056(7) Å<br>c = 6.13775(3) Å<br>α = 90°, β = 90°, γ = 90° |
| Unit cell volume | V = 2705.74(2) $Å^3$ |
| Molecular number of unit cell | Z = 4 |
| Crystal density (calculated) | $D_c$ = 1.374 $Mg/m^3$ |
| Electron number of unit cell | 1184.0 |
| Linear absorption coefficient of unit cell | μ(CuKα) = 1.613 $mm^{-1}$ |
| Diffraction index range | −32 ≤ h ≤ 32, −19 ≤ k ≤ 19, −7 ≤ l ≤ 6 |
| Diffraction experiment temperature | T = 99.99 (11) K. |
| 2θ range for data collection | 6.342 to 133.2° |
| $F^2$-based goodness of fit | 1.946 |
| Residual factor [I > 2sigma(I)] | $R_1$ = 0.0318, $wR_2$ = 0.0828 |
| Residual factor (all data) | $R_1$ = 0.0337, $wR_2$ = 0.0854 |
| Peak and valley of residual electron cloud density | 0.26 and −0.32 e · $Å^{-3}$ |
| Collected diffraction points/dependent diffraction points [diffraction intensity deviation] | 48459/4803 [$R_{(int)}$ = 0.0672] |
| Flack parameter | −0.012(6) |

TABLE 10

| Atomic coordinates (×10^4) and equivalent isotropic shift parameters (Å^2 × 10^3) | | | | |
|---|---|---|---|---|
| Atom | x | y | z | U(eq) |
| S(1) | 6908.4(2) | 8039.1(3) | 4133.8(9) | 19.83(15) |
| F(2) | 10058.9(5) | 8135.6(10) | 9233(3) | 36.8(4) |
| F(1) | 9724.8(6) | 9339.3(9) | 9467(3) | 39.9(4) |
| F(3) | 9453.0(6) | 8338.9(10) | 11417(3) | 37.1(4) |
| O(3) | 6981.6(6) | 4240.2(9) | 2228(3) | 21.6(3) |
| O(1) | 9218.4(6) | 7468.1(9) | 7691(3) | 24.5(4) |
| O(4) | 7257.4(6) | 8255.4(11) | 5821(3) | 30.9(4) |
| O(2) | 9173.3(8) | 5886.1(10) | 7555(4) | 35.5(5) |
| O(6) | 6917.5(7) | 8591.7(14) | 2299(3) | 41.7(5) |
| N(1) | 7591.4(6) | 6528.1(11) | 591(3) | 17.4(4) |
| O(5) | 6951.8(7) | 7173.1(11) | 3503(4) | 41.8(5) |
| C(2) | 8099.9(9) | 7741.0(13) | 1395(4) | 22.7(5) |
| C(15) | 6301.6(8) | 5665.7(14) | −3092(4) | 19.9(5) |
| C(3) | 8346.4(8) | 7217.8(14) | 3095(4) | 19.4(5) |
| C(11) | 7285.5(8) | 4821.3(13) | 1097(4) | 17.5(4) |
| C(25) | 6312.2(8) | 8136.0(13) | 5307(4) | 19.7(5) |
| C(8) | 8284.2(8) | 6367.8(14) | 3171(4) | 18.4(5) |
| C(5) | 8910.7(8) | 7147.1(14) | 6127(4) | 20.4(5) |
| C(14) | 6625.1(8) | 5055.9(14) | −1801(4) | 19.0(5) |
| C(18) | 9280.0(9) | 8333.2(14) | 7653(4) | 23.5(5) |
| C(12) | 6954.4(8) | 5445.3(13) | −52(4) | 17.2(4) |
| C(7) | 8557.6(8) | 5905.9(14) | 4677(4) | 21.9(5) |

TABLE 10-continued

| Atomic coordinates (×10^4) and equivalent isotropic shift parameters (Å^2 × 10^3) | | | | |
|---|---|---|---|---|
| Atom | x | y | z | U(eq) |
| C(26) | 5901.0(8) | 7950.8(14) | 4044(4) | 21.3(5) |
| C(4) | 8651.2(8) | 7599.5(13) | 4625(4) | 19.4(5) |
| C(23) | 5785.9(10) | 8555.7(17) | 8212(4) | 30.3(6) |
| C(9) | 7937.3(8) | 5921.1(13) | 1632(4) | 17.9(5) |
| C(13) | 7271.4(8) | 6116.4(14) | −1064(4) | 19.5(5) |
| C(19) | 9630.5(9) | 8529.3(14) | 9458(4) | 26.5(5) |
| C(1) | 7866.9(9) | 7236.5(14) | −407(4) | 23.1(5) |
| C(24) | 6258.3(9) | 8426.3(15) | 7405(4) | 25.9(5) |
| C(10) | 7622.6(8) | 5260.0(13) | 2725(4) | 18.8(4) |
| C(27) | 5432.4(9) | 8098.1(14) | 4877(4) | 23.7(5) |
| C(22) | 5368.8(9) | 8416.6(15) | 6961(4) | 25.6(5) |
| C(16) | 5977.4(9) | 6178.0(15) | −1585(4) | 25.9(5) |
| C(17) | 5985.8(9) | 5195.1(16) | −4736(4) | 26.7(5) |
| C(6) | 8876.7(8) | 6280.3(14) | 6111(4) | 23.2(5) |
| C(21) | 4864(1) | 8623.4(17) | 7838(5) | 33.0(6) |
| C(20) | 9217.8(12) | 5012.5(16) | 7280(6) | 46.5(8) |

3.3 Conclusion

Crystal form A of compound 11-P4S was a colorless mass (0.20×0.10×0.10 $mm^3$) and belonged to the orthorhombic P21212 space group. Unit cell parameters: a=27.14408(13) Å, b=16.24056(7) Å, c=6.13775(3) Å, α=90°, β=90°, γ=90°, V=2705.74(2) $Å^3$, Z=4. Density calculated: Dc=1.374 $g/cm^3$, electron number of unit cell: F(000)=1184.0, linear absorption coefficient of unit cell: μ (Cu Kα)=1.613 $mm^{-1}$, and diffraction experiment temperature: T=99.99(11) K.

Ellipsoidal graph of molecular structure of 11-P4S could be seen in FIG. 1, and the structure of the compound was:

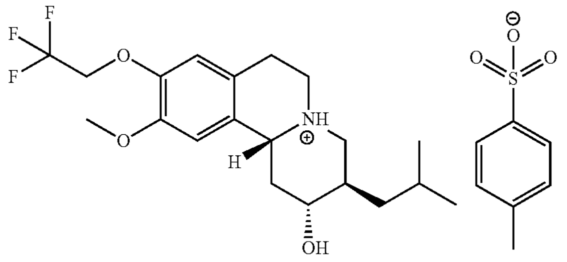 [SMILES: COc1cc2c(cc1OCC(F)(F)F)CC[NH+]1C[C@@H](CC(C)C)[C@H](O)C[C@H]21 ; Cc1ccc(S(=O)(=O)[O-])cc1]

Step 4: Characterization of Compound 11-P4S Crystal Form A 4.1 XPRD Characterization 4.1.1 Characterization Method: XRPD was Acquired on an X-Ray Powder Diffractometer Manufactured by PANalytical, and the Scan Parameters were as Shown in Table 11 Below.

TABLE 11

| XRPD scan parameters | | | |
|---|---|---|---|
| Parameter | Instrument 1 | Instrument 2 | Instrument 3 |
| Model | Empyrean | X' Pert3 | X' Pert3 |
| X-ray | Cu, Kα,<br>Kα1 (Å): 1.540598,<br>Kα2 (Å): 1.544426<br>Kα2/Kα1 intensity ratio: 0.50 | Cu, Kα,<br>Kα1 (Å): 1.540598,<br>Kα2 (Å): 1.544426<br>Kα2/Kα1 intensity ratio: 0.50 | Cu, Kα,<br>Kα1 (Å): 1.540598,<br>Kα2 (Å): 1.544426<br>Kα2/Kα1 intensity ratio: 0.50 |
| X-ray tube setting | 45 kV, 40 mA | 45 kV, 40 mA | 45 kV, 40 mA |
| Divergence slit | Automatic | 1/8° | 1/8° |

TABLE 11-continued

| XRPD scan parameters | | | |
|---|---|---|---|
| Parameter | Instrument 1 | Instrument 2 | Instrument 3 |
| Scanning mode | Continuous | Continuous | Continuous |
| Scanning range (°2Theta) | 3-40 | 3-40 | 3-40 |
| Scanning time per step (s) | 17.8 | 46.7 | 46.7 |
| Scanning step width (°2Theta) | 0.0167 | 0.0263 | 0.0263 |
| Test time | ~5 min 30 s | ~5 min | ~5 min |

Figures 1, 2:
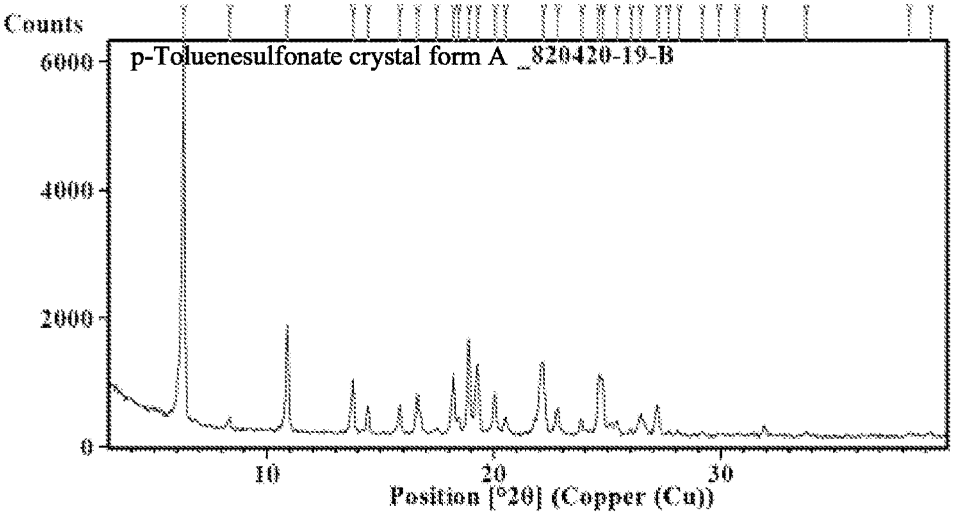
Figure 2:
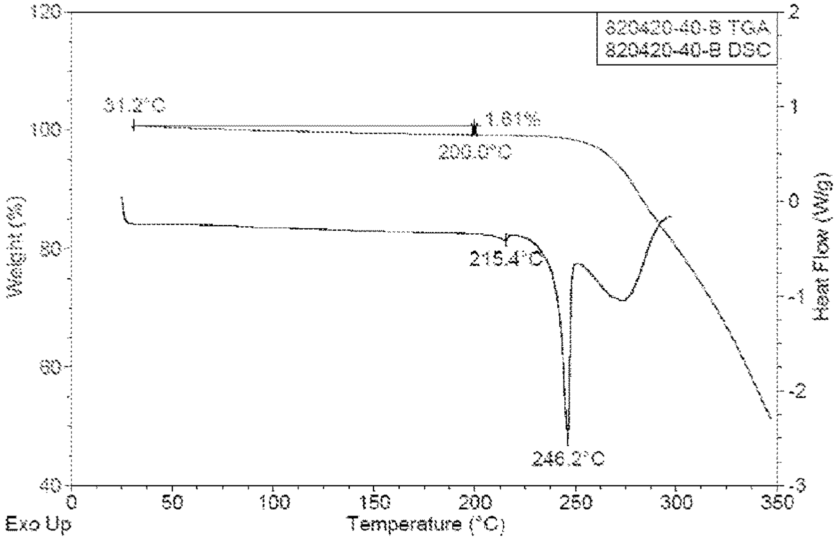

4.1.1 Results:

XPRD spectrum could be seen in FIG. 2-1 and the analysis data of the spectrum could be seen in Table 12.

TABLE 12

XRPD spectrum analysis data of crystal form A of compound 11-P4S

| Serial number | 2θ ± 0.2 (°) | Relative intensity (%) |
|---|---|---|
| 1 | 6.33 | 100.00 |
| 2 | 8.34 | 3.02 |
| 3 | 10.87 | 27.37 |
| 4 | 13.77 | 14.23 |
| 5 | 14.42 | 6.81 |
| 6 | 15.83 | 7.24 |
| 7 | 16.61 | 10.15 |
| 8 | 17.46 | 1.17 |
| 9 | 18.20 | 15.22 |
| 10 | 18.43 | 3.93 |
| 11 | 18.89 | 25.20 |
| 12 | 19.27 | 17.88 |
| 13 | 20.05 | 10.97 |
| 14 | 20.51 | 4.31 |
| 15 | 22.19 | 17.13 |
| 16 | 22.77 | 6.84 |
| 17 | 23.83 | 3.97 |
| 18 | 24.60 | 15.50 |
| 19 | 24.77 | 14.22 |
| 20 | 25.39 | 3.68 |
| 21 | 26.02 | 1.63 |
| 22 | 26.45 | 5.28 |
| 23 | 27.20 | 7.57 |
| 24 | 27.66 | 1.06 |
| 25 | 28.15 | 0.71 |
| 26 | 29.16 | 0.83 |
| 27 | 29.90 | 0.69 |
| 28 | 30.72 | 0.52 |
| 29 | 31.90 | 2.72 |
| 30 | 33.76 | 0.98 |
| 31 | 38.28 | 0.93 |
| 32 | 39.21 | 0.85 |

4.2 TGA/DSC Characterization 4.2.1 Characterization method: TGA and DSC spectra were acquired on TA Q5000/5500 thermogravimetric analyzer and TA 2500 differential scanning calorimeter, respectively and the test parameters could be seen in Table 13.

TABLE 13

TGA/DSC test parameters

| Parameter | TGA | DSC |
|---|---|---|
| Method | Linear temperature increase | Linear temperature increase |
| Sample pan | Aluminum pan, open | Aluminum pan, capped/uncapped |
| Temperature range | Room temperature-set end temperature | 25° C.-set end temperature |
| Scanning rate (° C./min) | 10 | 10 |
| Protective gas | Nitrogen | Nitrogen |

4.2.2 Results: TGA/DSC spectra of crystal form A of compound 11-P4S could be seen in FIG. 2-2. The results showed that after the sample was heated to 200° C., the weight loss was 1.6%, and there were two endothermic peaks (peak temperatures) at 215.4° C. and 246.2° C.

4.3 $^{1}$H NMR 4.3.1 Method: Liquid-state nuclear magnetic resonance spectra were acquired on Bruker 400M nuclear magnetic resonance spectrometer and DMSO-d6 was used as the solvent.

4.3.2 Results: $^{1}$H NMR spectrum could be seen in FIG. 2-3. The results showed that in the sample, the molar ratio of p-toluenesulfonic acid to free base was 1.0:1.0 and the molar ratio of MTBE to free base was 0.02:1.0, the mass fraction of p-toluenesulfonate was 30.7% and the mass fraction of MTBE was 0.3%.

II. Crystal Form B of Compound 11-P4S

Step 1. Preparation Method 109 mg of crystal form A of compound 11-P4S was dissolved in MeOH (2 mL). Then 18 mL of an antisolvent, THF was added. The mixture was placed at −20° C., stirred and filtered to separate a solid. The solid was placed at room temperature for air-drying to afford crystal form B of compound 11-P4S.

Step 2. Crystal Characterization 2.1 Characterization Method: Characterization Methods of XPRD, TGA/DSC and $^{1}$H NMR were the Same as Those of Crystal Form A of Compound 11-P4S.

2.2 Experiment Results 2.2.1 XPRD

Figures 2, 3:
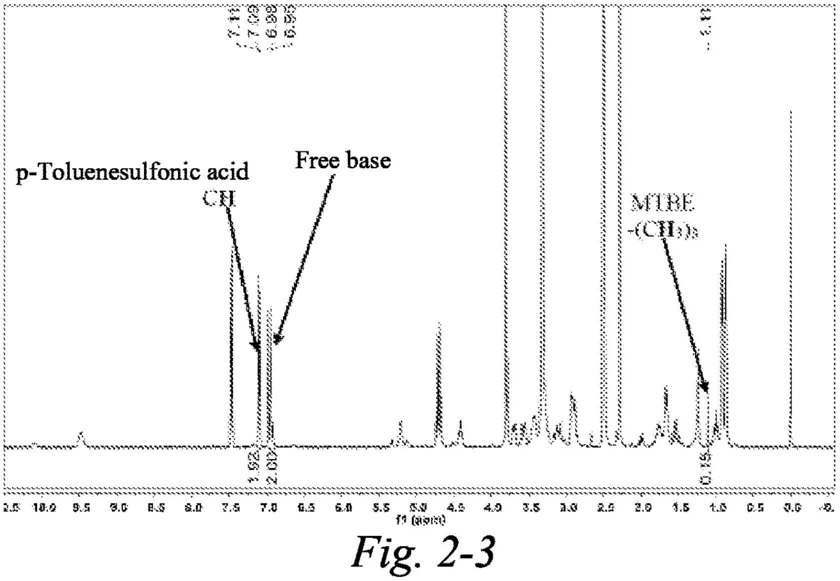
Figures 1, 3:
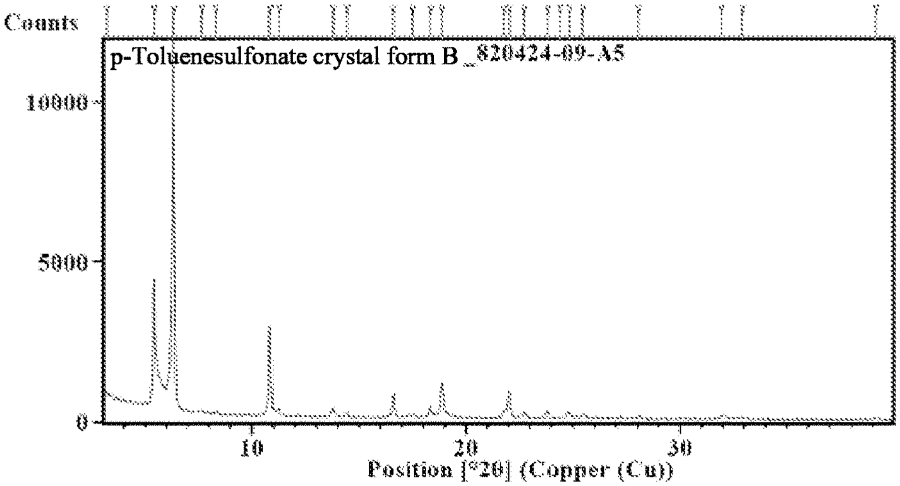
Figures 2, 3:
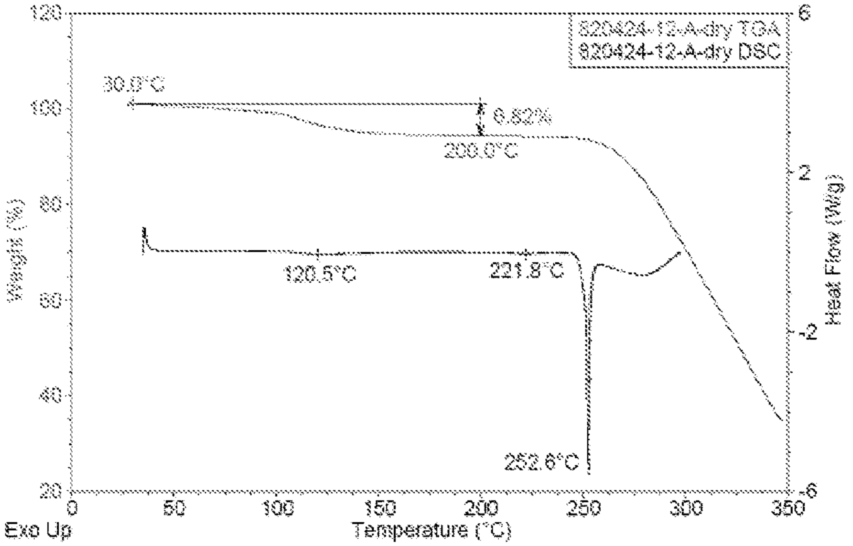
Figure 3:
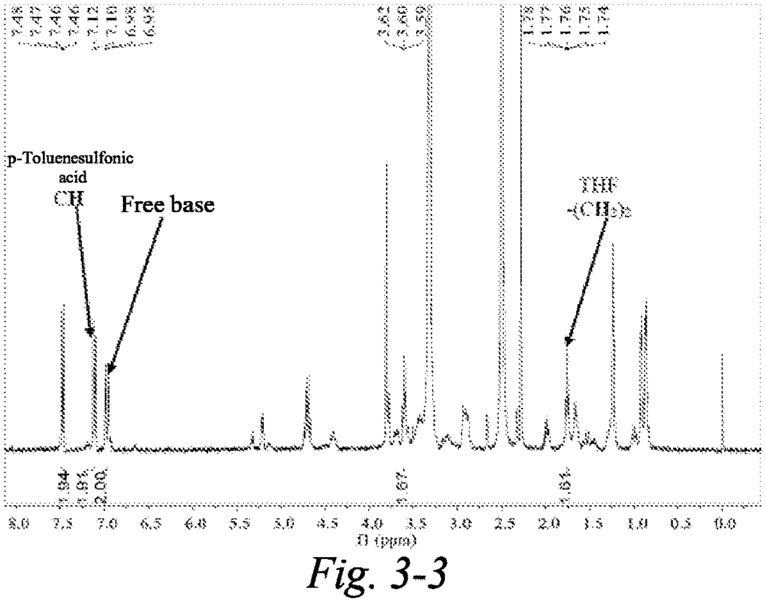

XPRD spectrum could be seen in FIG. 3-1 and the analysis data of the spectrum could be seen in Table 14.

TABLE 14

XRPD spectrum analysis data of crystal form B of compound 11-P4S

| Serial number | 2θ ± 0.2 (°) | Relative intensity (%) |
|---|---|---|
| 1 | 3.19 | 6.64 |
| 2 | 5.42 | 37.46 |
| 3 | 6.32 | 100.00 |
| 4 | 7.63 | 2.00 |
| 5 | 8.30 | 1.98 |
| 6 | 10.85 | 25.02 |
| 7 | 11.24 | 2.77 |
| 8 | 13.77 | 2.83 |
| 9 | 14.42 | 1.99 |
| 10 | 16.60 | 6.39 |
| 11 | 17.49 | 1.19 |
| 12 | 18.33 | 3.25 |
| 13 | 18.88 | 9.47 |
| 14 | 21.77 | 2.20 |
| 15 | 22.02 | 7.10 |

TABLE 14-continued

XRPD spectrum analysis data of crystal form B of compound 11-P4S

| Serial number | 2θ ± 0.2 (°) | Relative intensity (%) |
|---|---|---|
| 16 | 22.72 | 1.54 |
| 17 | 23.80 | 1.80 |
| 18 | 24.36 | 0.70 |
| 19 | 24.80 | 1.56 |
| 20 | 25.45 | 1.03 |
| 21 | 28.05 | 0.67 |
| 22 | 31.93 | 0.92 |
| 23 | 32.90 | 0.36 |
| 24 | 39.15 | 0.23 |

2.2.2 TGA/DSC

TGA/DSC spectra of crystal form B of compound 11-P4S could be seen in FIG. 3-2, which showed that when the sample was heated to 200° C., the weight loss was 6.8%, and there were three endothermic peaks (peak temperatures) at 120.5° C., 221.8° C. and 252.6° C.

2.2.3 $^1$H NMR $^1$H NMR spectrum could be seen in FIG. 3-3, which showed that in the sample, the molar ratio of p-toluenesulfonic acid to free base was 1.0:1.0, the molar ratio of THF to free base was 0.5, the corresponding weight loss was 6.5% and no residue of methanol was detected.

III. Crystal Form C of Compound 11-P4S

Step 1. Preparation Method 121.2 mg of crystal form A of compound 11-P4S was weighed and dissolved in MeOH (2.2 mL). Then DCM (75 mL) was added and allowed to form a clear solution. The solution was still clear following stirring for two hours at room temperature. The solution was transferred to room temperature for air-drying to afford crystal form C of compound 11-P4S.

Step 2. Crystal Characterization 2.1 Characterization Method: Characterization Methods of XPRD, TGA/DSC and $^1$H NMR were the Same as Those of Crystal Form a of Compound 11-P4S.

2.2 Experiment Results 2.2.1 XPRD

Figures 1, 4:
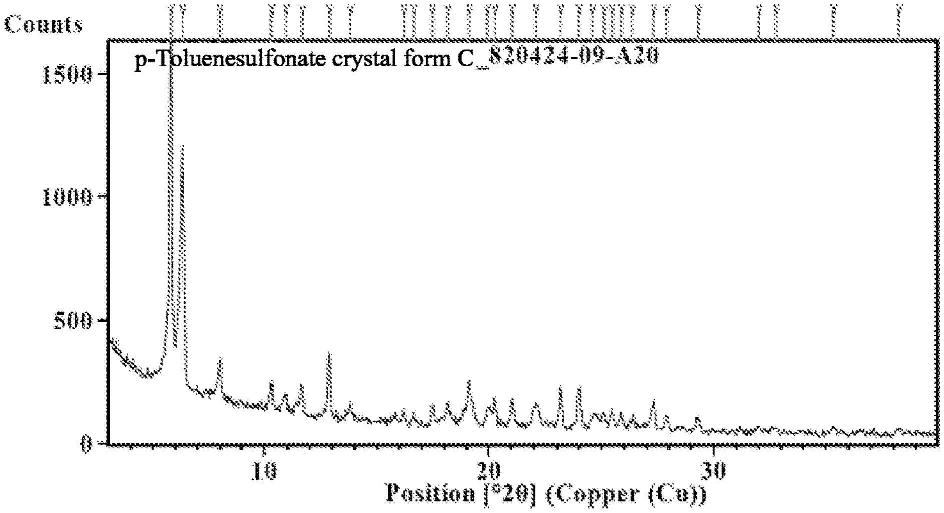
Figures 2, 4:
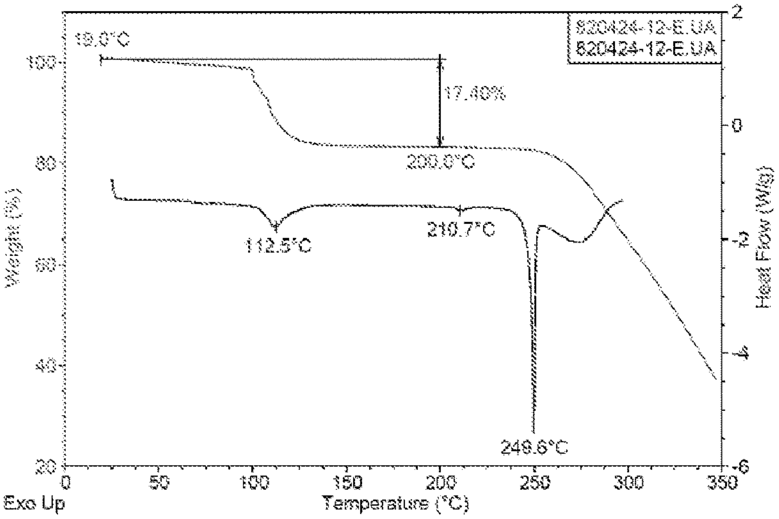
Figures 3, 4:
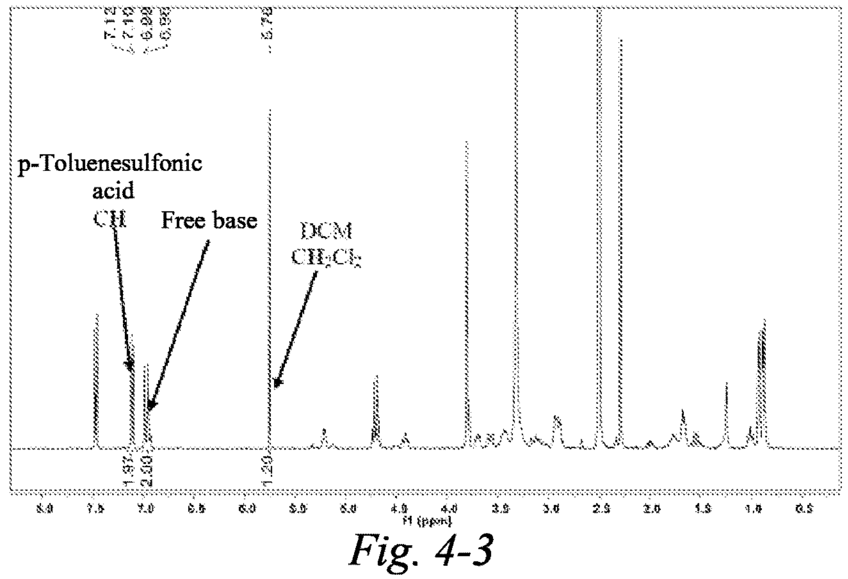

XPRD spectrum could be seen in FIG. 4-1 and the analysis data of the spectrum could be seen in Table 15.

TABLE 15

XRPD spectrum analysis data of crystal form C of compound 11-P4S

| Serial number | 2θ ± 0.2 (°) | Relative intensity (%) |
|---|---|---|
| 1 | 5.81 | 100.00 |
| 2 | 6.33 | 68.41 |
| 3 | 7.99 | 11.46 |
| 4 | 10.31 | 7.94 |
| 5 | 10.92 | 3.63 |
| 6 | 11.63 | 8.11 |
| 7 | 12.86 | 18.29 |
| 8 | 13.80 | 3.36 |
| 9 | 16.21 | 2.98 |
| 10 | 16.64 | 2.38 |
| 11 | 17.47 | 4.50 |
| 12 | 18.16 | 6.21 |
| 13 | 19.09 | 13.10 |
| 14 | 19.94 | 4.74 |
| 15 | 20.26 | 7.84 |
| 16 | 21.02 | 7.77 |
| 17 | 22.07 | 6.12 |
| 18 | 23.17 | 11.63 |
| 19 | 24.00 | 11.55 |
| 20 | 24.60 | 3.66 |
| 21 | 25.09 | 4.43 |
| 22 | 25.47 | 5.47 |
| 23 | 25.87 | 4.49 |
| 24 | 26.35 | 2.94 |
| 25 | 27.32 | 9.04 |
| 26 | 27.92 | 4.08 |
| 27 | 29.30 | 4.01 |
| 28 | 32.02 | 1.81 |
| 29 | 32.79 | 1.68 |
| 30 | 35.36 | 2.18 |
| 31 | 38.21 | 1.53 |

2.2.2 TGA/DSC

TGA/DSC spectra of crystal form C of compound 11-P4S could be seen in FIG. 4-2, which showed that when the sample was heated to 200° C., the weight loss was 17.4% and there were three endothermic peaks (peak temperatures) at 112.5° C., 210.7° C. and 249.6° C.

2.2.3 $^1$H NMR $^1$H NMR spectrum could be seen in FIG. 4-3, which showed that in the sample, the molar ratio of p-toluenesulfonic acid to free base was 1.0:1.0, the molar ratio of DCM to free base was 0.2, the mass fraction of the solvent was 3.1% and no residue of methanol was detected.

IV. Crystal Form D of Compound 11-P4S

Step 1. Preparation Method 93.3 mg of crystal form A of compound 11-P4S was weighed. 1,4-dioxane (3 mL) was added thereto. The mixture was placed at room temperature and stirred for four days. Then the sample was suction filtered. The filter cake was placed at 150° C. and heated for about 5 minutes to afford crystal form D of compound 11-P4S.

Step 2. Crystal Characterization 2.1 Characterization Method: Characterization Methods of XPRD, TGA/DSC and $^1$H NMR were the Same as Those of Crystal Form a of Compound 11-P4S.

2.2 Experiment Results 2.2.1 XPRD

Figures 1, 5:
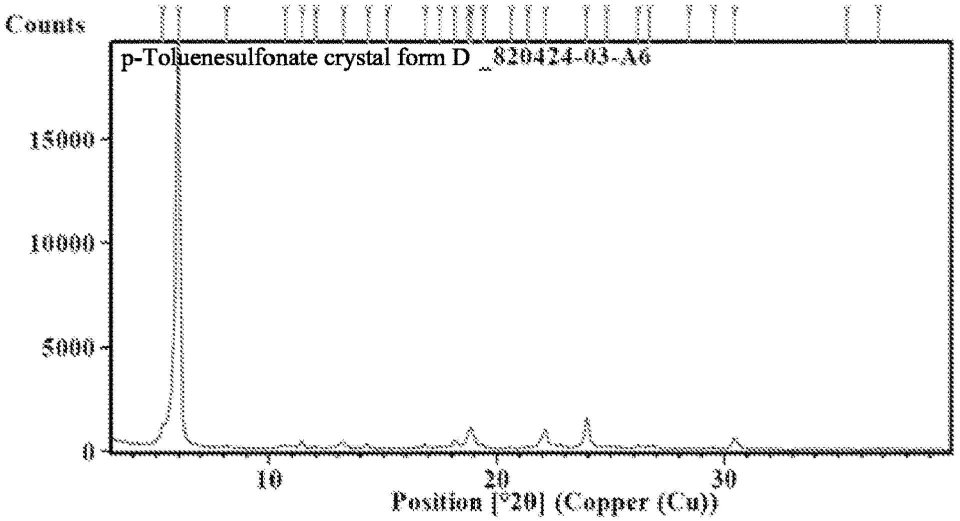
Figures 2, 5:
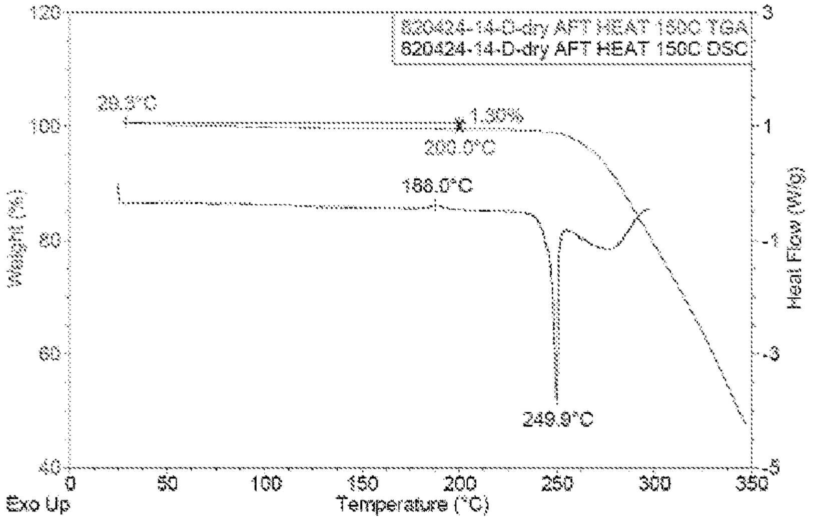
Figures 3, 5:
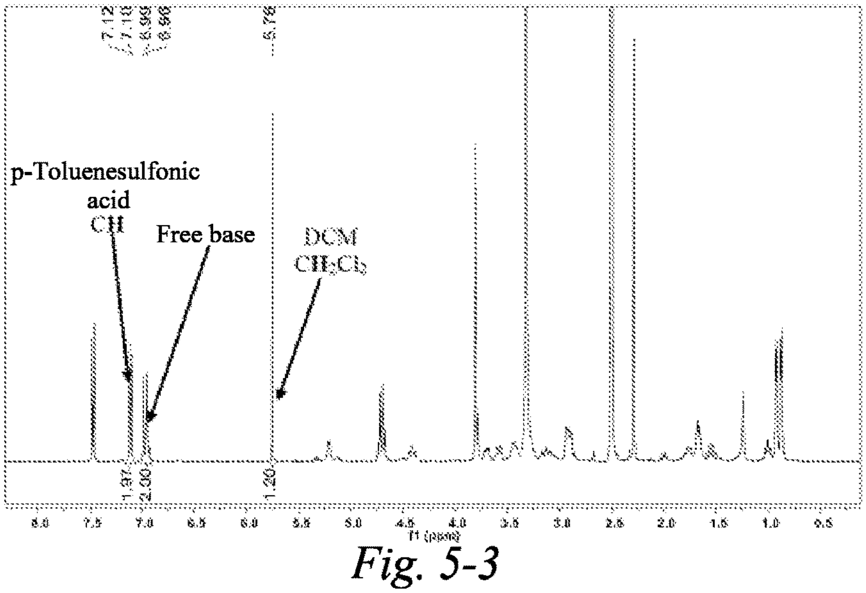

XPRD spectrum could be seen in FIG. 5-1 and the analysis data of the spectrum could be seen in Table 16.

TABLE 16

XRPD spectrum analysis data of crystal form D of compound 11-P4S

| Serial number | 2θ ± 0.2 (°) | Relative intensity (%) |
|---|---|---|
| 1 | 5.31 | 5.21 |
| 2 | 6.02 | 100.00 |
| 3 | 8.11 | 0.48 |
| 4 | 10.69 | 0.83 |
| 5 | 11.43 | 2.10 |
| 6 | 12.01 | 0.40 |
| 7 | 13.24 | 1.55 |
| 8 | 14.29 | 1.18 |
| 9 | 15.17 | 0.12 |
| 10 | 16.83 | 1.19 |
| 11 | 17.49 | 0.49 |
| 12 | 18.13 | 2.08 |
| 13 | 18.74 | 4.27 |
| 14 | 18.88 | 4.97 |
| 15 | 19.43 | 0.94 |
| 16 | 20.62 | 0.49 |
| 17 | 21.37 | 0.62 |

TABLE 16-continued

| XRPD spectrum analysis data of crystal form D of compound 11-P4S | | |
|---|---|---|
| Serial number | 2θ ± 0.2 (°) | Relative intensity (%) |
| 18 | 22.12 | 5.00 |
| 19 | 23.91 | 7.66 |
| 20 | 24.81 | 0.76 |
| 21 | 26.19 | 1.09 |
| 22 | 26.68 | 0.86 |
| 23 | 28.43 | 0.24 |
| 24 | 29.52 | 0.50 |
| 25 | 30.42 | 2.74 |
| 26 | 35.36 | 0.21 |
| 27 | 36.77 | 0.32 |

2.2.2 TGA/DSC

TGA/DSC spectra of crystal form D of compound 11-P4S could be seen in FIG. 5-2, which showed that when the sample was heated to 200° C., the weight loss was 1.3%, and there were one endothermic peak (peak temperature) at 249.9° C. and one exothermic peak (peak temperature) at 188.0° C.

2.2.3 $^{1}$H NMR

1H NMR could be seen in FIG. 5-3, which showed that in the sample, the molar ratio of p-toluenesulfonic acid to free base was 1.0:1.0 and no residue of 1,4-dioxane was detected.

V. Crystal Form E of Compound 11-P4S

Step 1. Preparation Method 62.1 mg of crystal form A of compound 11-P4S was weighed. IPA (10 mg) was added thereto. The mixture was placed at 50° C. and stirred for 2 hours. The filtrate was slowly cooled down (50° C.-5° C., 0.1° C./min) to precipitate an appropriate amount of a solid. Then suction filtration was performed to afford crystal form E of compound 11-P4S.

Step 2. Crystal Characterization 2.1 Characterization Method: Characterization Methods of XPRD, TGA/DSC and $^{1}$H NMR were the Same as Those of Crystal Form a of Compound 11-P4S.

2.2 Experiment Results 2.2.1 XPRD

Figures 1, 6:
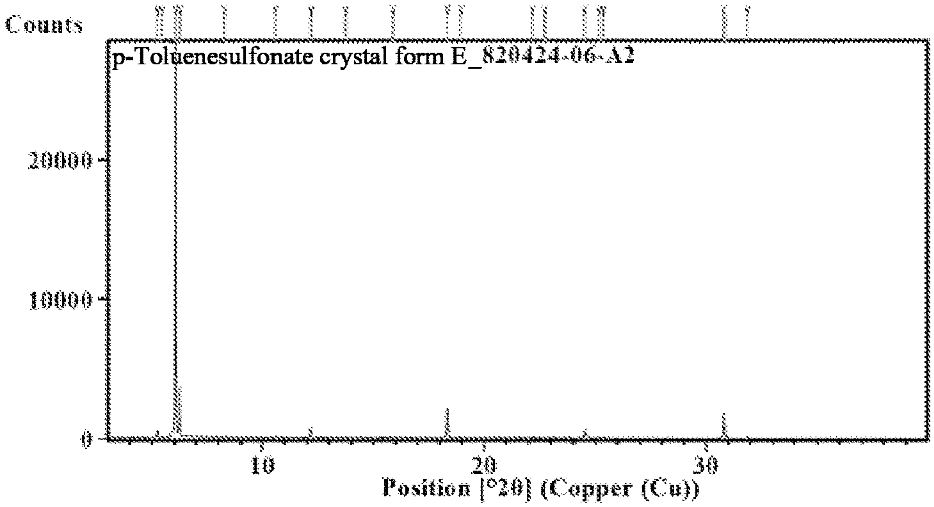
Figures 2, 6:
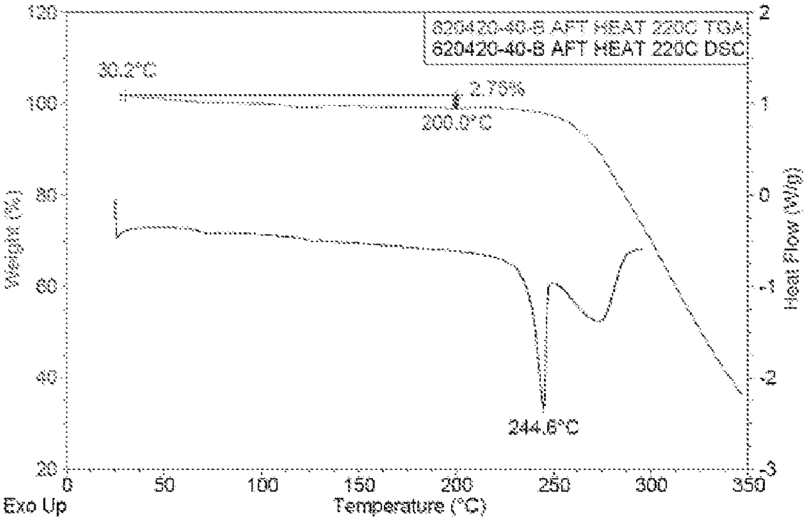
Figures 3, 6:
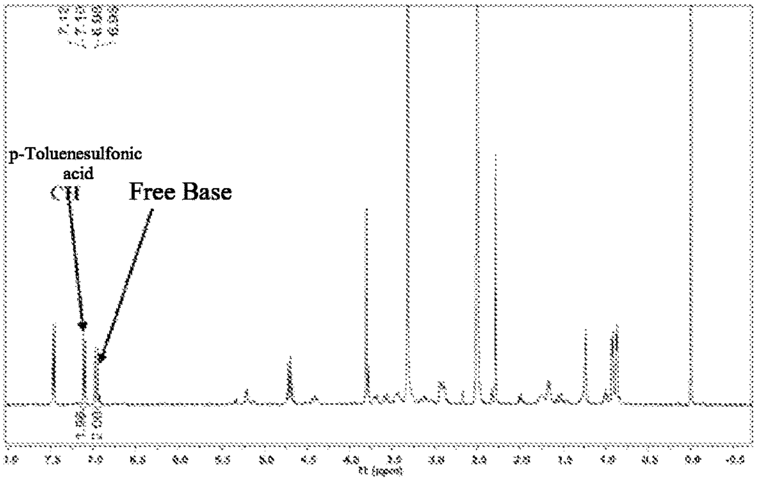

XPRD spectrum could be seen in FIG. 6-1 and the analysis data of the spectrum could be seen in Table 17.

TABLE 17

| XRPD spectrum analysis data of crystal form E of compound 11-P4S | | |
|---|---|---|
| Serial number | 2θ ± 0.2 (°) | Relative intensity (%) |
| 1 | 5.24 | 1.72 |
| 2 | 5.46 | 0.28 |
| 3 | 6.06 | 100.00 |
| 4 | 6.25 | 12.62 |
| 5 | 8.26 | 0.25 |
| 6 | 10.56 | 0.29 |
| 7 | 12.17 | 2.33 |
| 8 | 13.73 | 0.13 |
| 9 | 15.87 | 0.33 |
| 10 | 18.32 | 6.29 |
| 11 | 18.93 | 0.30 |
| 12 | 22.15 | 0.33 |
| 13 | 22.71 | 0.12 |
| 14 | 24.50 | 1.68 |
| 15 | 25.17 | 0.31 |
| 16 | 25.33 | 0.28 |
| 17 | 30.79 | 5.93 |

TABLE 17-continued

| XRPD spectrum analysis data of crystal form E of compound 11-P4S | | |
|---|---|---|
| Serial number | 2θ ± 0.2 (°) | Relative intensity (%) |
| 18 | 30.88 | 2.88 |
| 19 | 31.83 | 0.25 |

2.2.2 TGA/DSC

TGA/DSC spectra of crystal form E of compound 11-P4S could be seen in FIG. 6-2, which showed that when the sample was heated to 200° C., the weight loss was 2.8%, and there was one endothermic peak (peak temperature) at 244.6° C.

2.2.3 $^{1}$H NMR $^{1}$H NMR spectrum could be seen in FIG. 6-3, which showed that in the sample, the molar ratio of p-toluenesulfonic acid to free base is 1.0:1.0 and no residue of MTBE was detected.

VI. Crystal Form of Compound 11-P3S

Step 1: Formation of Mono-p-Toluenesulfonate from Compound 11-P3:

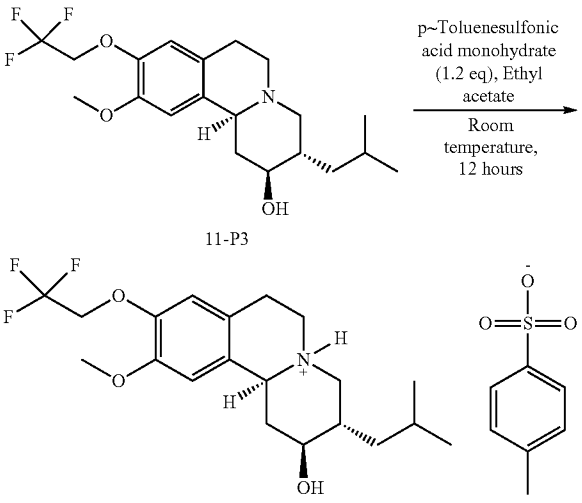

11-P3

11-P3S

11-P3 (0.20 g, 0.52 mmol) was dissolved in ethyl acetate (5 ml). A solution of p-toluenesulfonic acid monohydrate (0.12 g, 0.62 mmol) in ethyl acetate was added dropwise to precipitate a white solid. The mixture was stirred at room temperature for 12 h and suction filtered. The filter cake was washed with ethyl acetate (5 mL*3) and dried to afford compound 11-P3S as a white solid (0.22 g), with a yield of 78%.

Step 2: Method for Growing Single Crystal of Compound 11-P3S:

1) 11.6 mg of 11-P3S was weighed and placed in a 1.5 mL HPLC vial.

2) Ethanol (348 μL) was added into the solid. The temperature was increased to 60° C. and then held constant at 60° C. until the solid was completely dissolved to afford a clear solution.

3) The solution was cooled to 25° C. at 0.5° C./min while standing.

4) Crystals were precipitated and the reaction vial was observed under a microscope. The crystals were qualified and the XRSD experiment was carried out.

Step 3: Single Crystal XRSD Experiment of 11-P3S:

3.1 Instrument Parameters and Data Collection 3.1.1 Instrument Parameters: Same as that in Section 3.1.1 of Crystal Form a of Compound 11-P4S 3.1.2 Data collection: 36655 diffraction points were collected in the diffraction experiment, wherein 4793 independent diffraction points were included ($R_{int}$=0.0525). diffraction collection range: 2θ=6.342 to 133.17°, and diffraction index range: −32≤h≤30, −19≤k≤16, −7≤1≤7. Structure analysis was carried out using SHELXT (Sheldrick, G. M. 2015. Acta Cryst. A71, 3-8) and structure refinement was carried out using SHELXL (against F2) (Sheldrick, G. M. 2015. Acta Cryst. C71, 3-8). Among the 4793 independent diffraction points, the parameters participating in the structural refinement were 348. After refinement, S=1.041, $R_1$=0.0324, and $wR_2$=0.0824. The residual electron density values were 0.32 and −0.26 eÅ$^{-3}$.

3.2 Data List could be Seen in Tables 18 and 19

TABLE 18

| Single crystal diffraction data list of compound 11-P3S | |
|---|---|
| Crystal size | 0.20 × 0.20 × 0.10 mm$^3$ |
| Diffraction light source: | Cu Kα (λ = 1.54184Å) |
| Crystal system | Orthorhombic |
| Space group | $P2_12_12$ |
| Unit cell parameters | a = 27.1619(4) Å<br>b = 16.2359(2) Å<br>c = 6.13160(10) Å<br>α = 90°, β = 90°, γ = 90° |
| Unit cell volume | V = 2704.02(7) Å$^3$ |
| Molecular number of unit cell | Z = 4 |
| Crystal density (calculated) | $D_c$ = 1.375 Mg/m$^3$ |
| Electron number of unit cell | 1184.0 |
| Linear absorption coefficient of unit cell | μ(Cu Kα) = 1.614 mm−$^1$ |
| Diffraction index range | −32 ≤ h ≤ 30, −19 ≤ k ≤ 16, −7 ≤ 1 ≤ 7 |
| Diffraction experiment temperature | T = 99.99 (11) K. |
| 29 range for data collection | 6.342 to 133.17° |
| F$^2$-based goodness of fit | 1.041 |
| Residual factor [I > 2sigma(I)] | $R_1$ = 0.0324, $wR_2$ = 0.0824 |
| Residual factor (all data) | $R_1$ = 0.0343, $wR_2$ = 0.0854 |
| Peak and valley of residual electron cloud density | 0.32 and −0.26 e · Å$^{-3}$ |
| Collected diffraction points/dependent diffraction points [diffraction intensity deviation] | 36655/4793 [$R_{(int)}$ = 0.0525] |
| Flack parameter | −0.010(7) |

TABLE 19

Atomic coordinates (×10^4) and equivalent isotropic shift parameters (A^2 × 10^3)

| Atom | x | y | z | U(eq) |
|---|---|---|---|---|
| S(l) | 3092.0(2) | 8039.9(3) | 4132.8(10) | 22.85(15) |
| F(3) | 58.4(6) | 8137.6(10) | 9232(3) | 39.7(4) |
| F(1) | 276.5(7) | 9341.2(9) | 9468(3) | 42.7(4) |
| F(2) | 546.7(7) | 8339.1(10) | 11424(3) | 40.7(4) |
| O(3) | 3018.0(6) | 4239.5(10) | 2227(3) | 23.9(4) |
| O(1) | 781.4(7) | 7468.2(10) | 7690(3) | 27.6(4) |
| O(4) | 2743.7(7) | 8254.4(12) | 5821(3) | 33.9(4) |
| O(5) | 3082.8(8) | 8593.2(15) | 2299(4) | 44.0(5) |
| O(2) | 826.3(8) | 5886.9(11) | 7556(4) | 37.9(5) |
| N(1) | 2408.0(7) | 6528.8(11) | 590(3) | 20.2(4) |
| O(6) | 3048.8(8) | 7175.2(12) | 3502(4) | 43.7(6) |
| C(11) | 2714.0(8) | 4820.5(14) | 1102(4) | 20.7(5) |
| C(15) | 3698.9(9) | 5667.3(15) | 3088(4) | 22.4(5) |

TABLE 19-continued

Atomic coordinates (×10^4) and equivalent isotropic shift parameters (A^2 × 10^3)

| Atom | x | y | z | U(eq) |
|---|---|---|---|---|
| C(25) | 3688.6(9) | 8136.5(14) | 5312(4) | 22.4(5) |
| C(3) | 1654.4(9) | 7219.4(15) | 3097(4) | 21.8(5) |
| C(8) | 1715.5(9) | 6366.9(15) | 3178(4) | 21.3(5) |
| C(14) | 3374.1(9) | 5055.5(14) | 1798(4) | 21.6(5) |
| C(2) | 1900.8(9) | 7741.9(14) | 1398(4) | 25.2(5) |
| C(18) | 720.1(10) | 8333.9(14) | 7658(5) | 26.1(5) |
| C(7) | 1441.3(9) | 5905.5(14) | 4679(4) | 24.8(5) |
| C(5) | 1089.3(9) | 7147.6(14) | 6130(4) | 22.6(5) |
| C(26) | 4098.0(9) | 7951.0(14) | 4051(4) | 23.7(5) |
| C(12) | 3046.0(9) | 5444.7(13) | 53(4) | 20.1(5) |
| C(10) | 2376.5(9) | 5259.8(14) | 2722(4) | 21.7(5) |
| C(19) | 369.4(10) | 8530.0(15) | 9461(5) | 29.5(6) |
| C(9) | 2062.0(9) | 5921.5(14) | 1633(4) | 21-1(5) |
| C(27) | 4566.2(10) | 8097.0(15) | 4867(4) | 26.7(5) |
| C(13) | 2727.9(9) | 6116.4(15) | 1060(4) | 22.2(5) |
| C(4) | 1349.1(9) | 7599.1(14) | 4625(4) | 21.8(5) |
| C(24) | 3742.2(10) | 8426.6(16) | 7407(5) | 28.9(6) |
| C(23) | 4213.2(11) | 8555.0(18) | 8204(5) | 33.5(6) |
| C(22) | 4631.4(10) | 8415.9(15) | 6967(4) | 28.8(6) |
| C(1) | 2132.4(10) | 7234.9(15) | 403(4) | 25.8(5) |
| C(16) | 4021.4(10) | 6179.7(16) | 1584(5) | 29.1(6) |
| C(17) | 4013.8(10) | 5195.8(16) | 4731(5) | 29.2(6) |
| C(6) | 1123.4(9) | 6280.4(15) | 6112(5) | 26.5(5) |
| C(21) | 5135.7(11) | 8623.3(18) | 7837(5) | 36.1(7) |
| C(20) | 781.2(13) | 5012.0(17) | 7276(7) | 49.2(9) |

3.3 Conclusion

Figure 7:
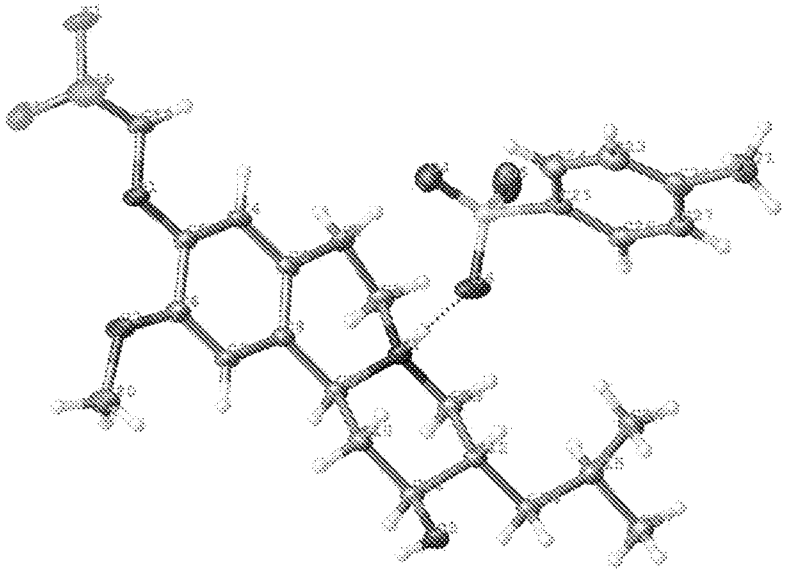
FIG. 7: ellipsoidal graph of molecular structure of compound 11-P3S

Crystal form of compound 11-P3S was a colorless mass (0.20×0.20×0.10 mm$^3$) and belonged to the orthorhombic $P2_12_12$ space group. Unit cell parameters: a=27.1619(4) Å, b=16.2359(2) Å, c=6.13160(10) Å, α=90°, β90°, γ=90°, V=2704.02(7) Å3, Z=4. Density calculated: Dc=1.375 g/cm$^3$, electron number of unit cell: F(000)=1184.0, linear absorption coefficient of unit cell: μ (Cu Kα)=1.614 mm$^{-1}$, and diffraction experiment temperature: T=99.99(11) K. Ellipsoidal graph of molecular structure of compound 11-P3S could be seen in FIG. 7, and the structure of the compound was:

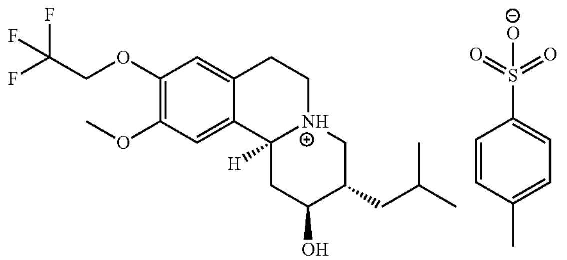 [SMILES: COc1cc2c(cc1OCC(F)(F)F)CC[NH+]1C[C@H](CC(C)C)[C@@H](O)C[C@@H]21 ; Cc1ccc(S(=O)(=O)[O-])cc1]

Example 31

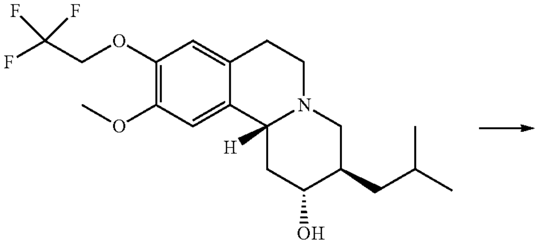

11-P4

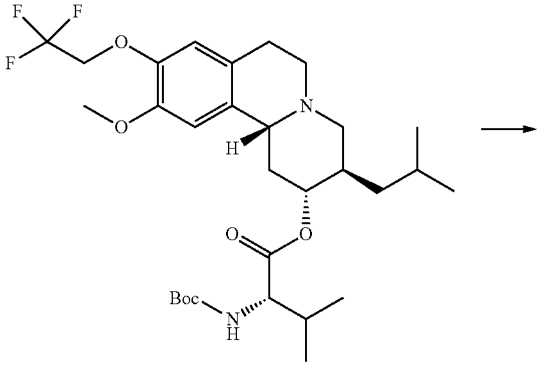

Eml-11P4a

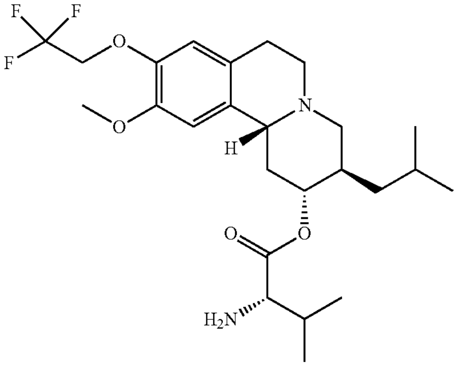

21-P3

Under the protection of nitrogen, Boc-L-valine (857.6 mg, 3.95 mmol) was dissolved in dichloromethane (20 mL) under ice-bath. 4-Dimethylaminopyridine (386.9 mg, 3.16 mmol) and compound 11-P4 (1.02 g, 2.63 mmol) were added and the mixture was reacted for 5 minutes with stirring under ice-bath. Dicyclohexylcarbodiimide (813.7 mg, 3.95 mmol) was added in one portion. The mixture was allowed to naturally warm up and reacted for 18 hours. The resulting mixture was filtered and the filtrate was concentrated under reduced pressure. The resulting residue was separated and purified by column chromatography (dichloromethane:methanol=30:1) to afford compound Eml-11P4a (1.13 g, off-white solid), with a yield of 73.2%. MS m/z (ESI): 587.3 [M+1]

Compound Eml-11P4a (1.13 g, 1.92 mmol) was dissolved in a 15 ml of solution of 4M HCl in 1,4-dioxane. The mixture was reacted at room temperature for 2 hours. The reaction solution was concentrated. The solid was washed with diethyl ether (10 ml*1) to afford a crude. The crude was dissolved in water (30 mL). The mixture was adjusted with saturated sodium bicarbonate aqueous solution to pH=7-8 and extracted with dichloromethane (10 ml*3). The organic phases were combined. The dichloromethane phase was washed with water (10 ml*1) and saturated sodium chloride (10 ml*1), respectively. The dichloromethane phase was dried over anhydrous sodium sulfate. The mixture was filtered to remove the solid. The dichloromethane phase was concentrated to afford compound 21-P3 (720 mg), with a yield of 76.8%. MS m/z (ESI): 487.3 $[M+H]^+$.

Example 32

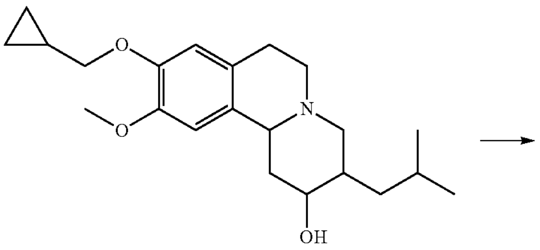

19

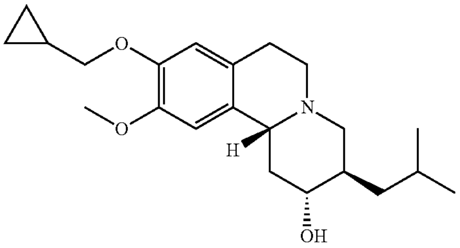

19P2

7.53 g of compound 19 was weighed. Chiral isomers were separated by the HPLC method, using Daicel Preparative chromatography and Daicel chiral column. The corresponding components thereof were collected and subjected to rotary evaporation to remove the solvent and hence a pure optical isomer was obtained. The separation method could be seen in Table 20.

TABLE 20

Chiral separation method of compound 19

| | | |
|---|---|---|
| Chromatographic column | CHIRALPAK IG-3 (IG30CD-WE016) | |
| Size of chromatographic column | 0.46 cm I.D. × 15 cm L | |
| Injection volume | 1 ul | |
| Mobile phase | Hexane/EtOH = 60/40 (V/V) | |
| Flow rate | 1.0 ml/min | |
| Detection wavelength | UV 214 nm | |
| Column temperature | 35° C. | |
| HPLC apparatus | Shimadzu LC-20AT | CP-HPLC-09 |
| Sample name | 19 | |

TABLE 21

| Chiral analysis results of compound 19 | | | |
|---|---|---|---|
| Peak Number | Retention time | Peak area | Relative peak area % |
| 1 | 3.481 | 246012 | 14.159 |
| 2 | 5.397 | 1225940 | 70.559 |
| 3 | 12.004 | 265519 | 15.282 |

19P2 (retention time: 5.397 min) and other components were collected, respectively, to afford 5.11 g of compound 19P2, with a product purity of 98.15%. MS m/z (ESI): 360.2 $[M+H]^+$; $^1H$ NMR (600 MHz, $CDCl_3$): δ 6.63 (s, 1H), 6.56 (s, 1H), 3.83-3.79 (m, 5H), 3.49-3.46 (m, 1H), 3.42-3.35 (m, 1H), 3.28-3.02 (m, 4H), 2.89 (dd, 1H), 2.77-2.61 (m, 2H), 2.60-2.48 (m, 2H), 2.33 (t, 1H), 1.82-1.75 (m, 1H), 1.70-1.58 (m, 1H), 1.06-0.99 (m, 1H), 0.93-0.87 (m, 6H), 0.64-0.59 (m, 2H), 0.36-0.31 (m, 2H).

Example 33

Step 1: Formation of Mono-p-Toluenesulfonate from Compound 19P2:

Step 3: Single Crystal XRSD Experiment of 19P2S:

(1) Instrument parameters: Same as that in Section 3.1.1 of crystal form A of compound 11-P4S (2) Date collection 24167 diffraction points were collected in the diffraction experiment, wherein 4899 independent diffraction points were included (Rint=0.0646). diffraction collection range: 2θ=6.33 to 133.182°, and diffraction index range: −7≤h≤5, −18≤k≤17, −33≤l≤33. Structure analysis was carried out using SHELXT (Sheldrick, G. M. 2015. Acta Cryst. A71, 3-8) and structure refinement was carried out using SHELXL (against $F^2$) (Sheldrick, G. M. 2015. Acta Cryst. C71, 3-8). Among the 4899 independent diffraction points, the parameters participating in the structural refinement were 339. After refinement, S=1.020, $R_1$=0.0373, and $wR_2$=0.0920. The residual electron density values were 0.38 and −0.33 $eÅ^{-3}$.

(3) Data list could be seen in Tables 22 and 23

TABLE 22

| Single crystal diffraction data list of compound 19P2S | |
|---|---|
| Crystal size | 0.30 × 0.10 × 0.04 $mm^3$ |
| Diffraction light source: | Cu Kα (λ = 1.54184 Å) |

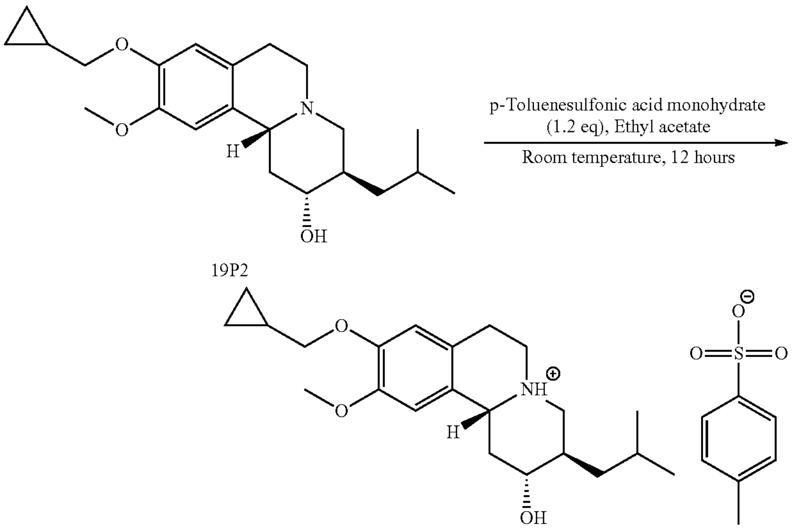

19P2

19P2S

Compound 19P2 (3.00 g, 8.34 mmol) was dissolved in ethyl acetate (30 ml). A solution of p-toluenesulfonic acid monohydrate (2.37 g, 12.5 mmol) in ethyl acetate was added dropwise. The mixture was stirred at room temperature for 12 h and suction filtered. The filter cake was washed with ethyl acetate (10 mL*3). The filter cake was collected and dried to afford a white solid (3.59 g), with a yield of 81%.

Step 2: Single Crystal Growth of Compound 19P2S 10 mg of 19P2S was weighed and placed into a 1.5 mL HPLC vial. Ethanol (500 μL) was added to the solid. The temperature was increased to 40° C. and then held constant at 40° C. until the solid was completely dissolved to afford a clear solution. The solution was cooled to 25° C. at 0.3° C./min while standing. Crystals were precipitated and the reaction vial was observed under a microscope. The crystals were qualified and the XRSD experiment was carried out.

TABLE 22-continued

| Single crystal diffraction data list of compound 19P2S | |
|---|---|
| Crystal system | Orthorhombic |
| Space group | $P2_12_12_1$ |
| Unit cell parameters | a = 6.28880(10) Å |
| | b = 15.7958(3) Å |
| | c = 27.9234(6) Å |
| | α = 90°, |
| | β = 90°, |
| | γ = 90° |
| Unit cell volume | V = 2773.82(9) $A^3$ |
| Molecular number of unit cell | Z = 4 |
| Crystal density (calculated) | $D_c$ = 1.273 $Mg/m^3$ |
| Electron number of unit cell | 1144.0 |
| Linear absorption coefficient of unit cell | μ(Cu Kα) = 1.385 $mm^{-1}$ |

TABLE 22-continued

| Single crystal diffraction data list of compound 19P2S | |
|---|---|
| Diffraction index range | −7 ≤ h ≤ 5, −18 ≤ k ≤ 17, −33 ≤ l ≤ 33 |
| Diffraction experiment temperature | T = 100.00(13) K. |
| 2θ range for data collection | 6.33 to 133.182° |
| $F^2$-based goodness of fit | 1.020 |
| Residual factor [I > 2sigma(I)] | $R_1$ = 0.0373, $wR_2$ = 9.0920 |
| Residual factor (all data) | $R_1$ = 0.0408, $wR_2$ = 9.0955 |
| Peak and valley of residual electron cloud density | 0.38 and −0.33 e.Å$^{-3}$ |
| Collected diffraction points/dependent diffraction points [diffraction intensity deviation] | 24167/4899 [$R_{(int)}$ = 0.0646] |
| Flack parameter | −0.003(9) |

TABLE 23

Atomic coordinates (×10^4) and equivalent isotropic shift parameters (A^2 × 10^3)

| Atom | X | y | z | U(eq) |
|---|---|---|---|---|
| S(1) | 3679.4(10) | 1522.5(4) | 2123.7(2) | 20.49(17) |
| O(5) | 5036(3) | 1569.5(13) | 2543.2(7) | 25.6(4) |
| O(1) | 6295(3) | 2376.6(12) | 4404.3(7) | 27.1(5) |
| O(3) | 3091(3) | 5298.1(14) | 1861.8(7) | 27.7(5) |
| O(4) | 2625(3) | 711.2(12) | 2070.7(8) | 26.0(5) |
| O(2) | 7304(3) | 3866.7(13) | 4142.8(8) | 27.0(5) |
| O(6) | 2207(3) | 2234.6(13) | 2084.3(8) | 29.3(5) |
| N(1) | 198(3) | 3356.0(14) | 2656.2(8) | 19.8(5) |
| C(9) | 1533(4) | 3978.1(17) | 2937.7(10) | 20.8(6) |
| C(5) | 5042(5) | 2706.3(19) | 4057.9(10) | 23.5(6) |
| C(27) | 5380(4) | 1623.1(18) | 1617.4(10) | 21.4(6) |
| C(26) | 7485(4) | 1372.9(17) | 1644.9(10) | 21.6(6) |
| C(1) | 1160(5) | 2831.8(19) | 2981(1) | 24.9(6) |
| C(8) | 2699(4) | 3524.9(19) | 3336.8(10) | 21.9(6) |
| C(11) | 1705(4) | 4900.5(18) | 2194.8(10) | 21.6(6) |
| C(10) | 2970(4) | 4431.5(18) | 2579.3(10) | 21.3(6) |
| C(24) | 7937(5) | 1624.1(18) | 797.3(11) | 25.0(6) |
| C(3) | 2131(4) | 2714.5(18) | 3487.4(10) | 22.3(6) |
| C(6) | 5568(4) | 3543.9(19) | 3913.8(10) | 21.6(6) |
| C(12) | 301(5) | 4276.1(18) | 1924.5(10) | 22.0(6) |
| C(25) | 8732(5) | 1375.4(18) | 1237.8(10) | 24.3(6) |
| C(4) | 3318(4) | 2314.0(19) | 3844.1(10) | 24.4(6) |
| C(7) | 4411(4) | 3939.7(19) | 3561.3(10) | 21.3(6) |
| C(28) | 4565(5) | 1901.1(19) | 1182.9(11) | 26.0(6) |
| C(14) | 1110(5) | 4692.0(18) | 1545.6(11) | 25.3(6) |
| C(13) | 1097(5) | 3801.8(19) | 2284(1) | 23.8(6) |
| C(15) | 1988(5) | 4076(2) | 1169.0(11) | 26.9(7) |
| C(21) | 9392(5) | 1044(2) | 4839.7(12) | 32.0(7) |
| C(18) | 5707(5) | 1566.0(19) | 4594.5(11) | 29.0(7) |
| C(2) | 252(5) | 2250(2) | 3271.9(11) | 26.0(6) |
| C(22) | 7850(5) | 4722.8(19) | 4043.3(11) | 30.0(7) |
| C(17) | 3751(6) | 4496(2) | 880.9(12) | 37.3(8) |
| C(29) | 5827(5) | 1897(2) | 778.8(11) | 28.3(7) |
| C(19) | 7239(5) | 1362.8(19) | 4983.3(11) | 27.8(6) |
| C(16) | 237(6) | 3776(2) | 831.7(13) | 37.1(8) |
| C(23) | 9308(5) | 1619(2) | 353.7(11) | 31.5(7) |
| C(20) | 7820(5) | 446(2) | 5060.9(12) | 33.2(7) |

Conclusion: Crystal of compound 19P2S was a colorless mass (0.30×0.10×0.04 mm$^3$) and belonged to the orthorhombic $P2_12_12_1$ space group. Unit cell parameters: a=6.28880(10) Å, b=15.7958(3) Å, c=27.9234(6) Å, α=90°, β=90°, γ=90°, V=2773.82(9) Å3, and Z=4. Density calculated: Dc=1.273 g/cm$^3$, electron number of unit cell: F(000)= 1144.0, linear absorption coefficient of unit cell: μ(Cu Kα)=1.385 mm$^{-1}$, and diffraction experiment temperature: T=100.00 (13) K.

Figure 8:
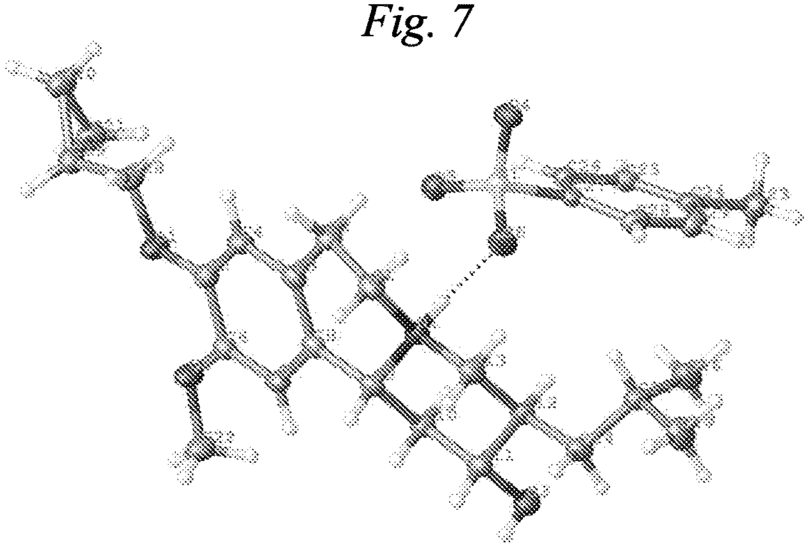
FIG. 8: ellipsoidal graph of molecular structure of compound 19P2S

Ellipsoidal graph of molecular structure of compound 19P2S could be seen in FIG. 8. The structure of the compound was:

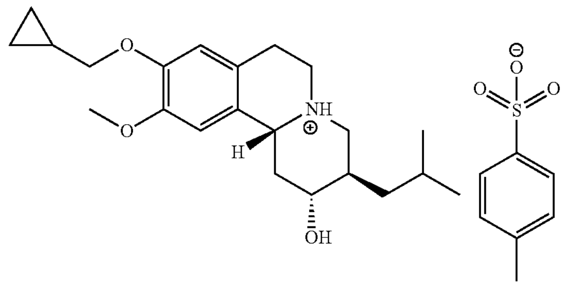 [SMILES: COc1cc2c(cc1OCC1CC1)CC[NH+]1C[C@@H](CC(C)C)[C@H](O)C[C@H]21 ; Cc1ccc(S(=O)(=O)[O-])cc1]

Example 34

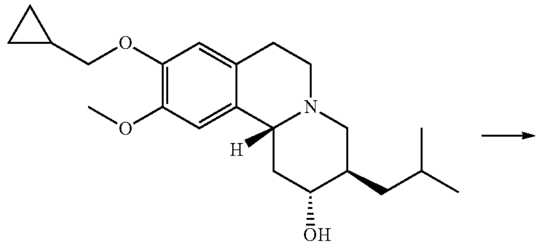

19P2

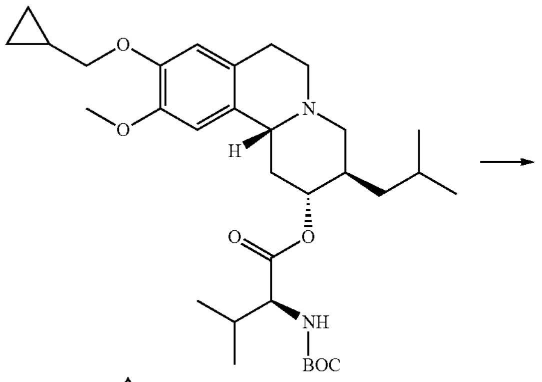

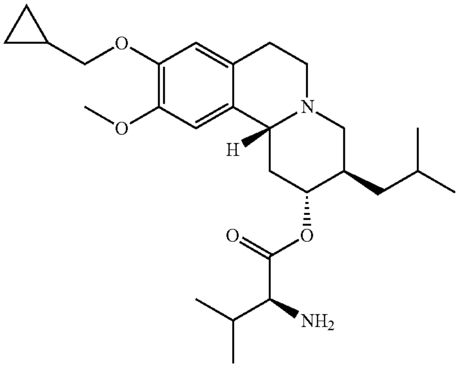

19P3

Boc-L-valine (260 mg, 1.2 mmol) was dissolved in dichloromethane (10 mL). At 0° C., dicyclohexylcarbodiimide (309 mg, 1.5 mmol) and 4-dimethylaminopyridine (12.2 mg, 0.1 mmol) were added. Then 3-isobutyl-10-methoxy-9-cyclopropylmethyl-2,3,4,6,7, 11b-hexahydro-1H-pyridine [2,1-a]isoquinolin-2-ol (359 mg, 1.0 mmol) was added. The mixture was warmed to room temperature and reacted overnight with stirring. Washing and liquid separation were carried out following the addition of water (20 mL). After concentration of the organic phase, a 6 ml of solution of 4M hydrochloric acid in dioxane was added thereto. The mixture was stirred at room temperature for 2 h. The solvent was evaporated under reduced pressure. Saturated sodium bicarbonate solution (20 mL) was added. The resulting mixture was extracted with dichloromethane (10 mL*3). The organic phases were combined, dried over anhydrous sodium sulfate and filtered. The filtrate was concentrated under reduced pressure to afford the target compound (298 mg, light yellow oily liquid). MS m/z (ESI): 459.3 $[M+H]^+$; $^1H$ NMR (600 MHz, $CDCl_3$): δ 6.71 (s, 1H), 6.62 (s, 1H), 4.76-4.70 (m, 1H), 3.83-3.79 (m, 5H), 3.48-3.44 (m, 1H), 3.42-3.35 (m, 1H), 3.28-3.02 (m, 4H), 2.89 (dd, 1H), 2.77-2.61 (m, 2H), 2.60-2.48 (m, 2H), 2.36-2.30 (m, 1H), 1.88-1.75 (m, 2H), 1.70-1.58 (m, 3H), 1.06-0.99 (m, 1H), 0.95-0.84 (m, 12H), 0.65-0.59 (m, 2H), 0.37-0.33 (m, 2H).

Comparative Example 35

Comparative Example 35

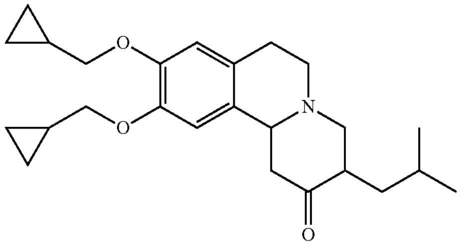

Synthetic Route:

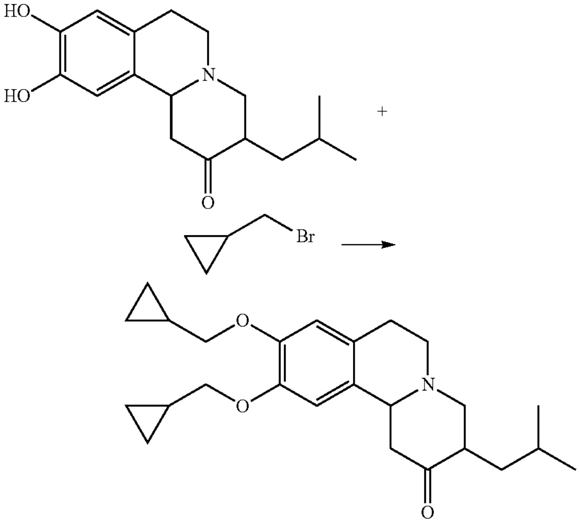

3-Isobutyl-9,10-dihydroxyl-1,3,4,6,7,11b-hexahydro-2H-pyrido[2,1-a]isoquinolin-2-one (1.7 g, 5.89 mmol) was dissolved in acetonitrile (30 mL). Cesium carbonate (9.6 g, 5 mmol) and bromomethylcyclopropane (1.91 g, 14.1 mmol) were added. The mixture was warmed to 80° C. and reacted for 5 hours with stirring. The reaction solution was concentrated and the resulting residue was purified by thin layer chromatography (petroleum ether:ethyl acetate=5:1) to afford Comparative Example 35 compound.

Comparative Example 36

Comparative Example 36

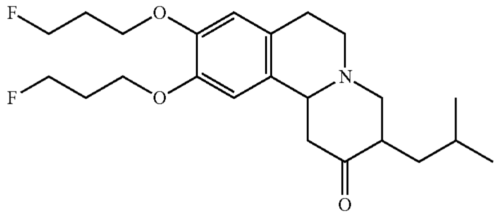

Synthetic Route:

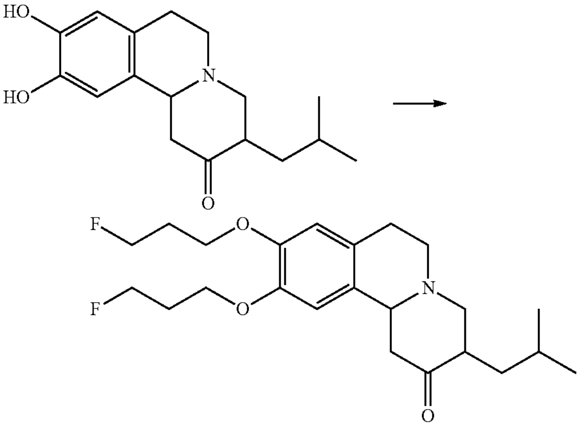

3-Isobutyl-9,10-dihydroxyl-1,3,4,6,7,11b-hexahydro-2H-pyrido[2,1-a]isoquinolin-2-one (1.00 g, 3.45 mmol) was dissolved in N,N-dimethylformamide (50 mL). Potassium carbonate (2.38 g, 17.2 mmol) was added and stirred for 30 minutes. Trifluorobromopropane (1.46 g, 10.4 mmol) was added. Under the protection of nitrogen, the mixture was warmed to 80° C. and reacted for 8 hours with stirring. The reaction solution was cooled to room temperature. Water (50 mL) was added to quench the reaction. Ethyl acetate (50 mL×3) was added for extraction. The organic phases were combined, dried over anhydrous sodium sulfate and filtered. The filtrate was concentrated under reduced pressure and subjected to silica gel column chromatography (ethyl acetate: petroleum ether=1:5) to afford Comparative Example 36 compound (0.80 g, light yellow solid).

Comparative Example 37

Comparative Example 37

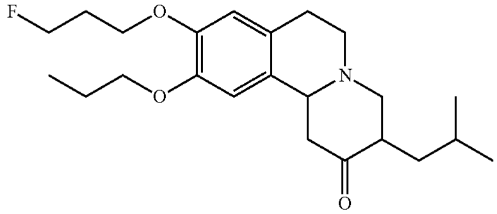

Synthetic Route:

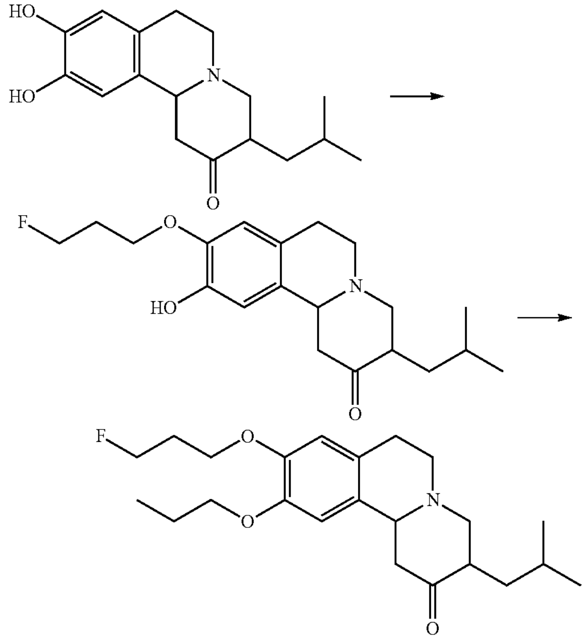

1. 3-Isobutyl-9,10-dihydroxyl-1,3,4,6,7,11b-hexahydro-2H-pyrido[2,1-a] isoquinolin-2-one (0.50 g, 1.73 mmol) was dissolved in N,N-dimethylformamide (5 mL). Potassium carbonate (0.24 g, 1.73 mmol) was added and stirred for 30 minutes. 3-Fluorobromopropane (0.24 g, 1.73 mmol) was added. Under the protection of nitrogen, the mixture was warmed to 80° C. and reacted for 8 hours with stirring. The reaction solution was cooled to room temperature. Water (20 mL) was added to quench the reaction. Ethyl acetate (30 mL×3) was added for extraction. The organic phases were combined, dried over anhydrous sodium sulfate and filtered. The filtrate was concentrated under reduced pressure and subjected to silica gel column chromatography (ethyl acetate: petroleum ether 1:10) to afford 3-isobutyl-9-3'-fluoropropoxy-10-hydroxyl-1,3,4,6,7,11b-hexahydro-2H-pyrido[2,1-a]isoquinolin-2-one (0.42 g, colorless liquid).

2. 3-Isobutyl-9-3'-fluoropropoxy-10-hydroxyl-1,3,4,6,7,11b-hexahydro-2H-pyrido[2,1-a]isoquinolin-2-one (0.07 g, 0.20 mmol) was dissolved in N,N-dimethylformamide (5 mL). Potassium carbonate (0.06 g, 0.40 mmol) was added and stirred for 30 minutes. 1-Bromopropane (0.037 g, 0.30 mmol) was added. Under the protection of nitrogen, the mixture was warmed to 80° C. and reacted for 8 hours with stirring. The reaction solution was cooled to room temperature. Water (20 mL) was added to quench the reaction. Ethyl acetate (30 mL×3) was added for extraction. The organic phases were combined, dried over anhydrous sodium sulfate and filtered. The filtrate was concentrated under reduced pressure and subjected to silica gel column chromatography (EA:PE=1:5) to afford Comparative Example 37 compound (0.04 g, white solid). MS m/z (ESI): 392.3 $[M+H]^+$; $^1$H-NMR (600 MHz, $CDCl_3$) δ 6.67 (s, 1H), 6.61 (s, 1H), 4.77-4.69 (t, J=5.8 Hz, 1H), 4.68-4.60 (t, J=5.8 Hz, 1H), 4.17-4.05 (m, 2H), 3.84-3.73 (m, 2H), 3.54-3.38 (m, 1H), 3.34-3.23 (m, 1H), 3.17-2.93 (m, 2H), 2.93-2.83 (m, 1H), 2.78-2.67 (m, 2H), 2.66-2.48 (m, 2H), 2.35 (t, J=11.6 Hz, 1H), 2.25-2.13 (m, 2H), 1.86-1.74 (m, 1H), 1.73-1.61 (d, J=6.4 Hz, 1H), 1.32-1.20 (m, 1H), 1.08-0.98 (m, 1H), 0.97-0.84 (m, 6H), 0.39-0.29 (m, 3H).

Comparative Example 38

Step 1: Synthesis of Fragment 2

Fragment 2

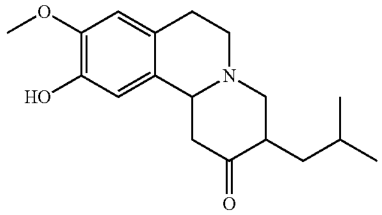

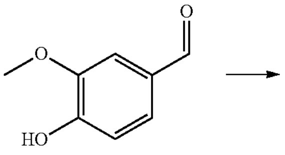

g

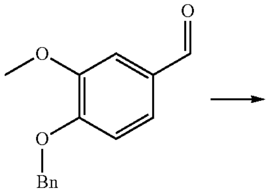

h

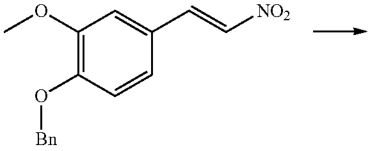

i

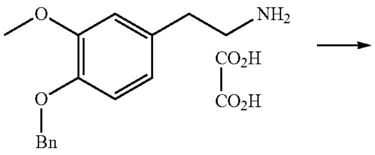

j

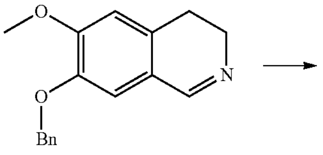

k

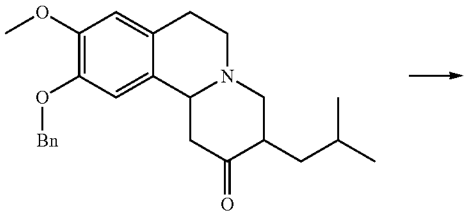

l

-continued

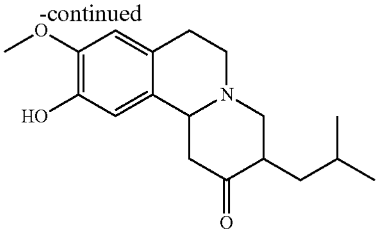

Fragment 2

1. 50 g of compound g was dissolved in DMF (150 mL). Benzyl bromide (57.3 g) and potassium carbonate (68.2 g) were added. Under the protection of nitrogen, the mixture was reacted at room temperature for 6 h. As it was detected by TLC, the reactants disappeared. Ice water was poured into the system and extracted with ethyl acetate 3 times. The organic phases were combined, washed with brine twice, dried over anhydrous sodium sulfate, filtered and concentrated to afford 67.87 g of product h as a light yellow solid, which was directly used in the next step.

2. To 67.78 g of compound h, nitromethane (100 mL) and ammonium acetate (13.9 g) were added, and the mixture was heated to 112° C. and reacted for 4 h. As it was found by TLC detection, the reactants disappeared. The temperature was reduced and nitromethane was removed by evaporation. The residue was washed with water and extracted with ethyl acetate twice. The organic phase was dried over anhydrous sodium sulfate, filtered and concentrated to afford 77 g of yellow solid i. The yellow solid i was used in the next step.

3. 30 g of lithium aluminum hydride was dissolved in THF (300 mL). The mixture was cooled to 0° C. 77 g of compound i was dissolved in tetrahydrofuran. The resulting mixture was slowly added dropwise into a reaction vial. After the addition, the reaction mixture was refluxed at 72° C. for 3 h. As it was found by TLC detection, the reactants disappeared. The temperature was reduced to 0° C. Water (30 mL), 10% sodium hydroxide solution (60 mL), and water (90 mL) were slowly and successively added. The mixture was suction filtered and the filter cake was washed with tetrahydrofuran twice. The organic phases were combined. The organic phase was evaporated to dryness to afford 79.8 g of a brown oily liquid. The brown oily liquid was dissolved with acetone. The mixture was adjusted to pH=3 by adding oxalic acid and a solid was precipitated and suction filtration was performed to afford 40 g of compound j as a yellowish white solid. The compound j was used in the next step.

4. 2.9 g of compound j was dissolved in acetic acid (30 mL). Trifluoroacetic acid (10 mL) and urotropine (3.3 g) were added. The mixture was heated to 85° C. and reacted for 4 h. As it was found by TLC detection, the reactants disappeared. The temperature was reduced. Acetic acid and trifluoroacetic acid were removed by evaporation. Water was added to the residue. Sodium hydroxide aqueous solution was used to adjusted pH to 9 and ethyl acetate was used for extraction 3 times. The organic phase was dried over anhydrous sodium sulfate, filtered and concentrated to afford 2.9 g of a brown oily liquid k, which was directly used in the next step.

5. 39.2 g of compound k was dissolved in a mixed solution of ethanol (100 mL) and water (100 mL). 3-dimethylamino-5-methyl-2-hexanone (27.6 g) and benzyltriethylammonium chloride (10.1 g) were added and the mixture was heated to 95° C. and reacted for 16 h. As it was found by TLC detection, the reactants disappeared. The temperature was reduced. Ethanol was removed by evaporation. The residue was extracted with ethyl acetate 3 times. The organic phase was dried over anhydrous sodium sulfate, filtered and concentrated to afford product as a brown oily liquid. The product was dissolved with acetone and adjusted to pH=3 by adding p-toluenesulfonic acid. A solid was precipitated and suction filtration was performed to afford 12.7 g of a yellowish white solid 1, which was used in the next step.

6. 1.5 g of compound I was dissolved in methanol solution (20 mL). Two spoons of palladium on carbon were added. The mixture was reacted at ambient temperature under an atmosphere of hydrogen gas for 10 h. As it was found by TLC detection, the reactants disappeared. The reactant was suction filtered and the filter cake was washed with methanol twice. The organic phases were combined. The combined organic phase was evaporated to dryness to afford 1.08 g of a light yellow solid, i.e., fragment 2.

Step 2:

Comparative Example 38

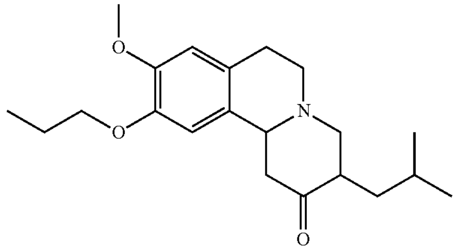

Synthetic Route:

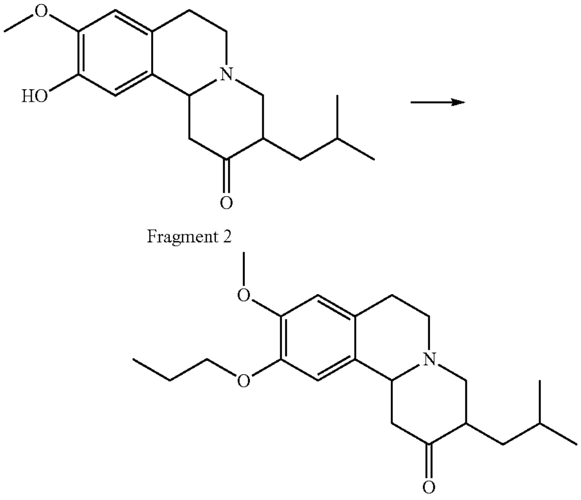

Comparative Example 38

0.2 g of Fragment 2 was dissolved in DMF (5 mL). 1-Bromopropane (0.08 g) and potassium carbonate (0.14 g) were added. Under the protection of nitrogen, the mixture was heated to 70° C. and reacted for 3 h. As it was found by TLC detection, the reactants disappeared. The temperature was reduced. Ice water was added to the system and extracted with ethyl acetate 3 times. The organic phases were combined, washed with brine twice, dried over anhydrous sodium sulfate, filtered and concentrated to afford 0.15 g of a white solid product, i.e., Comparative Example 38 compound.

Comparative Example 39

Comparative Example 39

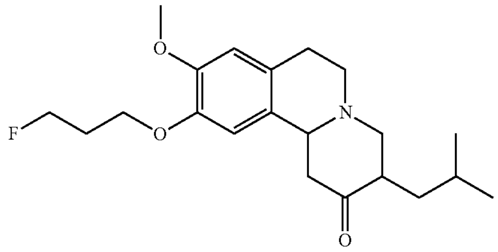

Synthetic Route:

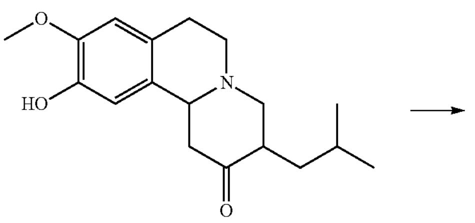

Fragment 2

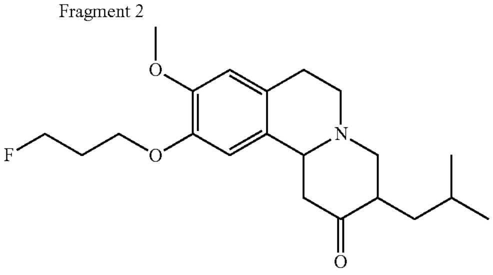

Comparative Example 39

0.2 g of Fragment 2 compound was dissolved in DMF (5 mL). 1-Bromo-3 fluoropropane (0.08 g) and potassium carbonate (0.14 g) were added. Under the protection of nitrogen, the mixture was heated to 70° C. and reacted for 3 h. As it was found by TLC detection, the reactants disappeared. The temperature was reduced. Ice water was added into the system and extracted with ethyl acetate 3 times. The organic phases were combined, washed with brine twice, dried over anhydrous sodium sulfate, filtered, concentrated and subjected to column purification to afford a product (0.15 g) as a white solid, with a yield of 84.5%, MS (ESI): 364 $[M+H]^+$; $^1H$ NMR (400 MHz, $CDCl_3$) 6.63 (s, 1H), 6.60 (s, 1H), 4.68-4.70 (m, 1H), 4.60-4.62 (m, 1H), 4.08-4.10 (m, 2H), 3.84 (s, 3H), 3.83-3.84 (m, 1H), 3.48-3.50 (m, 1H), 3.28-3.29 (m, 2H), 2.87-2.89 (m, 1H), 2.52-2.75 (m, 4H), 2.34-3.35 (m, 1H), 2.21-2.23 (m, 2H), 1.78-1.82 (m, 1H), 1.65-1.67 (m, 1H), 1.25-1.28 (m, 1H), 1.01-1.04 (m, 1H), 0.87-0.93 (m, 6H).

Comparative Example 40

Comparative Example 40

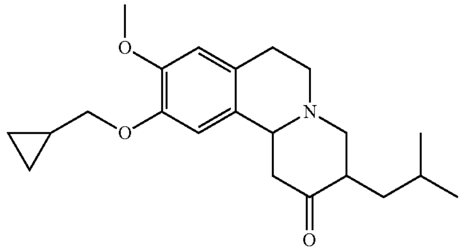

Synthetic Route:

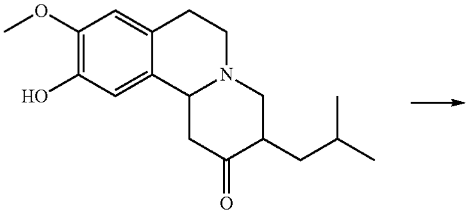

Fragment 2

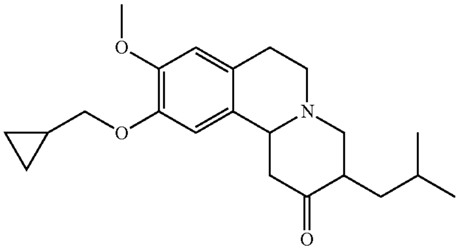

Comparative Example 40

Fragment N compound (0.2 g) was dissolved in DMF (5 mL). Bromomethylcyclopropane (0.08 g) and potassium carbonate (0.14 g) were added. Under the protection of nitrogen, the mixture was heated to 70° C. and reacted for 3 h. As it was found by TLC detection, the reactants disappeared. The temperature was reduced. Ice water was added to the system and extracted with ethyl acetate 3 times. The organic phases were combined, washed with brine twice, dried over anhydrous sodium sulfate, filtered and concentrated to afford 0.15 g of Comparative Example 40 compound as a white solid. MS m/z (ESI): 358.3 $[M+H]^+$; 1HNMR (400 MHz, $CDCl_3$) 6.62 (s, 1H), 6.57 (s, 1H), 3.85 (s, 3H), 3.78-3.79 (, 2H), 3.48-3.50 (m, 1H), 3.28-3.29 (m, 1H), 3.11-3.14 (m, 2H), 2.86-2.89 (m, 1H), 2.52-2.75 (m, 4H), 2.35 (m, 1H), 1.78-1.80 (m, 1H), 1.26-1.31 (m, 2H), 1.02-1.05 (m, 1H), 0.87-0.93 (m, 6H), 0.61-0.64 (m, 2H), 0.32-0.35 (m, 2H).

Comparative Example 41

Step 1: Synthesis of Fragment 3

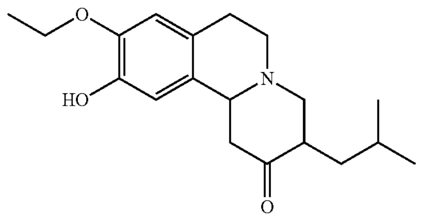

Fragment 3

Synthetic Route:

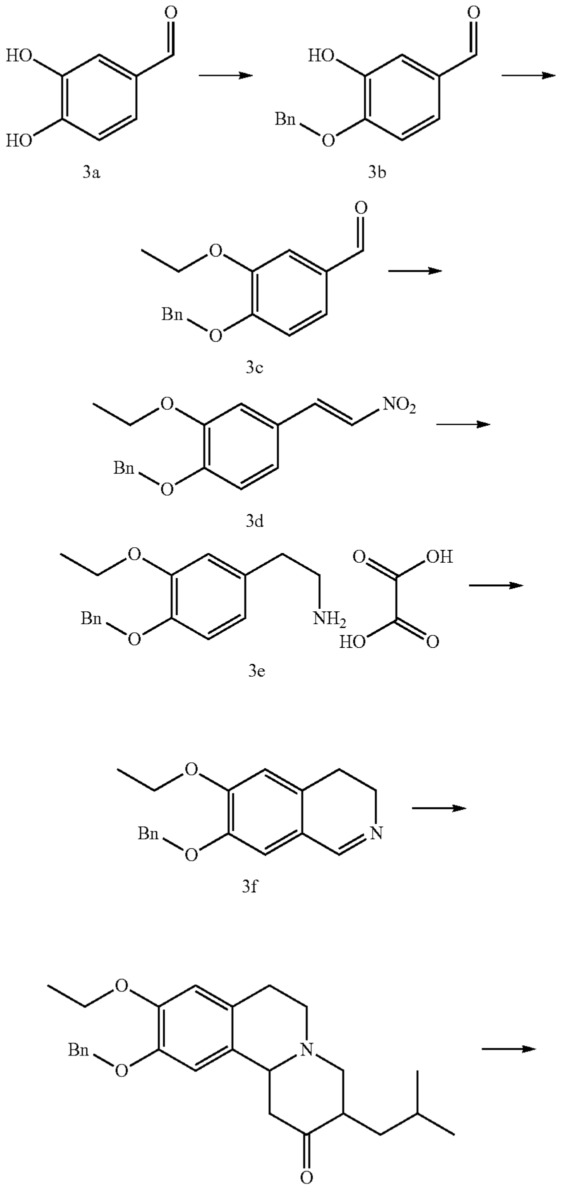

3a 3b 3c 3d 3e 3f 3g

-continued

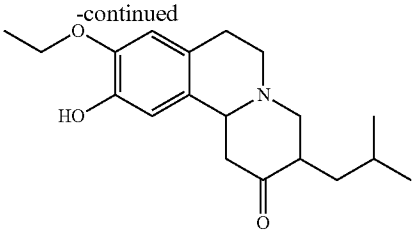

Fragment 3

1. Compound 3a (10.0 g, 72.5 mmol) was dissolved in DMF (100 mL). Potassium carbonate (15.0 g, 109 mmol) and benzyl bromide (18.6 g, 109 mmol) were added. The mixture was warmed to 85° C. and reacted for 8 h. The reaction solution was cooled to room temperature. Ice water (500 mL) was added into the reaction solution to precipitate a solid which was filtered out and dried to afford compound 3b (9.92 g, white solid).

2. Compound 3b (9.92 g, 43.5 mmol) was dissolved in DMF (50 mL). Bromoethane (7.11 g, 65.2 mmol) and potassium carbonate (9.00 g, 65.2 mmol) were added. The mixture was warmed to 80° C. and reacted for 5 h. After cooling, the reaction system was poured into water (500 mL) and then extracted with ethyl acetate (200 mL*3). The organic phases were combined, dried over anhydrous sodium sulfate and filtered. The filtrate was concentrated under reduced pressure and the residue was slurried with petroleum ether (150 mL). The mixture was filtered and the solid was collected to afford compound 3c (10.0 g, off-white solid).

3. Compound 3c (10.0 g, 39.1 mmol) was dissolved in nitromethane (50 mL). Ammonium acetate (1.81 g, 23.5 mmol) was added. The mixture was heated to 115° C. and reacted for 3 h. After cooling, the reaction mixture was concentrated. The residue was washed with water and extracted with ethyl acetate (100 mL*3). The organic phases were combined, dried over anhydrous sodium sulfate, filtered and concentrated to afford compound 3d (11.6 g, yellow solid).

4. Under the protection of nitrogen and ice-bath, compound 3d (11.6 g, 38.8 mmol) was dissolved in anhydrous THF (100 mL), and the mixture was added dropwise to a solution of lithium aluminum hydride (4.42 g, 116 mmol) in anhydrous THF (100 mL) and reacted for 1 h. The mixture was then warmed to 60° C. and reacted for another 2 h. The temperature was reduced in an ice bath. Water (4.4 mL) was added dropwise and then 10% sodium hydroxide solution (8.8 mL) and water (13.2 mL) were added. The mixture was suction filtered and then the filter cake was washed with ethyl acetate (150 mL*3). The filtrate was concentrated under reduced pressure. The concentrate was diluted with ethyl acetate. A solution of oxalic acid in ethyl acetate was added until the pH value showed to be acidic. The mixture was stirred overnight. The mixture was filtered and the filter cake was collected and washed with ethyl acetate (100 mL*3) to afford compound 3e (11.2 g, white solid).

5. Compound 3e (11.2 g, 31.0 mmol) was dissolved in acetic acid (100 mL). The resulting mixture was added into trifluoroacetic acid (30 mL). Urotropine (9.55 g, 68.2 mmol) was added, heated to 85° C. and reacted for 4 h. The reaction mixture was cooled to room temperature and concentrated. Water was added to the residue. The resulting mixture was adjusted to pH=9 with sodium hydroxide aqueous solution, and extracted with ethyl acetate (100 mL*3). The organic phases were combined, dried over anhydrous sodium sulfate, filtered and concentrated to afford compound 3f (8.71 g, brown oil, crude), which was directly used in the next step without purification.

MS m/z (ESI): 282.2 $[M+H]^+$

6. Compound 3f (8.71 g, 31.0 mmol) was dissolved in a mixed solution of ethanol (100 mL) and water (100 mL). 3-Dimethylamino-5-methyl-2-hexanone (6.36 g, 37.2 mmol) and benzyltriethyl ammonium chloride (2.12 g, 9.30 mol) were added. The mixture was heated to 95° C. and reacted for 18 h. The reaction mixture was cooled to room temperature and concentrated. The residue was extracted with ethyl acetate (150 mL*3). The organic phases were combined, dried over anhydrous sodium sulfate, filtered, concentrated under reduced pressure, and separated by column chromatography (petroleum ether: ethyl acetate=5:1) to afford compound 3g (3.78 g, off-white solid). MS m/z (ESI): 408.3 $[M+H]^+$ 7. Compound 3g (3.78 g, 9.30 mmol) was dissolved in methanol solution (50 mL). Palladium on carbon containing water (10%, 0.5 g) was added, and hydrogen was introduced. The mixture was reacted at room temperature for 18 h. The mixture was suction filtered and the filter cake was washed with methanol (50 mL*2), concentrated under reduced pressure and separated by column chromatography (petroleum ether:ethyl acetate=2:1) to afford fragment 3 (2.50 g, off-white solid). MS m/z (ESI): 318.2 $[M+H]^+$ Step 2:

Comparative Example 41

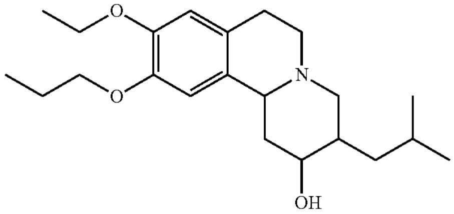

Synthetic Route:

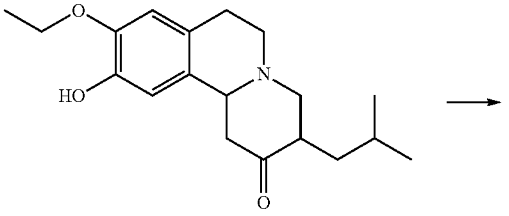

Fragment 3

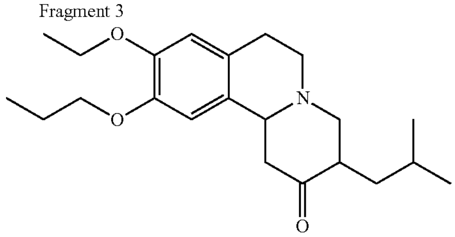

Comparative Example 41

1. Fragment 3 compound (200 mg, 0.631 mmol) was dissolved in DMF (5 mL). Bromopropane (116 mg, 0.946 mmol) and potassium carbonate (130 mg, 0.946 mmol) were added. The mixture was warmed to 80° C. and reacted for 5 h. After cooling, the reaction system was poured into water (30 mL) and then extracted with ethyl acetate (20 mL*3). The organic phases were combined and dried over anhydrous sodium sulfate and filtered. The filtrate was concentrated under reduced pressure and separated by column chromatography (petroleum ether:ethyl acetate=4:1) to afford Comparative Example 41 compound (182 mg, off-white solid). MS m/z (ESI): 360.2 [M+1]

Comparative Example 42

Comparative Example 42

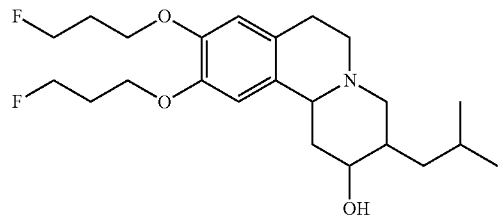

Synthetic Route:

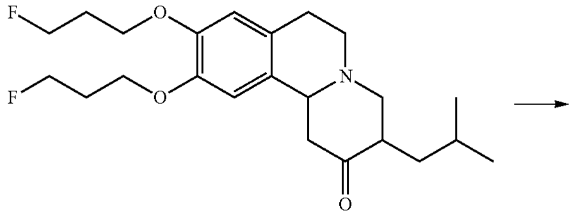

Comparative Example 38

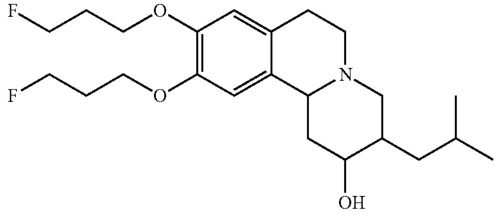

Comparative Example 42

Comparative Example 36 compound (0.80 g, 2.00 mmol) was dissolved in anhydrous ethanol (30 mL). At 0° C., sodium borohydride (0.15 g, 4.00 mmol) was added in portions. The mixture was reacted at 0° C. for 2 hours with stirring. Saturated ammonium chloride solution (6 mL) was added to quench the reaction. The reaction solution was filtered and the filtrate was concentrated under reduced pressure and subjected to silica gel column chromatography (dichloromethane:methanol=10:1) to afford 0.75 g of a light yellow solid compound. MS m/z (ESI): 412.3 $[M+H]^+$; 1HNMR (600 MHz, $CD_3OD$) δ 6.82 (s, 1H), 6.72 (s, 1H), 4.71-4.63 (m, 2H), 4.63-4.53 (m, 2H), 4.11-4.01 (m, 4H), 3.23-3.14 (m, 1H), 3.11-2.99 (m, 3H), 2.73-2.64 (m, 1H), 2.60-2.52 (m, 1H), 2.52-2.43 (m, 1H), 2.19-2.06 (m, 4H), 2.07-1.97 (m, 1H), 1.78-1.61 (m, 3H), 1.52-1.38 (m, 1H), 1.08-0.99 (m, 1H), 0.98-0.86 (m, 6H).

Comparative Examples 43-44

With regard to the preparation of Comparative Examples 43-44, reference could be made to the method of Comparative Example 42 and the compounds of Comparative Examples 43-44 were prepared by reduction with a solution of ethanol and sodium borohydride.

TABLE 24

| Structure and characterization data of Comparative Examples 43-44 | | |
|---|---|---|
| Comparative Example | Structural formula | Spectra |
| 43 | 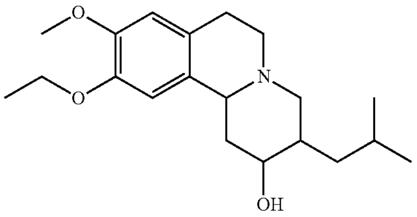 [SMILES: CCOc1cc2c(cc1OC)CCN1CC(CC(C)C)C(O)CC21] | MS m/z (ESI): 334.2 $[M+H]^+$ $^1H$ NMR (600 MHz, Chloroform-d) δ 0.88-0.99 (m, 6H), 1.02-1.12 (m, 1H), 1.41-1.48 (m, 3H), 1.47-1.64 (m, 3H), 1.65-1.82 (m, 2H), 1.94-2.05 (m, 1H), 2.42-2.74 (m, 3H), 2.96-3.21 (m, 4H), 3.35-3.44 (m, 1H), 3.80-3.88 (s, 3H), 4.01-4.14 (m, 2H), 6.61 (s, 1H), 6.72 (s, 1H) |
| 44 | 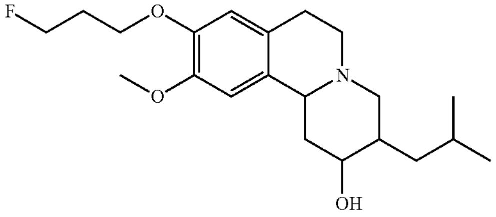 [SMILES: COc1cc2c(cc1OCCCF)CCN1CC(CC(C)C)C(O)CC21] | MS m/z (ESI): 366.2 $[M+H]^+$ $^1H$ NMR (400 MHz, $CD_3OD$) δ 6.81 (s, 1H), 6.72 (s, 1H), 4.56-4.71 (m, 2H), 3.81 (s, 3H), 2.91-3.22 (m, 4H), 2.38-2.71 (m, 3H), 1.99-2.27 (m, 2H), 1.31-1.81 (m, 6H), 1.02-1.11 (m, 1H), 0.94-0.98 (m, 6H). |

Comparative Example 45

Comparative Example 45

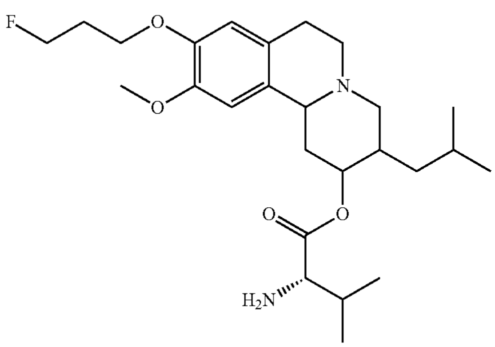

Synthetic Route:

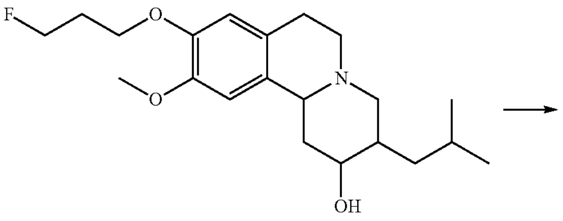

Comparative Example 44

-continued

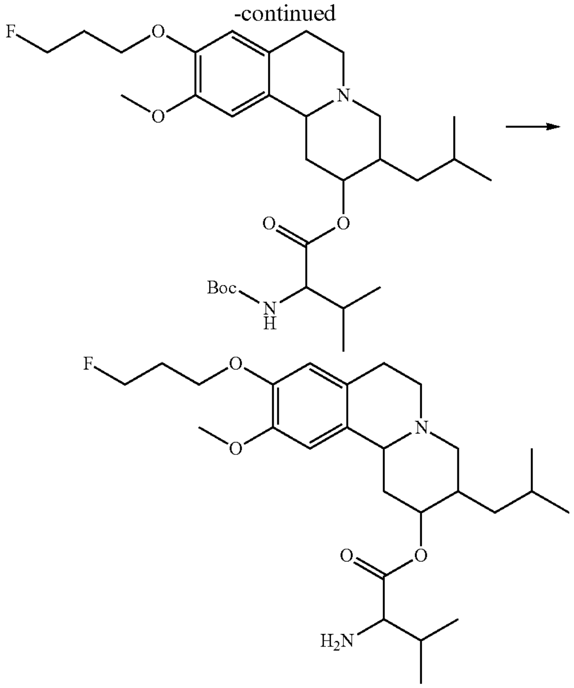

Comparative Example 45

1. Under the protection of nitrogen, Boc-L-valine (651 mg, 3 mmol) was dissolved in dichloromethane (15 mL) under ice-bath. 4-Dimethylamino pyridine (293 mg, 2.4 mmol) and Comparative Example 7 compound (760 mg, 1.83 mmol) were added and the mixture was reacted for 5 minutes with stirring under ice-bath. Dicyclohexylcarbodiimide (618 mg, 3 mmol) was added in one portion. The mixture was allowed to naturally warm up and reacted for 18 hours. The resulting mixture was filtered and the filtrate was concentrated under reduced pressure. The resulting residue was separated and purified by column chromatography (dichloromethane:methanol=30:1) to afford an intermediate compound (780 mg, off-white solid).

MS m/z (ESI): 565.4 [M+1]

2. The compound obtained in the previous step (780 mg, 1.38 mmol) was dissolved in dichloromethane (10 ml). The resulting mixture was added into 1,4-dioxane solution (1.7 ml, at the concentration of 4M) and reacted at room temperature for 2 hours. The reaction solution was concentrated. The solid was washed with diethyl ether (10 ml*1) to afford a crude. The crude was dissolved in water (30 mL). The mixture was adjusted with saturated sodium bicarbonate aqueous solution to pH=7-8 and extracted with dichloromethane (10 ml*3). The organic phases were combined. The dichloromethane phase was washed with water (10 ml*1) and saturated sodium chloride (10 ml*1), respectively. The dichloromethane phase was dried over anhydrous sodium sulfate. Filtration was performed to remove the solid. The dichloromethane phase was concentrated to afford Comparative Example 45 compound (500 mg, off-white solid). MS m/z (ESI): 465.4 $[M+H]^+$; $^1H$ NMR (400 MHz, $CD_3OD$) δ 6.73-6.75 (m, 2H), 4.56-4.77 (m, 3H), 4.08-4.11 (m, 2H), 3.80 (s, 3H), 3.05-3.32 (m, 4H), 2.50-2.75 (m, 3H), 2.01-2.21 (m, 5H), 1.33-1.77 (m, 3H), 1.06-1.13 (m, 2H), 0.93-1.05 (m, 12H).

Experimental Example 1 Biological Activity Experiment

I. Radioactivity Detection of Activity of Compounds Binding to VMAT2 in Rats (Binding assay)

1. Experiment Objective:

To determine the $IC_{50}$ and Ki values of the binding of various compounds to VMAT2 in rats and to evaluate the affinity of compounds for VMAT2.

2. Experiment Materials

Ligand: [3H] Dihydrotetrabenazine (DHTBZ) (10 nM)

Test Compounds:

compounds 1-9, 11, 12, 14, 16-19, 20, 27, 28, 32, 11-P3, 11-P4, and 21-P3: prepared according to corresponding Examples above Comparative Examples 35-43 compounds: prepared according to Comparative Examples 35-43

TBZ: Jiangsu Vcare Pharmatech Co., Ltd., Lot No.: TBZ-113030

DHTBZ: Jiangsu Vcare Pharmatech Co., Ltd., Lot No.: 67-25-1521-59C

DHTBZ-X (racemate): prepared according to Reaction Scheme 1 in WO 2008058261, with TBZ as the raw material VBZ: prepared according to the following method: VBZ xylene sulfonate (0.5 g, 0.65 mmol) was dissolved in water (10 mL). The mixture was adjusted to pH=8 or so with saturated $NaHCO_3$ solution and extracted with EA (20 mL*3). The organic phases were combined, dried over anhydrous sulfuric acid and concentrated to afford VBZ (0.26 g) as a white solid.

3. Experiment Steps and Method 3.1 Preparation of Rat Cerebral Vesicle Membrane

Male Wistar rat, weighing 175±25 g, was selected and the whole brain (without the cerebellum) of the rat was isolated surgically and placed into a pre-chilled sucrose solution (20 mL, 0.32 M) and homogenized by a Teflon pestle homogenizer. The homogenate was centrifuged at 1000 g for 12 min at 4° C.; The supernatant was aspirated and centrifugation was carried out at 22,000 g for another 10 min at 4° C. The supernatant was discarded and the precipitate obtained was placed in ice cold MilliQ water (18 mL, Millipore Corporation, Billerica, MA), incubated for 5 minutes and subjected to osmotic shock to shatter cell membrane. Then osmolarity was restored by addition of HEPES solution (25 mM, 2 mL) and potassium tartrate solution (100 mM, 2 mL). The resulting sample was centrifuged at 20,000 g for 20 min at 4° C. The supernatant was aspirated and MgSO4 solution (1 mM, 20 μL) was added. The solution was centrifuged at 100,000 g for 45 min at 4° C. The precipitate was collected and resuspended in ice cold assay buffer (25 mM HEPES, 100 mM potassium tartrate, 5 mM $MgSO_4$, 0.1 mM EDTA and 0.05 mM EGTA, pH 7.5) to obtain a vesicle suspension.

3.2 Detection and Analysis

A 96-well plate was used in the detection and 2 or 3 duplicate wells were arranged. Vesicle suspension (50 μL, containing protein (32 μg)), [3H] dihydrotetrabenazine (DHTBZ) (10 nM), and a solution containing a test compound (50 μL) (the inhibitor is at a concentration of 1 nM-1000 nM, or other desired concentration) were added into each well of the 96-well plate and incubated at 25° C. for 30 min. Non-specific ligand Ro4-1284 (10 μM) was used to determine and predict non-specific binding and tetrabenazine (TBZ), DHTBZ, VBZ or DHTBZ racemate having definite pharmacological characteristics were used as positive controls and used to compare with the activity of the new compounds. After completion of the incubation, the reaction solution was filtered (bacteria filter and collector, PerkinElmer Life and Analytical Sciences) to a filter plate and subsequently, the filter membrane was washed with 350 μL of ice-cold buffer (25 mM HEPES, 100 mM potassium tartrate, 5 mM $MgSO_4$ and 10 mM NaCl, pH 7.5) five times. The filter plate was dried and had the bottom sealed. 40 μL of scintillation cocktail (MicroScint 20; PerkinElmer Life and Analytical Sciences) was added to each well. Radioactivity on the filter was determined by liquid scintillation spectrometry (TopCount NXT; PerkinElmer Life and Analytical Sciences).

3.3 Result Analysis

Based on the radioactivity assay results above, $IC_{50}$ and Ki were calculated. $IC_{50}$ was calculated by a non-linear, least squares regression analysis using MathIQ™ (ID Business Solutions Ltd., UK). Ki values were calculated using the equation of Cheng and Prusoff (Cheng, Y., Prusoff, W. H., Biochem. Pharmacol. 22:3099-3108, 1973). Ki values were calculated in combination with the $IC_{50}$ of the test compound and the historical KD in the radioactivity detection method of Eurofins Panlabs company.

Binding inhibition rate, $IC_{50}$ values and Ki values of some Example compounds and Comparative Example compounds were tested at 20 nM and 100 nM by using the methods above and the results could be seen in Tables 25-27.

TABLE 25

Binding inhibition rate data of some Example compounds in the present invention

| Compound | % Binding inhibition rate at 20 nM | % Binding inhibition rate at 100 nM | $IC_{50}$ (nM) |
|---|---|---|---|
| TBZ | 50 | 77 | 23 |
| DHTBZ | 64 | 82 | 10.9 |
| Example 1 | 29 | 70 | 45 |
| Example 2 | 74 | 87 | 6.27 |

TABLE 25-continued

Binding inhibition rate data of some Example compounds in the present invention

| Compound | % Binding inhibition rate at 20 nM | % Binding inhibition rate at 100 nM | $IC_{50}$ (nM) |
|---|---|---|---|
| Example 3 | 74 | 84 | 3.37 |
| Example 4 | 87 | 93 | 0.98 |
| Example 5 | 75 | 94 | 10.6 |
| Example 6 | 77 | 100 | 5.13 |
| Example 7 | 72 | 95 | 5.40 |
| Example 8 | 43 | 85 | 23 |
| Example 9 | 76 | 97 | 6.03 |
| Example 16 | 65 | 84 | 12.9 |
| Example 17 | 28 | 71 | 58 |
| Example 19 | 74 | 94 | 5.99 |
| Example 20 | 68 | 102 | 4.90 |
| Comparative Example 35 | 15 | 36 | 190 |
| Comparative Example 36 | 17 | 22 | >500 |
| Comparative Example 37 | 11 | 24 | >500 |
| Comparative Example 38 | 2 | 5 | >500 |
| Comparative Example 39 | 11 | 20 | >500 |
| Comparative Example 40 | 1 | 2 | >500 |
| Comparative Example 41 | 22 | 29 | 280 |
| Comparative Example 42 | 11 | 3 | >500 |
| Comparative Example 43 | 6 | 22 | >500 |

TABLE 26

Binding inhibition rate data of some Example compounds in the present invention

| Compound | $IC_{50}$ | Ki |
|---|---|---|
| DHTBZ | 7.23 nM | 4.22 nM |
| VBZ | >0.5 μM | Not determined |
| 11 | 5.45 nM | 3.18 nM |
| 11-P3 | 0.47 μM | 0.27 μM |
| 11-P4 | 2.54 nM | 1.48 nM |
| 21-P3 | 0.18 μM | 0.11 μM |

TABLE 27

Binding inhibition rate data of some Example compounds in the present invention

| Compound | $IC_{50}$ (nM) | Ki (nM) |
|---|---|---|
| DHTBZ-X | 21 | 12.3 |
| 11 | 6.13 | 3.57 |
| 12 | 3.78 | 2.21 |
| 14 | 10 | 5.83 |
| 18 | 3.55 | 2.07 |
| 19 | 2.30 | 1.34 |
| 27 | 2.06 | 1.20 |
| 28 | 7.70 | 4.49 |
| 32 | 1.29 | 0.75 |

Experimental results showed: compared to TBZ, DHTBZ, DHTBZ-X, VBZ and Comparative Examples compounds, the compounds provided in the present invention had stronger affinity for VMAT. When the group at the 10-position was methyl and the group at the 9-position was ethyl, cyclopropylmethylene and 4-fluorobutyl, the binding inhibition activity was the best; and when the group at the 10-position was long substituents such as propyl and butyl, the binding inhibition activity decreased significantly, or even worse, barely any activity was detected. In addition, when the group at the 9-position was methyl and the group at the 10-position was long substituents such as ethyl, propyl and cyclopropylmethylene, the binding inhibition activity decreased significantly, or even worse, no activity was detected. Namely, the inventors found that the substituents at 9- and 10-position made a significant difference to the activity.

II. Uptake Assay of Compounds and VMAT2

1. Objective

Carry out uptake assay of compound and VMAT2.

2. Materials (1) Reagents and materials 3H-dopamine, sucrose, HEPES, potassium tartrate, EGTA, EDTA, ATP, MgCl2, MgSO4, ascorbic acid, TBZ, BCA Protein Assay Kit Frozen vesicle suspension: vesicle suspension was prepared by extraction using corpus striatum of SD rat. Fresh rat corpus striatum was added into a sucrose solution (0.32 M, 28 mL) under an ice bath and homogenized with a homogenizer 10 times, 10 s per homogenization. At 4° C., the homogenate was centrifuged at 2000 g for 10 min. The supernatant was aspirated and centrifugation was carried out at 4° C. at 10000 g for another 30 min. The precipitate was separated and resuspended in a sucrose solution (4 mL, 0.32 M). MilliQ water (14 mL, under an ice bath) was added and the mixture was subjected to osmotic shock. After 1 min, HEPES buffer (0.25 M, 1.8 mL) and potassium tartrate solution (1 M, 1.8 mL) were added. At 4° C., the mixture was centrifuged at 20000 g for 30 min. The supernatant was collected and centrifugation was carried out at 4° C. at 55000 g for another 60 min. The supernatant was discarded. MgSO4 (200 μL, 10 mM), HEPES (200 μL, 0.25 M) and potassium tartrate (200 μL, 1 M) were added. At 4° C., the mixture was centrifuged at 55000 g for 45 min. The precipitate was collected, resuspended in detection buffer (10 mL, 25 mM HEPES, 100 mM potassium tartrate, 50 μM EGTA, 100 μM EDTA, 20 mM $MgCl_2$, and 2 mM ATP, pH 7.4), sub-packaged at 500 μL/tube and frozen at −80° C. for use.

(2) Buffers

Assay buffer: 25 mM HEPES, 100 mM potassium tartrate, 50 μM EGTA, 100 UM EDTA, 20 mM MgCl2, 1.7 mM ascorbic acid, 2 mM ATP, pH 7.4. Ascorbic acid and ATP were added prior to the assay.

Wash buffer: 25 mM HEPES, 100 mM potassium tartrate, 50 μM EGTA, 100 μM EDTA, pH 7.4.

(3) Test Compounds

Compounds 11-15, 18-20, 26-28, 32, 11-P4, and 21-P3: prepared according to corresponding Examples above DHTBZ, DHTBZ-X, VBZ: same sources as those in the binding assay above (4) Instruments and Consumables Unifilter-96 GF/B filter plate, Perkin Elmer (Cat No. 6005177);

96-well V-bottom polypropylene plate, Agilent (Cat No. 5042-1385);

TopSeal-A sealing film, Perkin Elmer (Cat No. 6050185);

MicroBeta2 (PerkinElmer);

Cell harvester C961961 (Perkin Elmer);

SpectraMax 340PC (Molecular Devices);

3. Test Method (1) The test samples and TBZ were diluted 4 times with DMSO to 8 concentration gradients with the highest concentration at 0.2 mM and the lowest at 1 μM. 1 μl of diluted test compound or TBZ was transferred to the detection plate with a pipette.

(2) TBZ (1 μl, 2 mM) was added to be used as non-specific binding control (LC); and 1 μl of DMSO was used as total binding control (HC).

(3) 100 μl of diluted vesicle suspension (containing 15 μl of stock solution) was added to the 96-well plate and incubated at 37° C. for 15 min.

(4) 3H-Dopamine (17.92 μM) was diluted with assay buffer to 0.2 μM. 3H-Dopamine (100 μl, 0.2 M) was added to the detection plate to achieve a final concentration of 0.1 μM and incubated at 37° C. for 10 min.

(5) The reaction mixture was filtered through the GF/B plate of the harvester and the GF/B plate was rinsed with pre-chilled rinse buffer 4 times.

(6) The plate was dried at 0° C. for at least 1 hr.

(7) After drying, Perkin Elmer Unifilter-96 bottom-sealing tape was used to seal the filter plate. 50 μl of Perkin Elmer Microscint 20 cocktail was added. Perkin Elmer TopSeal-A sealing film was used to seal the top of the filter plate.

(8) Perkin Elmer MicroBeta2 Reader was used to count the number of 3H captured on the filtration membrane.

(9) Data were analyzed with Prism 5.0 software. $IC_{50}$ was calculated using the model "log (Inhibitor) vs. response-Variable Slope" and $IC_{90}$ was calculated using the equation ICanything=$IC_{50}$*(anything/(100−anything))1/slope.

4. Test Results could be Seen in Tables 28-30.

TABLE 28

| Uptake data of some Example compounds in the present invention | | |
|---|---|---|
| Compound | $IC_{50}$ (nM) | $IC_{90}$ (nM) |
| DHTBZ | 12.72 | 148.96 |
| 11 | 6.04 | 45.97 |
| 12 | 16.92 | 67.56 |
| 13 | 5.13 | 110.3 |
| 15 | 4.29 | 48.93 |
| 20 | 5.71 | 23.21 |

TABLE 29

| Uptake data of some Example compounds in the present invention | | |
|---|---|---|
| Compound | $IC_{50}$ (nM) | $IC_{90}$ (nM) |
| DHTBZ | 30.61 | 276.77 |
| VBZ | 313.0 | 2916.82 |
| 11 | 7.891 | 36.68 |
| 11-P3 | 129.10 | 1598.59 |
| 11-P4 | 10.2 | 92.39 |
| 21-P3 | 230.2 | 1314.74 |

TABLE 30

| Uptake data of some Example compounds in the present invention | | |
|---|---|---|
| Compound | $IC_{50}$ (nM) | $IC_{90}$ (nM) |
| DHTBZ-X | 42.29 | 161.34 |
| 12 | 11.95 | 347.66 |
| 14 | 192.80 | 1480.14 |
| 18 | 33.62 | 187.87 |
| 19 | 4.207 | 92.33 |

TABLE 30-continued

| Uptake data of some Example compounds in the present invention | | |
|---|---|---|
| Compound | $IC_{50}$ (nM) | $IC_{90}$ (nM) |
| 26 | 14.39 | 140.82 |
| 27 | 8.99 | 331.52 |
| 28 | 5.93 | 116.78 |
| 32 | 2.100 | 4.37 |

Test results showed that compared to DHTBZ, DHTBZ-X and VBZ, compounds provided in the present invention had stronger in vitro activity.

Experimental Example 2 Pharmacokinetic Assessment of Compounds 11, 16, 21, 22 and 23 and Comparative Examples 44 and 45 in SD Rats 1. Experiment Materials a) Test Compounds Compounds 11, 16, 21-23; Comparative Examples 44 and 45: prepared according to corresponding Examples DHTBZ: Jiangsu Vcare Pharmatech Co., Ltd., Lot No.: 67-25-1521-59C VBZ: prepared according to the method mentioned in Experimental Example 1 b) Vehicle: 20% solutol solution, Solutol lot no.: BCBQ5646V, Sigma company c) Test animal: SD rats, clean-grade, male, weighing about 220 g 2. Method of Pharmacokinetic Test in SD Rats:

Compound 11, compound 16, Comparative Example 44 compound and DHTBZ were administrated by gavage to male SD rats, respectively (4 animals/group). The dosage of administration was 10 μmol/kg. At 0.25, 0.5, 1, 2, 3, 4, 6, 8 and 12 h post-dose, blood samples (about 0.2 mL/time point/rat) were collected to heparinized tubes. Within half an hour after collection, the samples were centrifuged to separate the plasma, which was transferred to 1.5 ml EP tubes and stored at −20° C. for detection.

3. Method for Distribution Test in SD Rat Brain Tissue

VBZ, compound 21, compound 22, compound 23 and Comparative Example 45 compound were administrated by gavage to male SD rats (3 animals/group). The dosage of administration was 12 μmol/kg. At 0.5 h, 2 h and 6 h post-dose, blood samples (about 1 mL/time point/rat) were collected to heparinized tubes. Within half an hour after collection, the samples were centrifuged to separate the plasma, which was transferred to 1.5 ml EP tubes and stored at −20° C. for detection. After the rats were sacrificed, the brain tissues were extracted, washed with normal saline and dried with filter paper. Cerebral vessels were stripped and the remaining brain tissues were weighed and stored at −20° C.

4. Sample Analysis

Method for precipitating proteins was used for the pre-treatment of the samples, which may be briefly described as follows: Protein precipitation was carried out in 25 μL of plasma/50 μL of brain tissue homogenate by using 200 μL/400 μL of acetonitrile containing internal standard, respectively. After high-speed centrifugation, the supernatant was diluted with water (1:1 (V/V)) and loaded for analysis.

At 0.5, 2 and 6 h, the concentrations of VBZ, compound 21, compound 22, compound 23 and Comparative Example 45 compound and the concentrations of their metabolites, i.e., DHTBZ, compound 11, compound 12, compound 13 and Comparative Example 44 compound were determined in SD rat plasma and brain tissue homogenate (normal saline homogenate, 1:4 w/v) by using the LC-MS/MS method, and the ratio of concentration in brain to concentration in plasma at each time point was calculated.

5. Test Results 5.1 Pharmacokinetic Test

Figure 9:
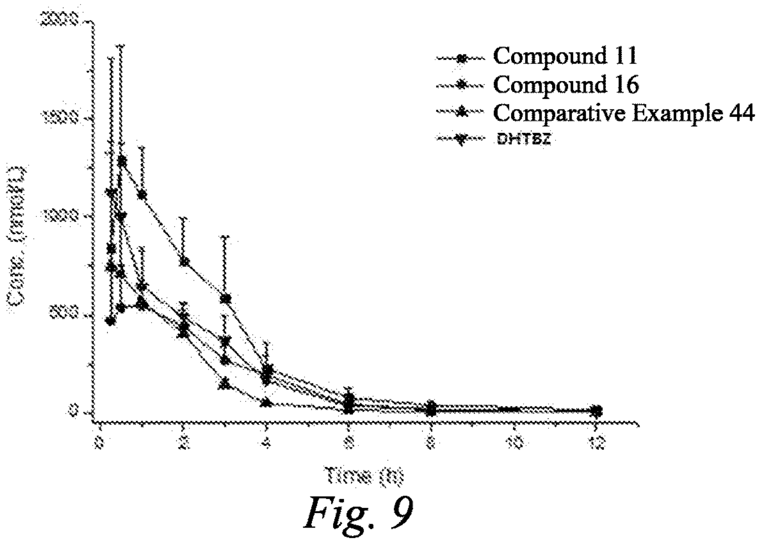
FIG. 9: plasma drug concentration-time curves following gavage administration of compound 11, compound 16, Comparative Example 44 compound and DHTBZ in male SD rats, respectively

Results of tests conducted in SD rats administrated by gavage with compound 11, compound 16, Comparative Example 44 compound and DHTBZ could be seen in FIG. 9 and showed: compared to Comparative Example 44 compound and DHTBZ, compound 11 had higher exposure.

Figure 10:
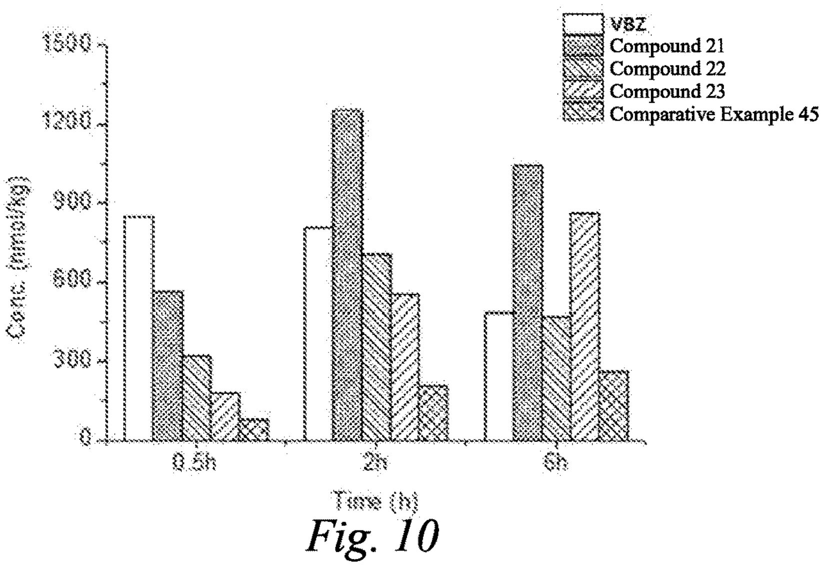
FIG. 10: distribution of original compounds in brain tissue following gavage administration of VBZ, compound 21, compound 22, compound 23 and Comparative Example 45 compound in SD rats
Figure 11:
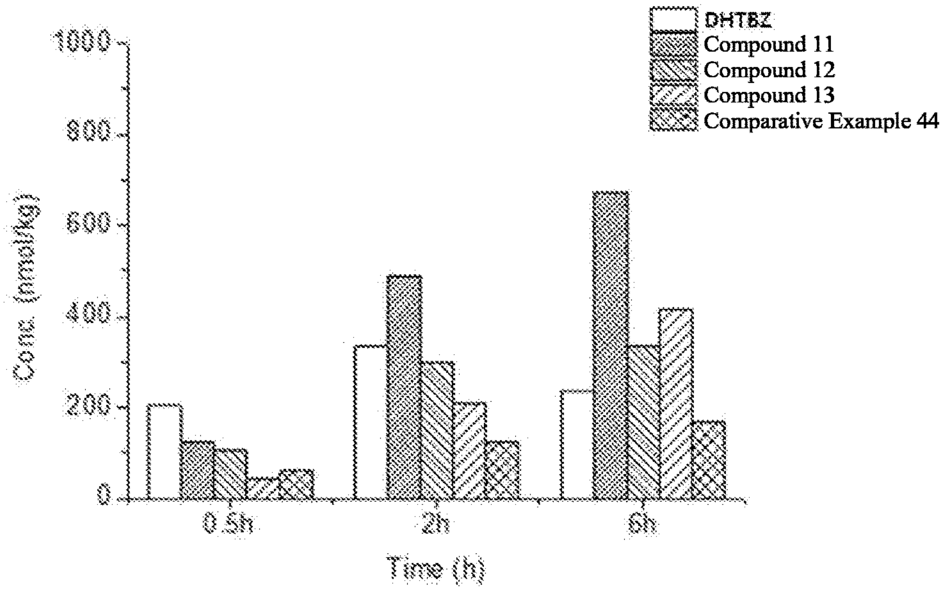
FIG. 11: distribution of active metabolites (DHTBZ, compound 11, compound 12, compound 13 and Comparative Example 44 compound) in brain tissue

5.2 Brain Tissue Distribution Test 5.2.1 Concentration in Brain:

Distribution of original compounds in brain tissue following gavage administration of VBZ, compound 21, compound 22, compound 23 and Comparative Example 45 in SD rats could be seen in FIG. 10; and distribution of active metabolites (DHTBZ, compound 11, compound 12, compound 13 and Comparative Example 44 compound) in brain tissue could be seen in FIG. 11.

Experimental results showed: At 2 h post-dose, the concentrations of compound 21 and its metabolite, compound 11 in brain tissue were both significantly higher than those of VBZ and DHTBZ.

5.2.2 Brain/Plasma Ratio

Figure 12:
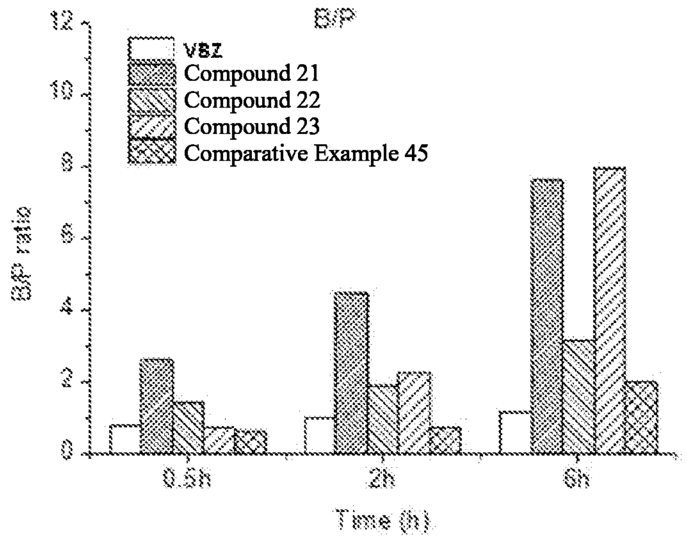
FIG. 12: brain/plasma ratio (B/P ratio) of original compounds following gavage administration of VBZ, compound 21, compound 22, compound 23 and Comparative Example 45 compound in SD rats.

Brain/plasma ratio of original compounds following gavage administration of VBZ, compound 21, compound 22, compound 23 and Comparative Example 45 in SD rats could be seen in FIG. 12; and experimental results showed: at various time points post-dose, the brain/plasma ratio of compound 21 was 3.4-6.8 times that of VBZ and was higher than the brain/plasma ratio of the other compounds.

Figure 13:
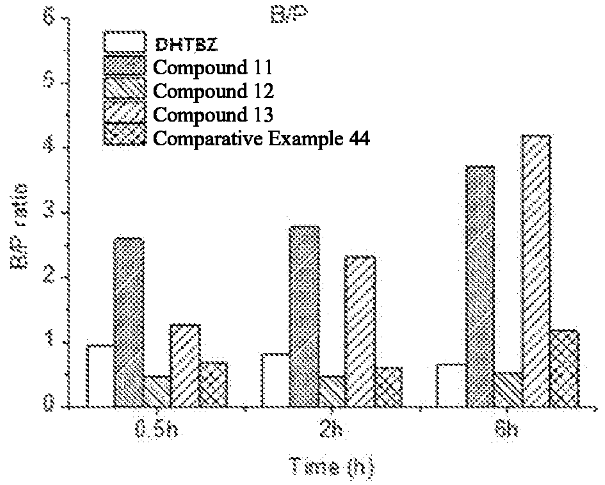
FIG. 13: brain/plasma ratio (B/P ratio) of active metabolites (DHTBZ, compound 11, compound 12, compound 13 and Comparative Example 44 compound)

Brain/plasma ratio of active metabolites (DHTBZ, compound 11, compound 12, compound 13 and Comparative Example 44 compound) following gavage administration of VBZ, compound 21, compound 22, compound 23 and Comparative Example 45 in SD rats could be seen in FIG. 13; and experimental results showed: at various time points post-dose, the brain/plasma ratio of the metabolite of compound 21, i.e., compound 11 was 2.8-5.8 times that of DHTBZ.

Experimental Example 3 Pharmacokinetic Assessment of Compounds 21-P3 and 11-P4 in SD Rats 1. Test Materials:
   a) Test compounds
      11-P4: prepared according to Example 29
      21-P3: prepared according to Example 31
      VBZ: prepared according to the method mentioned in Experimental Example 1
      DHTBZ: Jiangsu Vcare Pharmatech Co., Ltd., Lot No.: 67-25-1521-59C
   b) Vehicle: 20% solutol solution, Solutol lot no.: BCBQ5646V, Sigma company
   c) Test animals: 24 SD rats, clean-grade, male, weighing about 220 g, randomized grouping, 3 rats/group (3 for gavage administration; 3 for intravenous administration).
2. Test Method:

(1) Formulation of medicinal solution: about 20 mg of each of 21-P3, 11-P4, VBZ and DHTBZ was weighed precisely and dissolved with an appropriate amount of vehicle until the concentration of the respective compound was 1 μmol/mL.

(2) Bioavailability test: gavage administration volume was 5 mL/kg, dosage of administration was 5 μmol/kg, and each compound was administrated to 3 animals; intravenous administration volume was 2 mL/kg, dosage of administration was 2 μmol/kg, and each compound was administrated to 3 animals; The SD rats were at a fasted state for 12 h pre-dose but had free access to drinking water, and were fed at 3 h post-dose. At each corresponding time point post-dose, blood samples (about 1 ml/time point/rat) were collected to heparinized tubes. Within half an hour after collection, the samples were centrifuged to separate the plasma, which was transferred to 1.5 ml EP tubes and stored at −20° C. for detection.

3. Sample Analysis

The concentrations of compounds VBZ, DHTBZ, 21-P3 and 11-P4 were determined in SD rat plasma by using the LC-MS/MS method; and for VBZ and 21-P3 administration groups, the concentrations of the respective metabolites DHTBZ and 11-P4 were also determined. Method for precipitating proteins was used for the pretreatment of the samples: protein precipitation was carried out in 25 μL of plasma by using 200 μL of acetonitrile containing internal standard. After high-speed centrifugation, the supernatant was diluted with water (1:1 (V/V)) and injected for analysis.

4. Test Results:

TABLE 31

Average plasma concentration (nmol/L) following gavage administration of different compounds (5 μmol/kg) in SD rats

| | VBZ | | 21-P3 | | | |
|---|---|---|---|---|---|---|
| Time (h) | VBZ | DHTBZ | 21-P3 | 11-P4 | DHTBZ | 11-P4 |
| 0 | BLQ | BLQ | BLQ | BLQ | BLQ | BLQ |
| 0.083 | NA | NA | NA | NA | NA | NA |
| 0.25 | 286.5 | 14.55 | 167.7 | 4.704 | 785.8 | 1918.6 |
| 0.5 | 440.5 | 66.30 | 259.9 | 18.28 | 832.1 | 2658.6 |
| 1 | 346.2 | 124.3 | 408.9 | 71.73 | 687.2 | 1805.5 |
| 2 | 293.4 | 136.3 | 299.6 | 95.43 | 576.5 | 1314.4 |
| 4 | 293.0 | 158.8 | 362.8 | 160.7 | 169.1 | 813.8 |
| 6 | 160.2 | 116.8 | 242.3 | 151.0 | 89.16 | 484.5 |
| 8 | 82.71 | 74.08 | 111.0 | 122.2 | 39.19 | 206.6 |
| 12 | 6.876 | 20.14 | 23.50 | 39.10 | 3.022 | 32.70 |
| 24 | BLQ | BLQ | 5.84 | 9.497 | BLQ | 10.71 |

BLQ represents that no sample was collected at this time point; NA represents that data at this time point is unavailable.

BLQ represents that no sample was collected at this time point; NA represents that data at this time point is unavailable.

TABLE 32

Average plasma concentration (nmol/L) following intravenous administration of different compounds (2 μmol/kg) in SD rats

| | VBZ | | 21-P3 | | | |
|---|---|---|---|---|---|---|
| Time (h) | VBZ | DHTBZ | 21-P3 | 11-P4 | DHTBZ | 11-P4 |
| 0 | BLQ | BLQ | BLQ | BLQ | BLQ | BLQ |
| 0.083 | 2865.5 | 16.15 | 1028.1 | 32.82 | 965.4 | 2405.8 |
| 0.25 | 1774.8 | 54.56 | 572.7 | 31.60 | 773.1 | 1650.1 |
| 0.5 | 1199.9 | 66.04 | 555.3 | 45.02 | 710.2 | 1370.9 |
| 1 | 751.6 | 98.45 | 350.6 | 44.83 | 535.5 | 1127.1 |
| 2 | 258.2 | 95.70 | 279.2 | 54.71 | 220.9 | 644.0 |
| 4 | 109.9 | 68.68 | 121.6 | 61.26 | 70.58 | 236.0 |
| 6 | 56.39 | 29.94 | 93.79 | 47.48 | 26.29 | 104.17 |

TABLE 32-continued

Average plasma concentration (nmol/L) following intravenous administration of different compounds (2 μmol/kg) in SD rats

| | VBZ | | 21-P3 | | | |
|---|---|---|---|---|---|---|
| Time (h) | VBZ | DHTBZ | 21-P3 | 11-P4 | DHTBZ | 11-P4 |
| 8 | 23.29 | 15.86 | 78.27 | 48.55 | 9.63 | 75.81 |
| 12 | 4.190 | 4.183 | 16.24 | 21.13 | 1.706 | 23.85 |
| 24 | BLQ | BLQ | 2.308 | 6.334 | BLQ | 9.883 |

BLQ represents that no sample was collected at this time point; NA represents that data at this time point is unavailable.

BLQ represents that no sample was collected at this time point; NA represents that data at this time point is unavailable.

TABLE 33

Pharmacokinetic parameters following intravenous administration of different compounds (2 μmol/kg) in SD rats

| Group | Compound | $T_{max}$ (h) | $C_{max}$ (nM) | $AUC_{last}$ (h * nM) | $AUC_{inf}$ (h * nM) | $T_{1/2}$ (h) | MRT (h) | Conversion rate* (%) |
|---|---|---|---|---|---|---|---|---|
| VBZ | VBZ | 0.08 | 2865.5 | 2691.7 | 2701.8 | 1.67 | 1.45 | 15.9 |
| | DHTBZ | 1.33 | 100.7 | 508.7 | 521.5 | 2.11 | 3.46 | |
| 21-P3 | 21-P3 | 0.08 | 1028.1 | 1952.1 | 1995.8 | 2.87 | 3.23 | 26.8 |
| | 11-P4 | 3.33 | 65.9 | 713.5 | 768 | 6.05 | 7.47 | |
| DHTBZ | DHTBZ | 0.083 | 965.4 | 1544.4 | 1555.4 | 1.4 | 1.5 | — |
| 11-P4 | 11-P4 | 0.08 | 2405.8 | 4251.6 | 4312.5 | 4.59 | 2.69 | — |

*Conversion rate = Metabolite $AUC_{last}$/(Prototype drug $AUC_{last}$ + Metabolite $AUC_{last}$) × 100%
Intravenous administration conversion rate (VBZ) = 508.7/(508.7 + 2691.7) = 15.9%;
Intravenous administration conversion rate (21-P3) = 713.5/(713.5 + 1952.1) =26.8%

TABLE 34

Pharmacokinetic parameters following gavage administration of different compounds (5 μmol/kg) in SD rats

| Group | Compound | $T_{max}$ (h) | $C_{max}$ (nM) | $AUC_{last}$ (h * nM) | $AUC_{inf}$ (h * nM) | $T_{1/2}$ (h) | MRT (h) | Conversion rate (%) | BA (%) |
|---|---|---|---|---|---|---|---|---|---|
| VBZ | VBZ | 1.67 | 445.4 | 2019.1 | 2032.7 | 1.41 | 3.54 | 35.5 | 39.1 |
| | DHTBZ | 2.67 | 162.4 | 1110.5 | 1179.3 | 2.26 | 4.8 | | |
| 21-P3 | 21-P3 | 3 | 455.6 | 2541.9 | 2582.1 | 2.96 | 4.82 | 36.9 | 60.5 |
| | 11-P4 | 5.33 | 174 | 1488.3 | 1553 | 4.67 | 7.74 | | |
| DHTBZ | DHTBZ | 0.58 | 950.6 | 2381 | 2393.6 | 1.29 | 2.45 | — | 61.7 |
| 11-P4 | 11-P4 | 0.5 | 2658.6 | 8039 | 8085.2 | 2.99 | 3.49 | — | 75.6 |

Gavage administration bioavailability in rats (BA) = Gavage $AUC_{last}$/Intravenous $AUC_{last}$ × 100%
BA(VBZ) = (2019.1 + 1110.5)/(2691.7 + 508.7)/2.5 = 39.1%;
BA(21-P3) = (2541.9 + 1488.3)/(1952.1 + 713.5)/2.5 = 60.5%;
BA(DHTBZ) = 2381/1544.4/2.5 = 61.7%;
BA(11-P4) = 8039/4251.6/2.5 = 75.6%.

The results showed that (1) Compound 11-P4 had significantly increased in vivo exposure (AUC), the exposure of intravenous administration was nearly 3 times that of DHTBZ, and the exposure of gavage administration was nearly 4 times that of DHTBZ;

(2) By intravenous administration, compound 11-P4 had longer half-life and hence the administration frequency could be reduced;

the conversion rate of DHTBZ from VBZ was 15.9%, the conversion rate of 11-P4 from compound 21-P3 was 26.8%; and compared to VBZ, compound 21-P3 had a higher conversion rate. Since the VMAT2-binding activity of VBZ and 21-P3 was much lower than that of DHTBZ and 11-P4, test results illustrated that at an equimolar dose, compared to VBZ, compound 21-P3 had higher availability and could produce much stronger efficacies.

(3) By gavage administration, compared to VBZ and DHTBZ, compound 21-P3 and compound 11-P4 had higher bioavailability.

Experimental Example 4 Pharmacodynamic Assessment of Compounds 21 and 21-P3 in SD Rats 1. Objective SD rat autonomous activity models were used in the study. VBZ xylene sulfonate was used as control. Equimolar doses of compounds 21 and 21-P3 were given in one single gavage. Movement distances of the rats in open field were compared to investigate the pharmacodynamic differences between compounds 21, 21-P3, and control medicament VBZ xylene sulfonate.

2. Experiment Materials 2.1 Test animals: 32 SD rats, SPF-grade, Male, 5-7 weeks old, weighing: 200-220 g, pre-accustomed for at least 1 week before the test. Animal source: Ji'nan Pengyue Laboratory Animal Technique Co., Ltd.; Animal Certification Number: SCXK (LU) 20140007

2.2 Test Medicaments

Compound 21: prepared according to Example 21

Compound 21-P3: prepared according to Example 31

VBZ xylene sulfonate: Jiangsu Vcare Pharmatech Co., Ltd., Lot No.: 334-1-1517-15

Preparation method: An appropriate amount of the medicament was weighed and dissolved with a small amount of DMSO (not more than 1% of the total volume). Then, 20% Solutol was added to obtain the desired medicament concentration and the final concentration of DMSO was <4%.

3. Test Grouping and Dosing

The day before the test, the rats were randomly divided into 4 groups according to body weights: control group (NS, without test medicament in the solvent), VBZ xylene sulfonate group, compound 21 group, 21-P3 group, 8 animals/group. The rats were put into the detection box, pre-accustomed for 10 min and fasted. Animal grouping and dosing information were detailed in Table 35.

TABLE 35

Animal grouping and dosing

| Group number | Group | Medicament administrated | Dosage of administration | Medicament concentration | Route of admimstration | Administration volume | Number of animals |
|---|---|---|---|---|---|---|---|
| 1 | NS | — | — | — | Gavage | 1 mL/200 g | 8 |
| 2 | VBZ | VBZ xylene sulfonate | 7.63 mg/kg | 1.53 mg/mL | Gavage | 1 mL/200 g | 8 |
| 3 | 21 | 21 | 4.87 mg/kg | 0.97 mg/mL | Gavage | 1 mL/200 g | 8 |
| 4 | 21-P3 | 21-P3 | 4.87 mg/kg | 0.97 mg/mL | Gavage | 1 mL/200 g | 8 |

4. Test Method

On the day of the test, the animals were accustomed for at least 1 hr in the test room. Rats in each group were given a vehicle or corresponding medicaments, respectively according to the doses in Table 35 in one single gavage and then put into the activity room. The total movement distances of rats from 2 hr to 3 hr post-dose were recorded and analyzed by using a TopScan monitoring system. Rats of a same group should not be put in one same room among the eight activity rooms, and there was at least one rat from the control group in each round of test to prevent mutual interference. At the end of each round of test, the feces were swept out and the activity rooms were cleaned to avoid the influence of irrelevant interfering factors (odor, etc.) on the exercise activities of the rats.

5. Observation Indexes

The total movement distances of rats from 2 hr to 3 hr post-dose were recorded and analyzed by using a TopScan monitoring system and the reduction rate (RR) of the total movement distance was calculated, wherein RR=(Control group movement distance-Administration group movement distance)/Control group movement distance*100%.

6. Statistic Analysis

Test data were expressed as mean±standard error of the mean (MEAN±SEM). Difference between various groups at each time point was compared by using PASW Statistics 18.0 software with one-way analysis of variance (ANOVA). All tests were two-sided tests, and $P<0.05$ indicated that the difference was statistically significant.

7. Test Results:

Compared to the control group (movement distance=16210±3465 mm), the VBZ group had significantly decreased rat autonomous activity distance (movement distance=4882±1022 mm, $P<0.05$); compound 21 group had decreased rat autonomous activity distance (movement distance=11630±2839 mm, $P>0.05$); and compound 21-P3 group had significantly decreased rat autonomous activity distance (movement distance=2956±1101 mm, $P<0.01$) and there was significant difference in comparison with the control group. The reduction rates of the total movement of VBZ group, compound 21 group and compound 21-P3 group were 69.9%, 28.3% and 81.8%, respectively. Compared to the VBZ group, the compound 21-P3 group showed stronger efficacies.

Experimental Example 5 Pharmacokinetic Assessment of Compound 11-P4 in SD Rats The test method was identical to Experimental Example 4. Animal grouping and dosing information were detailed in Table 36.

TABLE 36

Animal grouping and dosing information

| Group number | Group | Medicament administrated | Dosage of administration | Medicament concentration | Route of administration | Administration volume | Number of animals |
|---|---|---|---|---|---|---|---|
| 1 | 11-P4 | 11-P4 | 1.25 μmol/kg | 0.096 mg/mL | Gavage | 1 mL/200 g | 8 |
| 2 | 11-P4 | 11-P4 | 2.5 μmol/kg | 0.19 mg/mL | Gavage | 1 mL/200 g | 8 |
| 3 | 11-P4 | 11-P4 | 5 μmol/kg | 0.39 mg/mL | Gavage | 1 mL/200 g | 8 |
| 4 | 11-P4 | 11-P4 | 10 μmol/kg | 0.77 mg/mL | Gavage | 1 mL/200 g | 8 |
| 5 | VBZ | VBZ xylene sulfonate | 2.5 μmol/kg | 0.38 mg/mL | Gavage | 1 mL/200 g | 8 |
| 6 | VBZ | VBZ xylene sulfonate | 5 μmol/kg | 0.76 mg/mL | Gavage | 1 mL/200 g | 8 |
| 7 | VBZ | VBZ xylene sulfonate | 10 μmol/kg | 1.53 mg/mL | Gavage | 1 mL/200 g | 8 |
| 8 | NS | — | — | — | Gavage | 1 mL/200 g | 8 |

The total movement distances of rats from 0 hr to 1 hr post-dose were recorded and analyzed. Test results could be seen in Table 37. Compared to the control group (movement distance=14190±2785 mm), the three VBZ groups at the doses of 2.5 μmol/kg, 5.0 μmol/kg and 10.0 μmol/kg all had decreased rat autonomous activity distances, wherein the 5.0 μmol/kg and 10.0 μmol/kg groups had significant difference compared to the control group (movement distances being 8349±2536 mm, $P>0.05$; 6365±2564 mm, $P<0.05$;

6742±892.6 mm, P<0.05, respectively). Four 11-P4 groups at the doses of 1.25 μmol/kg, 2.5 μmol/kg, 5.0 μmol/kg and 10.0 μmol/kg all had decreased rat autonomous activity distance, with the three dose groups other than the 1.25 μmol/kg group having significant difference compared to the control group (movement distances being 9313±1213 mm, P>0.05; 5959±1615 mm, P<0.05; 1216±429.9 mm, P<0.01; 1355±524.1 mm, P<0.01, respectively).

TABLE 37

Reduction rate of total movement distance of rats in each group

| | Group | Reduction rate of total movement distance |
|---|---|---|
| VBZ | 2.5 μmol/kg | 41.2% |
| | 5.0 μmol/kg | 55.1% |
| | 10.0 μmol/kg | 52.5% |
| 11-P4 | 1.25 μmol/kg | 34.4% |
| | 2.5 μmol/kg | 58.0% |
| | 5.0 μmol/kg | 91.4% |
| | 10.0 μmol/kg | 90.5% |

Figure 14:
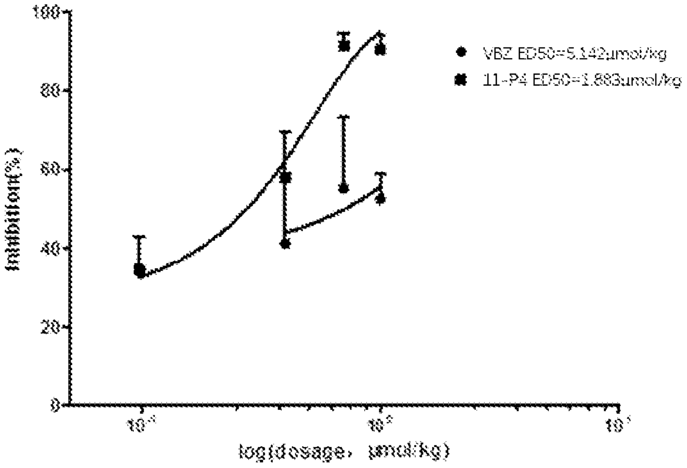
FIG. 14: dose-effect curves of VBZ and 11-P4

Inhibition rate of different doses of medicaments on rat autonomous activity were calculated, wherein inhibition rate=reduction rate of total movement distance (RR), and RR=(control group movement distance-administration group movement distance)/control group movement distance*100%; the dose-effect curves of VBZ and 11-P4 were obtained and could be seen in FIG. 14; and "log (inhibitor) vs. response-Variable slope" method of the software Graph Pad Prism 5 was used to calculate the ED50 values.

Test results showed that under equimolar dosing conditions, ED50 values of VBZ group and 11-P4 were 5.142 μmol/kg and 1.883 μmol/kg, respectively, and hence the effect of 11-P4 was obviously better than that of the VBZ group.

Experimental Example 6 Incubation Tests of Liver Microsomes from Five Species 1. Test Compounds Compounds 11-13, 15 and 16; Comparative Example 44 compound: prepared according to corresponding Examples above.

2. Test Process

Incubation: 100 μL of an incubation system included: liver microsomes (human, rat, mouse, monkey or dog) (0.5 mg/mL), sodium phosphate buffer (100 mM), and magnesium chloride (10 mM). Compounds 11-13, 15 and 16 and Comparative Example 44 compound were added into the incubation systems to a final concentration of 1 μM. After pre-incubation of the systems at 37° C. for 3 min, NADPH was added to a final concentration of 1 mM. The reaction was started. After the systems were incubated for 0 min, 5 min, 15 min, 30 min, and 60 min, 200 μL of ice-cold acetonitrile was added to terminate the reaction and the reaction systems were stored at −20° C. for detection. Each sample at each time point was processed parallelly in duplicate and a blank control group without coenzymes and a positive control group were provided.

3. Sample Analysis and Data Processing

A certain amount of internal standard was added to the sample following termination with acetonitrile. After centrifugation at 13000 rpm for 10 min, the supernatant was diluted with water 1:1 (V/V) and the concentrations of compounds 11-13, 15 and 16 and Comparative Example 44 compound were determined by using the LC-MS/MS method. Relative remaining amount was taken as the ordinate and time as the abscissa. Semi-log plotting was used to calculate the elimination rate constant k of each compound and the equation $t_{1/2}$=0.693/k was used to calculate the elimination half-life ($t_{1/2}$) of each compound in the liver microsome incubation system, and the results could be seen in Table 38.

The results showed that in the liver microsomes of mouse and monkey, compound 11 had a longer half-life than DHTBZ; in addition, compound 12 and compound 13 also had relatively good liver microsome stability.

TABLE 38

Elimination half-life ($t_{1/2}$, min) of various compounds in liver microsomes from different species

| Species | Compound 11 | Compound 12 | Compound 16 | Compound 13 | Compound 15 | Comparative Example 44 | DHTBZ |
|---|---|---|---|---|---|---|---|
| Human | 161.2 | ~ | 86.6 | 154.0 | 39.4 | 157.5 | ~ |
| Rat | ~ | ~ | ~ | ~ | 67.9 | ~ | ~ |
| Mouse | 23.0 | 29.9 | 19.4 | 78.8 | 5.1 | 22.6 | 13.4 |
| Dog | ~ | ~ | 126.0 | ~ | 22.6 | 64.2 | 115.5 |
| Monkey | 58.7 | 85.6 | 14.3 | 50.6 | 7.4 | 26.2 | 26.3 |

"~", the data showed that the metabolism was stable and the rate of the original compound left was greater than 80% after an incubation of 60 min.

Experimental Example 7 Excipient Compatibility Test of Compound 11-P4 and Crystal Form A of Compound 11-P4S 1. Test Medicaments Compound 11-P4: prepared according to Example 29 crystal form A of compound 11-P4S: prepared according to Example 30

2. Test Method

Compound 11-P4 and crystal form A of compound 11-P4S were mixed with excipients at ratio of 1:20, respectively. Then the mixture was placed open at 60° C. for 5 days. Compound 11-P4/crystal form A of compound 11-P4S were sampled and had purities detected.

Purity detection method: about 35 mg of the sample was weighed precisely and placed in a 25 ml measuring flask. 15 ml of acetonitrile was added to dissolve the sample by ultrasound. Water was used to dilute to a given mark and the mixture was shaken uniformly and used as sample solution to be tested. Determination was carried out based on high performance liquid chromatography, octadecyl silane bonded silica gel was used as the filler (Inerstil ODS-3V, 250 mm×4.6 mm, 5 μm); 10 mmol/L diammonium hydrogen phosphate solution (adjusting the pH value to 6.95±0.05)-acetonitrile (80:20) was used as mobile phase A, acetonitrile was used as mobile phase B, and gradient elution was carried out according to Table 39. The detection wavelength was 282 nm; the column temperature was 35° C.; and the flow rate was 1.0 ml/min. 10 μl of the sample solution to be tested was precisely measured and injected into the liquid chromatograph, and the chromatogram was recorded. Calculation was carried out by the peak area normalization method.

TABLE 39

Mobile phase gradient

| Time (min) | Mobile phase A (%) | Mobile phase B (%) |
|---|---|---|
| 0 | 75 | 25 |
| 10 | 75 | 25 |
| 30 | 25 | 75 |
| 45 | 25 | 75 |
| 47 | 75 | 25 |
| 60 | 75 | 25 |

3. Test Results could be Seen in Table 40.

TABLE 40

Excipient compatibility test results

| | API | | MCC | Magnesium stearate | Talc powder |
|---|---|---|---|---|---|
| Compound | 0 d | High temperature (60° C.)-5 d | High temperature (60° C.)-5 d | High temperature (60° C.)-5 d | High temperature (60° C.)-5 d |
| 11-P4 purity | 99.74% | 99.54% | 96.76% | 98.31% | 98.26% |
| 11-P4S Crystal form A purity | 99.70% | 99.69% | 99.26% | 99.68 | 99.68% |

The results showed that after 11-P4 and the above-mentioned excipients were mixed and placed at high temperature for 5 days, the purity dropped obviously, whereas the purity of crystal form A of 11-P4S had no obvious change, which illustrated that crystal form A of 11-P4S had better excipient compatibility and facilitated the development of formulations.

Experimental Example 8 11-P4S Crystal Forms A/D/E Suspension Competition Test 1. Test Medicaments crystal forms A/D/E of compound 11-P4S: prepared according to Example 30

2. Test Method:

To IPA and IPAc saturated solutions of 11-P4S crystal form A (2 mL), 11-P4S crystal forms A/D/E (5 mg each) were added, respectively, suspended and stirred at room temperature/50° C. for 17 hours. Then XRPD was carried out on the solid.

Figure 15:
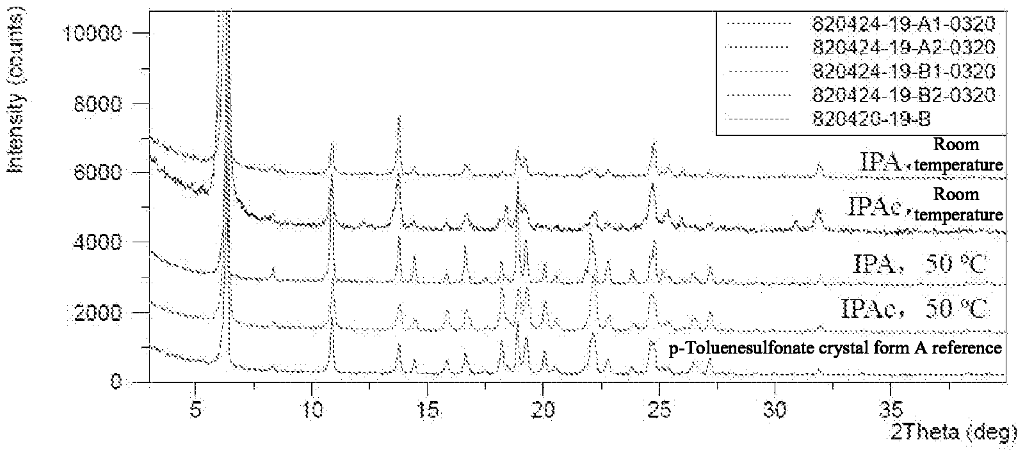
FIG. 15: XRPD overlay of 11-P4S crystal forms A/D/E suspension competition results

3. Test results could be seen in Table 41 and FIG. 15.

TABLE 41

Suspension competition results

| Raw material | Solvent | Temperature | Time | Results |
|---|---|---|---|---|
| 11-P4S crystal forms A/D/E | IPA | Room temperature | 17 h | 11-P4S crystal form A |
| | IPAc | Room temperature | 17 h | 11-P4S crystal form A |
| | IPA | 50° C. | 17 h | 11-P4S crystal form A |
| | IPAc | 50° C. | 17 h | 11-P4S crystal form A |

The results showed that: All systems obtained 11-P4S crystal form A and crystal form A, which illustrated that 11-P4S crystal form A was the most thermodynamically stable crystal form at temperatures from room temperature to 50° C.

The invention claimed is:

1. A compound represented by formula (I), or a stereoisomer or pharmaceutically acceptable salt thereof, (I)

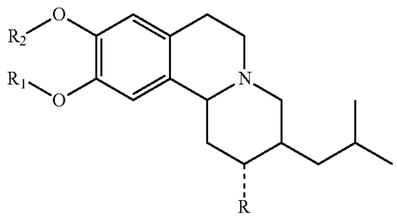

wherein

"- - - " represents a single bond or a double bond;

when "- - - " is a single bond, R is selected from OH, H or

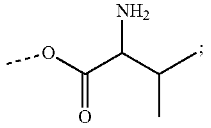

when "- - - " is a double bond, R is O;

$R_1$ is selected from hydrogen, methyl or ethyl;

$R_2$ is unsubstituted $C_{3-6}$ cycloalkyl, $C_{3-6}$ cycloalkyl-$C_{1-6}$ alkyl, or 3- to 6-membered heterocycloalkyl-$C_{1-3}$ alkyl, or $R_2$ is $C_{3-6}$ cycloalkyl substituted with 1, 2 or 3 $R_3$, $C_{3-6}$ cycloalkyl-$C_{1-6}$alkyl substituted with 1, 2 or 3 $R_3$, or 3- to 6-membered heterocycloalkyl-$C_{1-3}$ alkyl substituted with 1, 2 or 3 $R_3$, or $R_2$ is $C_{2-10}$ alkyl substituted with 2 or 3 $R_3$; and $R_3$ is F, Cl, Br, SH or $NH_2$.

2. The compound, or the stereoisomer or pharmaceutically acceptable salt thereof according to claim 1, wherein $R_2$ is selected from unsubstituted $C_{3-6}$ cycloalkyl-$C_{1-6}$alkyl, or $C_{2-5}$ alkyl substituted with 2 or 3 $R_3$; wherein $R_3$ is F, Cl, or Br.

3. The compound, or the stereoisomer or pharmaceutically acceptable salt thereof according to claim 1, wherein $R_1$ is methyl;

$R_2$ is trifluoroethyl, trifluoropropyl, trifluorobutyl, trifluoropentyl, bisfluoroethyl or cyclopropanemethylene;

"- - - " is a single bond, R is selected from OH or

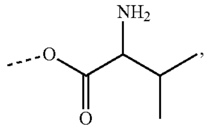

or "- - - " is a double bond, and R is O.

4. The compound, or the stereoisomer or pharmaceutically acceptable salt thereof according to claim 1, wherein the compound is selected from:

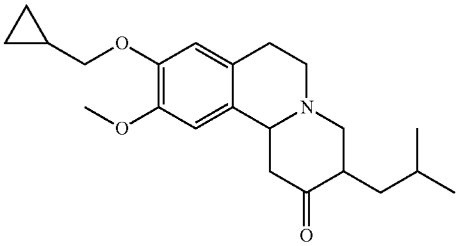

,

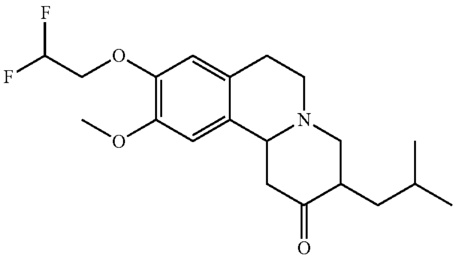

,

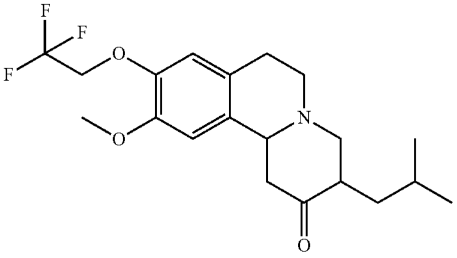

,

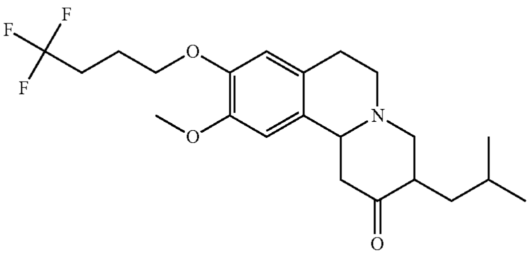

,

-continued

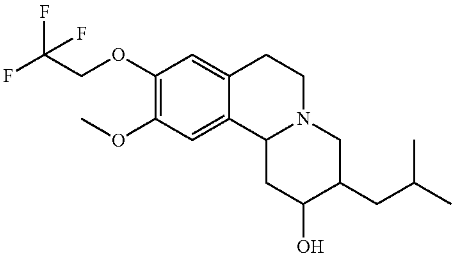

,

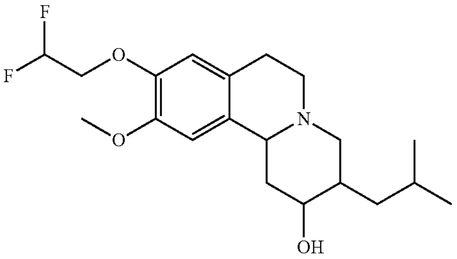

,

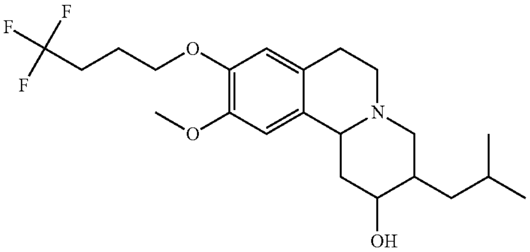

,

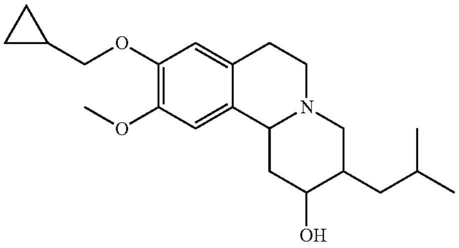

,

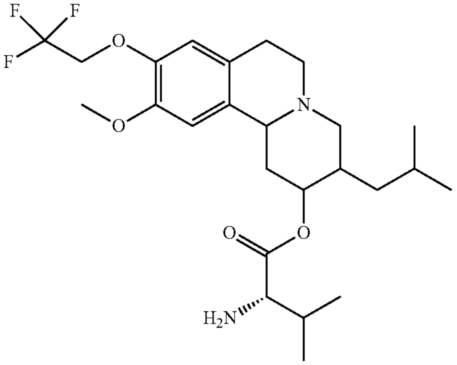

,

-continued
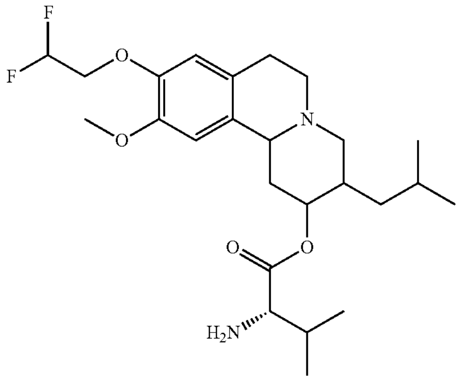
,
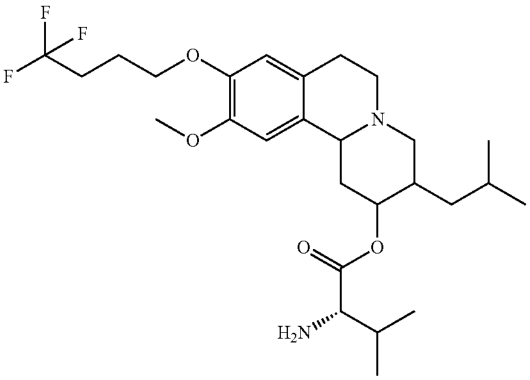
,
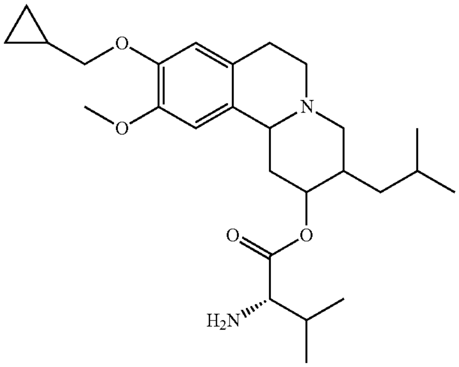
,
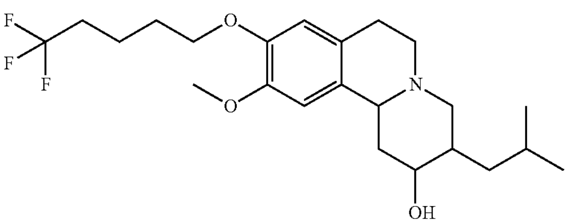
,
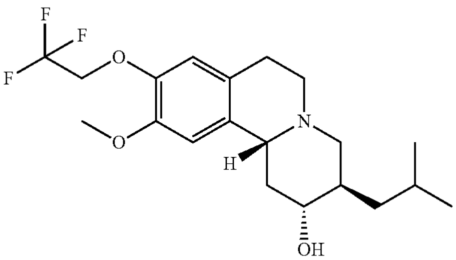
,
-continued
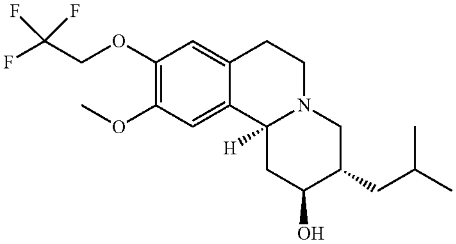
,
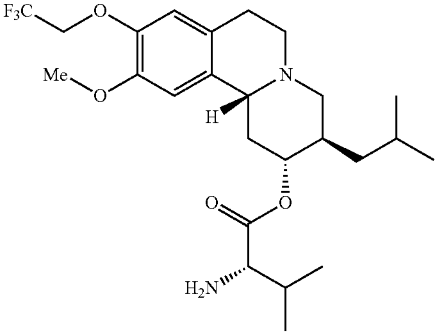
,
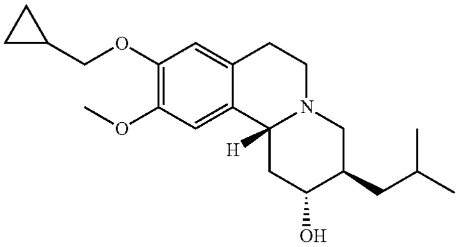
,
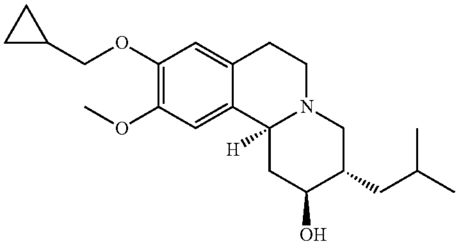
,
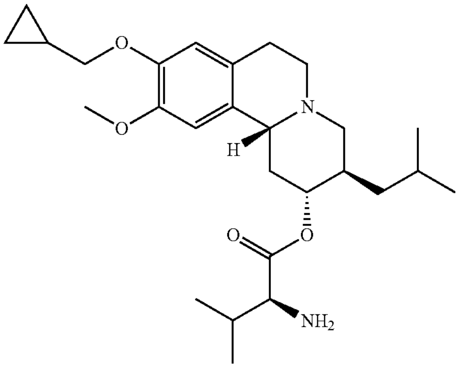
.
5. The compound according to claim 1, wherein the compound is a p-toluenesulfonate salt of Formula (I) selected from the group consisting of:

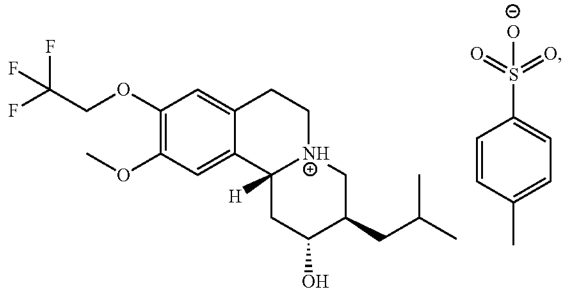

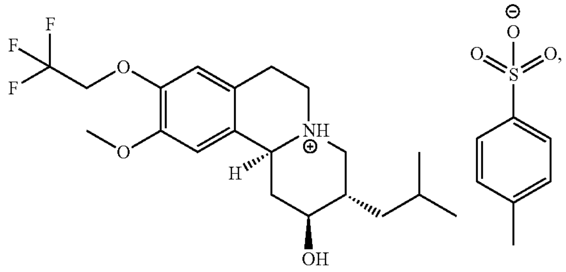

and

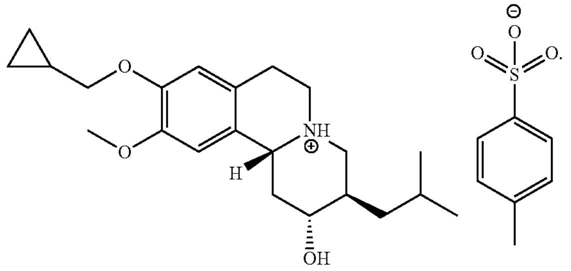

6. The compound of claim 5 having the formula below:

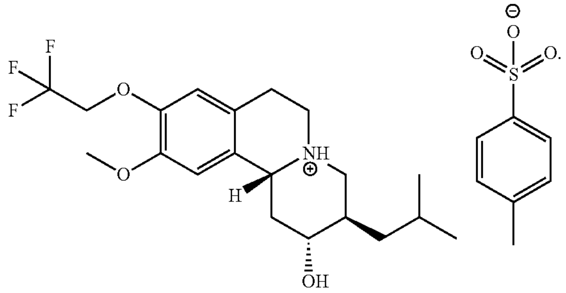 [SMILES: COc1cc2c(cc1OCC(F)(F)F)CC[NH+]1C[C@@H](CC(C)C)[C@H](O)C[C@H]21 ; Cc1ccc(S(=O)(=O)[O-])cc1]

7. The compound according to claim 6 having a crystal form belonging to the orthorhombic system with a space group of $P2_12_12_1$, and unit cell parameters of a=27.14408 (13) Å, b=16.24056(7) Å, c=6.13775(3) Å, α=90°, β=90°, γ=90°, V=2705.74(2) Å3, Z=4.

8. The compound according to claim 6 having a crystal form comprising characteristic peaks of 2θ diffraction angle at 6.33±0.2°, 10.87±0.2° and 18.89±0.2° as measured by the X-ray powder diffraction using Cu—Kα radiation.

9. The compound according to claim 6 having crystal form B, said crystal form B comprising characteristic peaks of 2θ diffraction angle at 6.32±0.2°, 5.42±0.2° and 10.85±0.2° as measured by the X-ray powder diffraction using Cu—Kα radiation.

10. The compound according to claim 6 having crystal form C, said crystal form C comprising characteristic peaks of 2θ diffraction angle at 5.81±0.2°, 6.33±0.2° and 12.86±0.2° as measured by the X-ray powder diffraction using Cu—Kα radiation.

11. The compound according to claim 6 having crystal form D, said crystal form D comprising characteristic peaks of 2θ diffraction angle at 6.02±0.2° and 23.91±0.2° as measured by the X-ray powder diffraction using Cu—Kα radiation.

12. The compound according to claim 5 having the formula below:

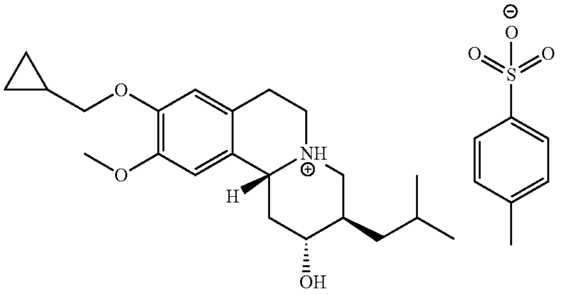 [SMILES: COc1cc2c(cc1OCC1CC1)CC[NH+]1C[C@@H](CC(C)C)[C@H](O)C[C@H]21 ; Cc1ccc(S(=O)(=O)[O-])cc1]

wherein the compound has a crystal form of the orthorhombic system with a space group of $P2_12_12_1$, and unit cell parameters of a=6.28880(10) Å, b=15.7958(3) Å, c=27.9234(6) Å, α=90°, β=90°, γ=90°, V=2773.82(9) Å3, Z=4.

13. The crystal form of the compound according to claim 6 having crystal form E, said crystal form E comprising characteristic peaks of 2θ diffraction angle at 6.06±0.2°, 18.32±0.2° and 30.79±0.2° as measured by the X-ray powder diffraction using Cu—Kα radiation.

14. A pharmaceutical composition comprising the compound, or the stereoisomer or pharmaceutically acceptable salt thereof according to claim 1, and a pharmaceutically acceptable carrier.

15. A method for preparing a compound of formula (II), comprising the following preparation steps:

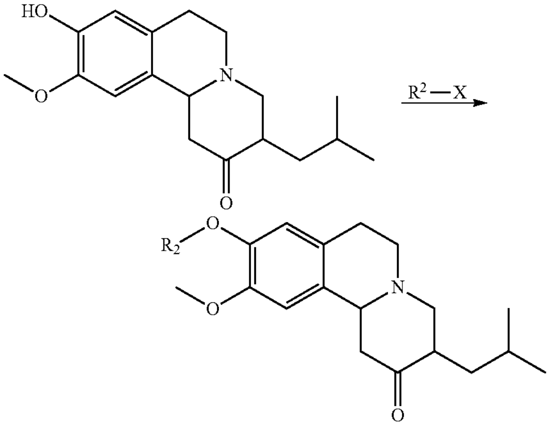

or (II)

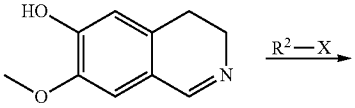

-continued

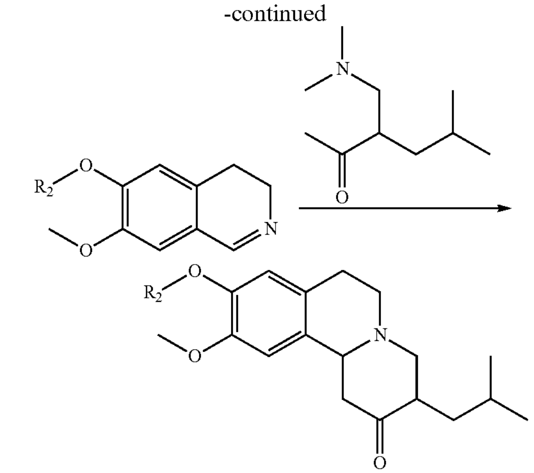

(II)

or

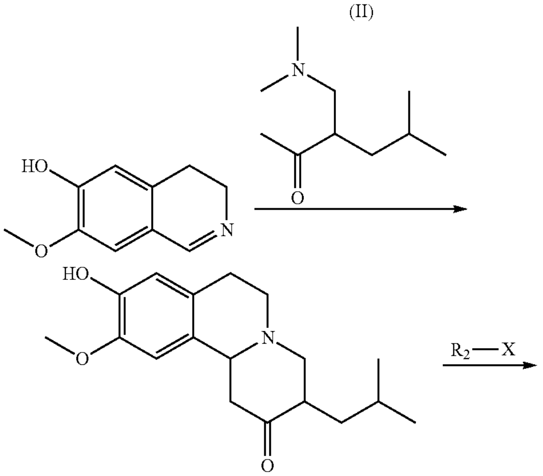

-continued

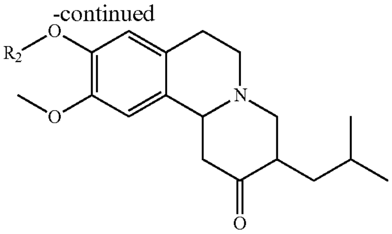

(II)

wherein $R_2$ is selected from unsubstituted $C_{3-6}$cycloalkyl-$C_{1-6}$alkyl, or, $C_{2-10}$alkyl substituted with 2 or 3 $R_3$, $R_3$ is selected from F, Cl, Br or $NH_2$; and X is a leaving group.

16. The method according to claim 15, wherein, $R_2$ is trifluoroethyl, trifluoropropyl, trifluorobutyl, trifluoropentyl, bisfluoroethyl or cyclopropanemethylene, and X is Cl, Br or I.

17. A method of treating a subject having a VMAT2 related disease or disorder, the method comprising administering to the subject the compound of claim 1 or a polymorph, stereoisomer or pharmaceutically acceptable salt thereof.

18. A method of treating a subject having a hyperkinesis disorder, the method comprising administering to the subject the compound of claim 1 or a polymorph, stereoisomer or pharmaceutically acceptable salt thereof.

19. The method of claim 18 wherein the hyperkinesis disorder is Huntington's disease, tardive dyskinesia, Tourette syndrome or convulsion.

* * * * *